United States Patent
Miller et al.

(10) Patent No.: US 10,993,657 B1
(45) Date of Patent: May 4, 2021

(54) WEARABLE HYDRATION MONITOR SENSORS

(71) Applicant: Halo Wearables, LLC, Morgan, UT (US)

(72) Inventors: David R. Miller, Morgan, UT (US); Devin W. Miller, Morgan, UT (US)

(73) Assignee: Halo Wearables, LLC, Morgan, UT (US)

( * ) Notice: Subject to any disclaimer, the term of this patent is extended or adjusted under 35 U.S.C. 154(b) by 972 days.

(21) Appl. No.: 15/394,305

(22) Filed: Dec. 29, 2016

Related U.S. Application Data

(60) Provisional application No. 62/273,357, filed on Dec. 30, 2015, provisional application No. 62/273,360, filed on Dec. 30, 2015.

(51) Int. Cl.
*A61B 5/00* (2006.01)
*A61B 5/01* (2006.01)
*G01N 25/62* (2006.01)

(52) U.S. Cl.
CPC .............. *A61B 5/4875* (2013.01); *A61B 5/01* (2013.01); *A61B 5/4266* (2013.01); *A61B 5/681* (2013.01); *A61B 5/742* (2013.01); *G01N 25/62* (2013.01)

(58) Field of Classification Search
CPC ....... A61B 5/4875; A61B 5/681; A61B 5/742; A61B 5/4266; A61B 5/01; G01N 25/62
USPC .......................................... 600/307
See application file for complete search history.

(56) References Cited

U.S. PATENT DOCUMENTS

| | | | | |
|---|---|---|---|---|
| 4,066,068 A * | 1/1978 | Nilsson | ................ | A61B 5/4283 600/307 |
| 5,131,390 A * | 7/1992 | Sakaguchi | ........... | A61B 5/4261 600/346 |
| 6,966,877 B2 * | 11/2005 | Lahtinen | .............. | A61B 5/4266 600/306 |
| 9,990,172 B2 * | 6/2018 | Komaromi | ........... | H04R 25/305 |
| 2003/0185786 A1 * | 10/2003 | Uchiwa | .................... | A61K 8/39 424/78.03 |

(Continued)

FOREIGN PATENT DOCUMENTS

EP     2851001 A2 *  3/2015    ........ H04M 1/72569

OTHER PUBLICATIONS

Salvo et al., A Wearable Sensor for Measuring Sweat Rate, IEEE Sensors Journal, vol. 10, No. 10, Oct. 2010, pp. 1557-1558 (Year: 2010).*

(Continued)

*Primary Examiner* — Jacqueline Cheng
*Assistant Examiner* — Tho Q Tran
(74) *Attorney, Agent, or Firm* — Miller IP Law, LLC

(57) ABSTRACT

Described herein are apparatuses and methods for measuring a hydration condition with a wearable device. The wearable device may include a housing, a flume integrated into the housing, and a sensor array. The housing may include a perimeter wall disposed around a perimeter of the housing between a top wall and a bottom wall, where the top wall, bottom wall, and perimeter wall form an inner cavity. The flume may be disposed in the inner cavity, where a first end of the flume is disposed at the bottom wall and a second end of the flume is disposed at the top wall. The sensor array may include a first vapor pressure sensor located within the flume at a first location and a second vapor pressure sensor located within the flume at a second location.

19 Claims, 19 Drawing Sheets

(56) References Cited

U.S. PATENT DOCUMENTS

| | | | | |
|---|---|---|---|---|
| 2006/0247709 A1* | 11/2006 | Gottesman | ......... | A61N 1/37282 |
| | | | | 607/30 |
| 2011/0048108 A1* | 3/2011 | Yamagishi | ......... | G01N 33/0037 |
| | | | | 73/31.06 |
| 2015/0335290 A1* | 11/2015 | Hunter | ..................... | A61B 5/01 |
| | | | | 623/1.13 |

OTHER PUBLICATIONS

Adams et al., A method for the measurement of physioloc evaporative water loss, US Government Printing Office (Year: 1964).*

* cited by examiner

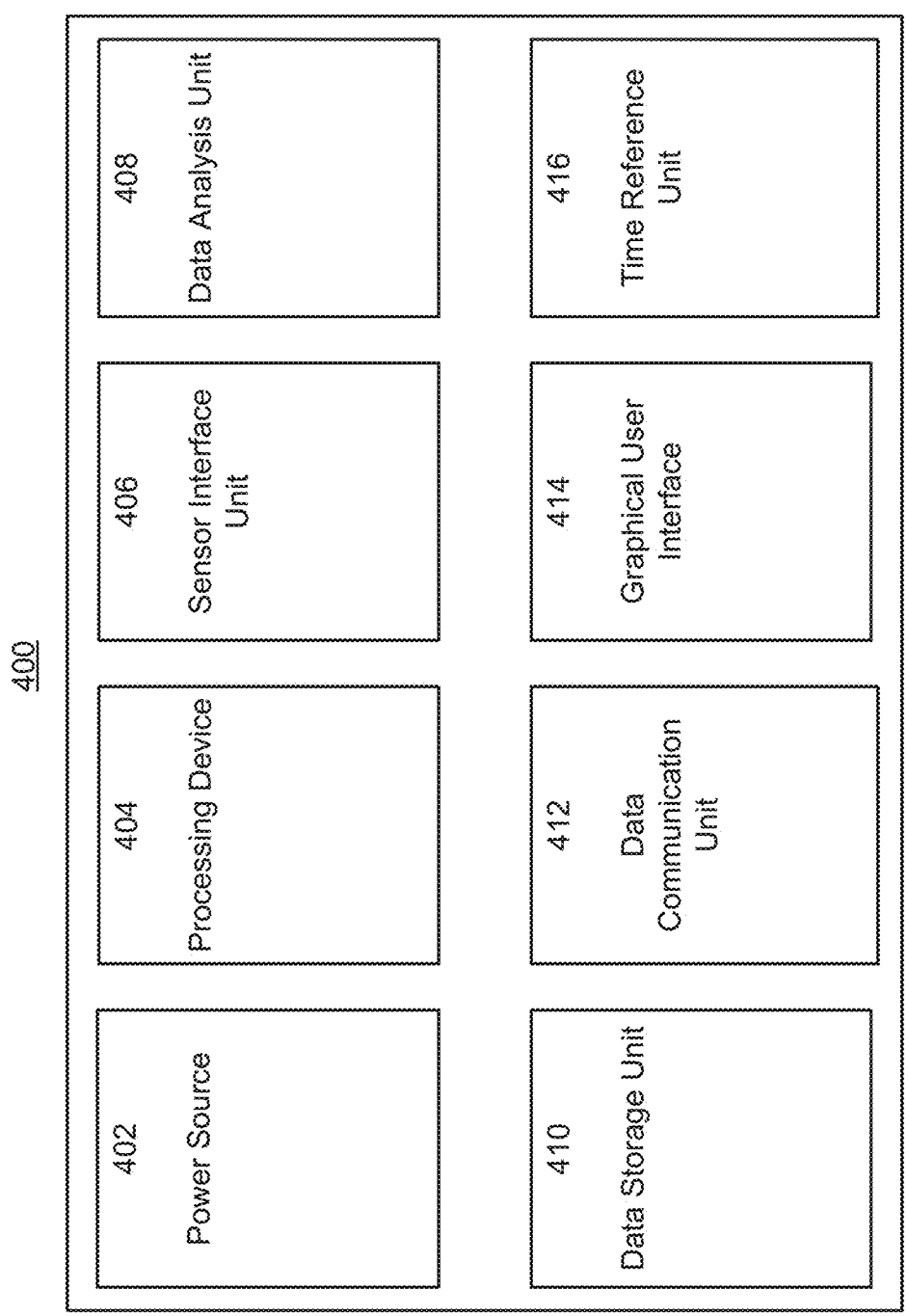

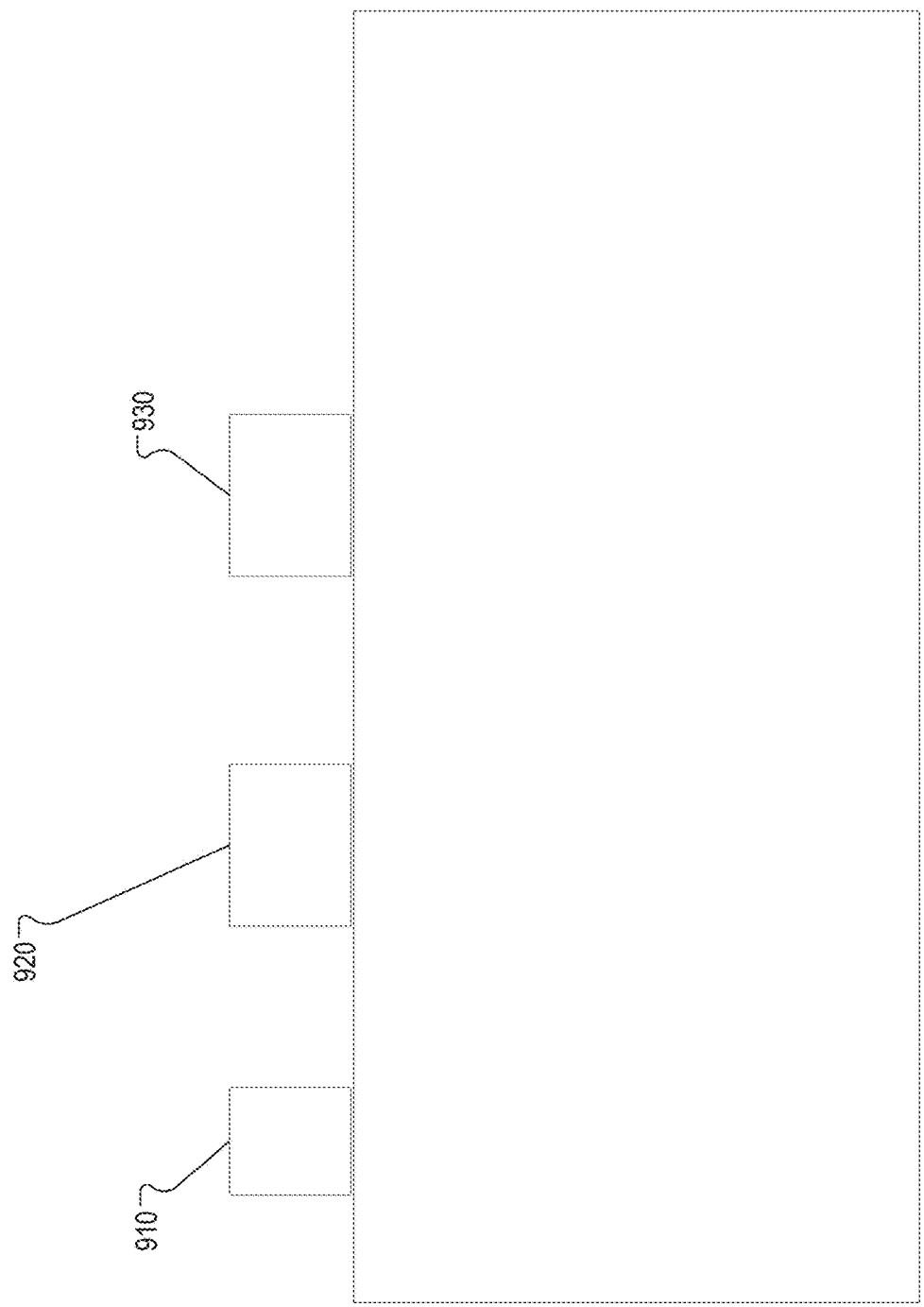

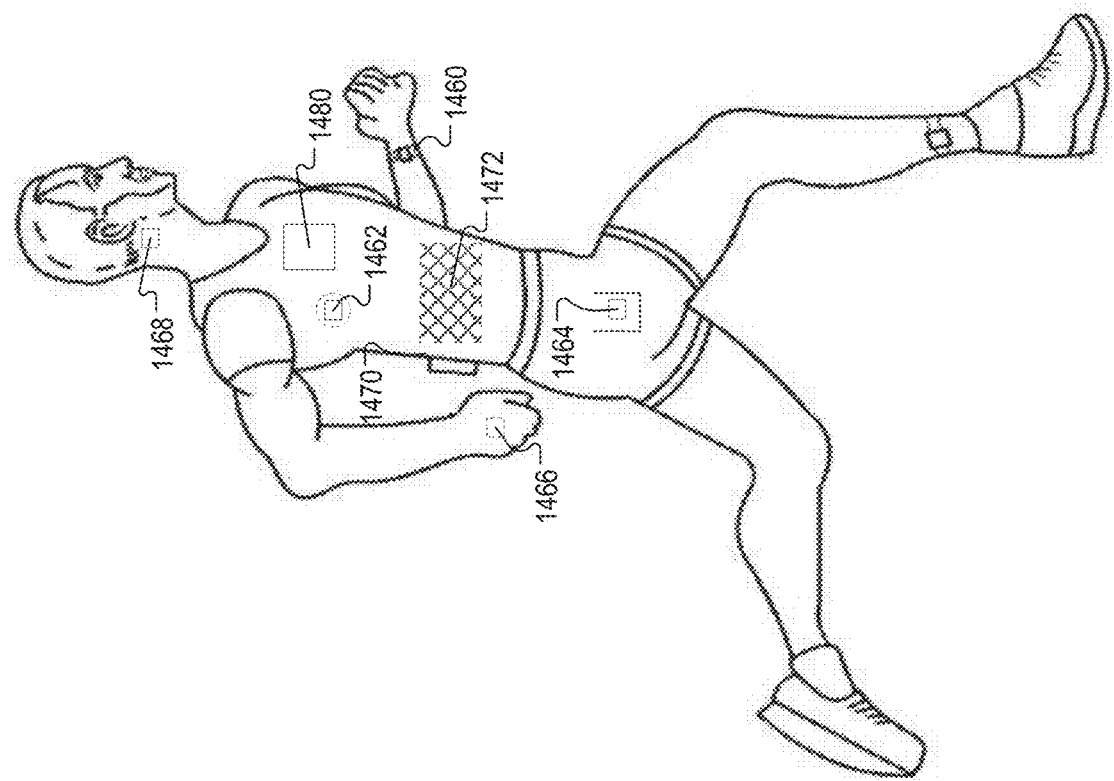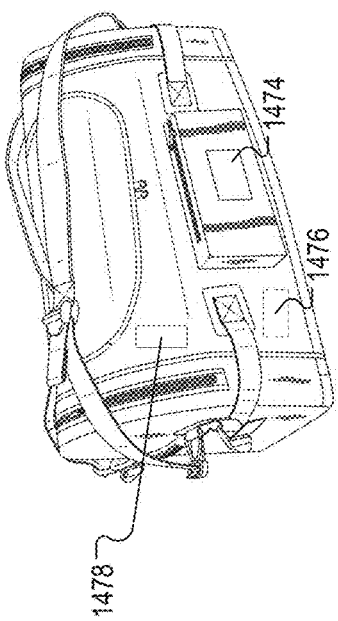
FIG. 14

WEARABLE HYDRATION MONITOR SENSORS

CROSS-REFERENCE TO RELATED APPLICATION

This application claims the benefit of U.S. Provisional Application No. 62/273,357, filed Dec. 30, 2015, and U.S. Provisional Application No. 62/273,360, filed Dec. 30, 2015, the entire disclosure of which is incorporated herein by reference.

BACKGROUND

Dehydration is a condition in which water in a living body decreases below the individual's normal functioning level. Dehydration often occurs when an individual is exercising for extended periods of time, an individual intakes little or no water, or the temperature rises to a point where an individual cannot excrete enough sweat to maintain their normal body temperature. Persons that regularly exert themselves in low humidity and/or high-temperature conditions and/or for extended periods of time are prone to experience dehydration or dehydration symptoms. Elderly persons and children are also especially prone to experience dehydration or dehydration symptoms.

BRIEF DESCRIPTION OF THE DRAWINGS

The disclosure will be understood more fully from the detailed description given below and from the accompanying drawings of various embodiments of the disclosure. The drawings, however, should not be taken to limit the disclosure to the specific embodiments, but are for explanation and understanding only.

FIG. 4 illustrates a block diagram of an electronic device according to one embodiment.

FIG. 9 illustrates an air flow sensor according to one embodiment.

FIG. 14 illustrates a body area network (BAN) devices communicating using a BAN according to one embodiment.

DESCRIPTION OF EMBODIMENTS

Figure 1:
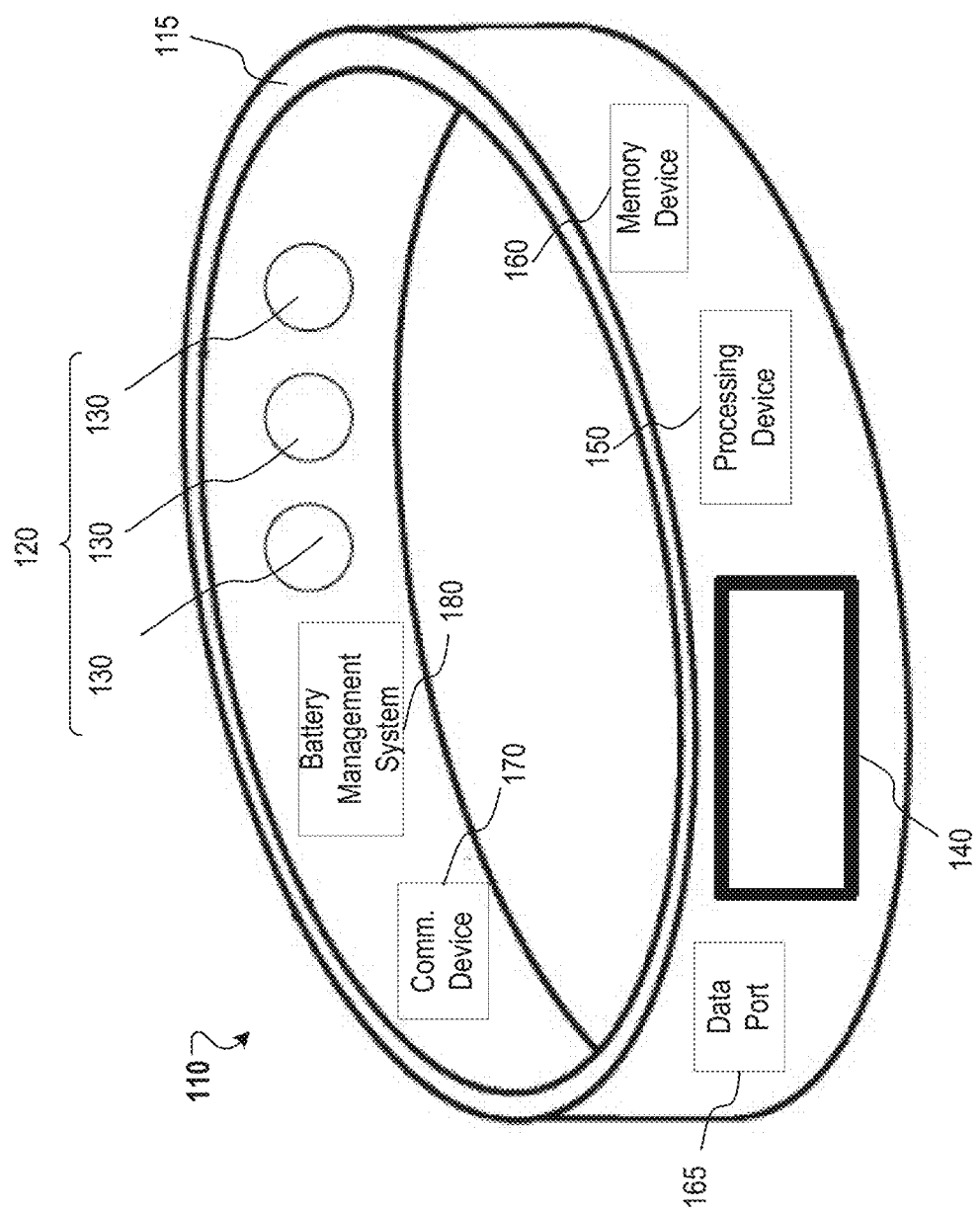
FIG. 1 illustrates an electronic device according to one embodiment.

When a person experiences a dehydrated condition, the individual's ability to perform tasks will begin to deteriorate. For example, in the case of a long distance endurance athlete, an individual that becomes dehydrated by the loss of as little as 2% body weight of fluid may begin to have their performance impaired. Losses in excess of 5% body weight of fluid can decrease the capacity of an individual to perform a task by as much as 30%.

Conventionally, an individual's hydration level may be determined by different tests. One test is a body mass test where an individual is periodically weighed on a scale. Another test is a blood test where blood is drawn periodically to test hemoglobin concentration and hematocrit, sodium concentration, or plasma osmolality. Another test is a urine test where urine is sampled periodically such as a 24-hour urine collection to test osmolality, specific gravity, conductivity, color, volume, or frequency. Another test is a saliva test where saliva is periodically tested for flow rate, osmolality, or composition. One or more of these tests may be performed in a clinic environment or in a research lab. One or more of the tests may be performed at home over time with periodic measurements and observations. The conventional tests take time, calculations, measurements, and record keeping. In some cases, the conventional tests may be invasive to the individual and require a laboratory. The conventional tests may also increase a potential biohazard risk as various people have differing involvement with each of these processes. For example, a person may take a urine or saliva sample and then not properly dispose of the sample. There is a need for devices and methods to monitor an individual's hydration condition in a non-invasive manner. Additionally, as the conventional tests may only be performed periodically, an individual may become dehydrated between the periodic tests without being aware of the dehydrated condition.

Aspects of the present disclosure overcome this and other deficiencies by measuring a hydration condition. A hydration condition may be a current hydration condition or a future hydration condition. The hydration condition may be in the form of a score or index (e.g., Halo score, Halo index, and so forth). In one embodiment, an individual's hydration level is monitored regularly and any change in hydration is detected in the early stage before an individual's performance levels are impacted or they reach a serious dehydrated condition. One way to measure an individual's hydration level is through measuring the individual's sweat rate.

Sweat rate measurements over time can indicate how much water an individual has lost. In one example, a first humidity measurement and/or a first temperature measurement of an individual may be measured. A first vapor pressure measurement of the individual may be calculated from the first humidity measurement and/or the first temperature measurement. A second humidity measurement and/or a second temperature measurement of an individual may be measured. A second vapor pressure measurement of the individual may be calculated from the sweat rate may be determined from the first vapor pressure measurement and the second vapor pressure measurement.

An initial hydration condition may be determined from information of the individual. The initial hydration condition may include a total body water measurement. A water loss of the individual may be determined from the sweat rate and information of the individual. An adjusted hydration condition may be calculated from the initial hydration condition and the water loss of the individual. The adjusted hydration condition may indicate water loss as a percent of body weight.

Another way to measure an individual's hydration level is through measuring air flow, ambient temperature, ambient humidity, and/or skin temperature. The hydration condition of an individual may be affected as the temperature rises and as the temperature lowers. For example, the body temperature rises when the ambient temperature is higher than the skin temperature. The body will transport heat through sweat to the surface of the body, but heat dissipation will only occur as the sweat evaporates from the body. If the sweat evaporation rate is lower than the sweat rate, the sweat rate may increase in an attempt to increase heat dissipation. Air flow can increase the rate of sweat evaporation. High ambient humidity can decrease the rate of sweat evaporation. The ambient temperature, skin temperature, air flow, and ambient humidity can cause an individual's sweat rate to increase and can affect the hydration condition of the individual.

In another example, as the ambient temperature lowers below skin temperature, the body temperature may decrease which may constrict blood vessels to reduce the flow of blood to the skin to reduce heat loss from the skin to the environment. The constriction of blood vessels may cause an individual to incorrectly perceive that they are properly hydrated and decrease the individual's thirst response. The constriction of blood vessels may also cause blood pressure to rise and to regulate blood pressure, the kidneys may filter fluid from the blood, filling the bladder with the excess fluid, and increasing urine production. The body's decreased thirst response and increased urine production may affect the body's hydration condition. Air flow can make the apparent temperature feel cooler as the air flow wicks heat away from the body through convection, thereby affecting the body's hydration condition. High humidity can make the apparent temperature feel cooler because the water in the humid air has a higher specific heat than air. Therefore cold air with a higher humidity may transfer heat from a body at a higher rate than cold air at a lower humidity, thereby affecting the body's hydration condition. The ambient temperature, skin temperature, air flow, and ambient humidity can cause an individual's blood vessels to constrict and can affect the hydration condition of the individual.

In one embodiment, ambient temperature, ambient humidity, air flow, and skin temperature measurements may be taken regularly to detect dehydration in the early stage before an individual's performance levels are impacted or they reach a serious dehydration condition. In another embodiment, ambient temperature, ambient humidity, air flow, and/or skin temperature measurements may be measured regularly to predict a dehydration condition to help prevent the dehydration condition. In another embodiment, ambient temperature, ambient humidity, air flow, and/or skin temperature measurements may be measured regularly to explain a hydration condition.

An ambient temperature measurement can indicate a baseline temperature or baseline. Other measurements combined with the baseline can indicate an adjusted baseline temperature or adjusted baseline. The adjusted baseline temperature and user measurements over time may indicate how much water an individual has lost or may be used to predict how much water the individual may lose. An ambient measurement may be apparent temperature, relative temperature, feels-like temperature, or another measurement. In one embodiment, an ambient humidity measurement, an air flow measurement, an ambient temperature measurement, and/or a skin temperature measurement may be measured. An adjusted baseline may be determined from the ambient humidity measurement, the air flow measurement, and/or the ambient temperature measurement. An adjusted hydration condition may be determined from the adjusted baseline, the skin temperature measurement, and one or more physiological measurements. The adjusted hydration condition may indicate a current hydration condition or may predict a future hydration condition in view of the adjusted baseline, the skin temperature measurement, and one or more physiological measurements.

The embodiments described herein may be directed to measuring the sweat rate or the skin temperature of an individual and/or the ambient temperature, the ambient humidity, the air flow approximate the individual to determine a hydration condition of the individual. A hydration condition of an individual may be determined by different types of measurements. The hydration condition of the individual may include a hypo-hydrated level (dehydrated or under hydrated condition), a euhydrated level (normal hydration condition), or a hyper-hydrated level (over hydrated condition). In one embodiment, a measurement may indicate that the individual is trending towards a dehydrated condition. In another embodiment, a measurement may indicate a user is trending towards a normal hydration condition. In another embodiment, a measurement may indicate that the individual is trending towards an over-hydrated condition.

An electronic device may perform one or more of the sweat rate, the skin temperature, the ambient temperature, the ambient humidity, or the air flow measurements to determine an adjusted hydration condition. An electronic device may have a top wall, a bottom wall, and a perimeter wall that form an inner cavity. A wall may also be referred to herein as a side or portion. Sweat rate, ambient temperature, ambient humidity, and air flow sensors may be integrated into the top wall of the housing. A skin temperature sensor may be integrated into the bottom wall of the housing. The sweat rate, ambient temperature, ambient humidity, air flow, and skin temperature sensors may be coupled with a flexible circuit board disposed in the inner cavity. A processor coupled with the flexible circuit board may determine an adjusted hydration condition based on one or more of the sweat rate, ambient temperature, ambient humidity, air flow, or skin temperature measurements.

FIG. 1 illustrates an electronic device 110 according to one embodiment. FIG. 1 illustrates that the electronic device 110 may be a wristband, a headband, an armband, a chest band, a leg band, an ankle band, a strap, a garment or piece of clothing (such as a hardhat or shirt), an accessory, or other object that may be shaped to attach or couple to a user. The electronic device 110 can also be integrated into other wearable objects such as a hard hat, a safety harness, a safety lockout, shoes, a bag, and so forth.

In one example, the electronic device 100 may be located in an area that is comfortable for the user to wear the electronic device 110 for an extended period of time, such as a 24-hour period. For example, as many individuals are accustomed to wearing wristwatches, a comfortable location for the individual to wear the electronic device 110 for an extended period of time is a wrist location. In another example, the electronic device may be located at a location on the user that will provide highest measurement accuracy level, such as a location on the user that is the most sensitive to a selected physiological measurement. For example, the chest, wrist, tip of the finger, or earlobe may be locations that provide a high level of accuracy to take physiological measurements compared to other locations on the body of the user and the electronic device 110 may be shaped to attach to the user at chest, wrist, tip of the finger, or earlobe locations.

In one embodiment, the electronic device 110 may include a housing 115 with one or more inner cavities. The one or more cavities may include space to house: a sensor array 120, a sensor 130, a display 140, a processing device 150, a memory device 160, a communication device 170, and/or a battery management system (BMS) 180. In one embodiment, the housing 115 may be hermetically sealed, e.g., airtight, waterproof, sweat proof, dust proof, and so forth. In another example, the housing may be a unibody (e.g., a single unit), where components such as the sensor 130 may be sealed within the unibody. In another embodiment, the housing 115 may include multiple pieces, such as a first housing piece and a second housing piece, that are sealed together to form a hermetically sealed housing 115. In another embodiment, the housing 115 may include multiple pieces, such as a first housing piece and a second housing piece that are coupled by at least one of induction connection or electrical connection.

In one example, the electronic device 110 may be an invasive device attachable to (or implantable within) a body of a user to obtain invasive physiological measurements from the user. In another example, the electronic device 110 may be a non-invasive device attachable to the body of the user to obtain non-invasive measurements from the user.

The electronic device 110 may include a sensor 130 or sensor array 120 that may be integrated into the electronic device 110. In another example, the sensor 130 or the sensor array 120 may be coupled to the processing device 150 of the electronic device 110. In one example, the sensor 130 may be a physiological sensor. The physiological sensor may include an impedance sensor, an optical sensor, an electrocardiography (ECG) sensor, a fluid level sensor, an oxygen saturation sensor, a body temperature sensor (skin temperature or core temperature), a plethysmographic sensor, a respiration sensor, a breath rate sensor, a cardiac sensor, a bio-impedance sensor, a spectrometer, a heart rate sensor, a blood pressure sensor, a pulse oximeter, or other physiological sensors. In another example, the sensor 130 may be a Newtonian sensor. The Newtonian sensor may include: a two-dimensional (2D) accelerometer, a three-dimensional (3D) accelerometer, a gyroscope, a magnetometer, a vibration sensor, a force sensor, a pedometer, a strain gauge, and so forth. In another example, the sensor 130 may be a location sensor. The location sensor may include: a global positioning system (GPS); a triangulation system; and so forth. In another example, the sensor 130 may be an environmental sensor. The environmental sensor may include: a humidity sensor, an ambient temperature sensor, an altitude sensor, a barometer, a weather sensor, and so forth. In one embodiment, the sensor 130 may be a non-invasive sensor. In one embodiment, one or more of the physiological sensors, the Newtonian sensors, or the environmental sensors may be integrated into the electronic device 110 or physically coupled to the electronic device 110. In another example, one or more of the physiological sensors, the Newtonian sensors, or the environmental sensors may be physically separate from the electronic device 110 and may communicate data with the electronic device, either directly or indirectly as discussed herein.

In one embodiment, the electronic device 110 may include a display 140 to show information to a user or a third party based on the measurements from the sensor 130 or the sensor array 120. In one embodiment, the display 140 can show the time, e.g., a clock. In another embodiment, the information shown on the display 140 may include measurement information, such as: a light backscatter measurement, a heart rate of a user, a breathing rate of the user, a blood pressure of the user, and so forth. In another example, the information shown on the display 140 may include recommendations, such as: a recommendation to take a break; a recommendation to go home; a recommendation to go to a hospital; or other recommendations. In another example, the information shown on the display 140 may include alerts, such as: an alert that a user may be experiencing a dehydration condition; an alert to take medication; an alert that an environment may not be safe; an alert that the user has fallen down; or other alerts. In another example, the information shown on the display 140 may include: hydration information, health status information, and other information.

In another embodiment, the display 140 can display information to a user or a third party based on information from other devices in communication with the electronic device 110. For example, the electronic device 110 can receive information from an automobile or a smart home device of a user or a third party. In this example, the information from the automobile or the smart home device may include ambient temperatures, humidity information, weather information, and so forth. The electronic device 110 can display the information from the automobile or the smart home device or use it in combination with measurements taken using the sensor 130 or the sensor array 120 to determine and display other information, such as a hydration level of the user.

In another embodiment, the processing logic of the electronic device 110 can determine an error with the sensor 130 or the sensor array 120 and display the error to the user or the third party using the display 140. For example, the processing logic can determine that the sensor 130 or the sensor array 120 is not interfacing with the user properly and the processing logic can use the display 140 to display an error message to the user. In one embodiment, the sensor 130 or the sensor array 120 is not interfacing with the user properly when the sensor 130 or the sensor array 120 is only partially contacting the body of the user or is not completely contacting the body of the user. In another embodiment, the sensor 130 or the sensor array 120 is not interfacing with the user properly when an object or particle is interfering with processing logic using the sensor 130 or the sensor array 120 to take physiological measurements of the user, environmental measurements, or other measurements. In one example, processing logic can determine that object or particle is interfering with taking measurements when measurement information is outside a defined measurement range or there is a discontinuity in the measurement information that exceeds a threshold level for the discontinuity. For example, when dirt comes between the sensor 130 or the sensor array 120 and the body of the user, the dirt can cause a discontinuity in the measurement information. When the processing logic determines the discontinuity in the measurement information, the processing logic can use the display 140 to display an error message associated with the discontinuity.

In another embodiment, the sensor 130 or the sensor array 120 is not interfacing with the user properly when the electronic device 110, the sensor 130, or the sensor array 120 has become dislocated or displaced. For example, measurements taken using the sensor 130 or the sensor array 120 with a first orientation can have a higher accuracy level than measurements taken using the sensor 130 or the sensor array 120 with a second orientation. In one example, the first orientation is an orientation where the user is wearing the electronic device 110 in a correct orientation and the second orientation is an orientation when the electronic device 110 has slipped or shifted to a different orientation. When the electronic device 110 has slipped or shifted the second orientation, the processing logic identifies that a measurement is outside a defined measurement range or there is a discontinuity in measurement information and uses the display 140 to display an error message associated with slippage or shifting.

In one example, the display 140 may be a touch screen display, such as a capacitive touch screen or a resistive touch screen. In another example, the display 140 can display a graphical user interface (GUI) to receive information. In another example, the electronic device 110 may include a data port 165, such as a universal serial bus (USB) port, a mini-USB port, a micro-USB port, a LIGHTNING® port, and so forth. In another example, the electronic device 110 may include a wireless communications device 170 (as discussed in the proceeding paragraphs) to send or receive information. The electronic device 110 may include a processor or processing device 150 to analyze or process measurements, received information, user input data, and/or other types of data.

In one example, the electronic device 110 can monitor stress on a respiratory system of the user. For example, the electronic device 110 can use the sensor 130, such as an oxygen saturation sensor, to monitor the stress on a respiratory system of the user.

In another example, the electronic device 110 can use one or more sensors 130 in the sensor array 120 to monitor stress on one or more systems of a user, such as a biological system or a body system. The biological system may include a respiratory system, a cardiovascular system, a nervous system, an integumentary system, a urinary system, an excretory system, a digestive system, an immune system, an endocrine system, a lymphatic system, a muscular system, a skeletal system, a reproductive system, and other systems. The body system may include two or more organs working together in the execution of a specific bodily function, e.g., a neuroendocrine system, a musculoskeletal system, and so forth. For example, the electronic device 110 can monitor stress on the cardiac system of a user using a blood pressure sensor of the sensor array 120 and can monitor the stress on the respiratory system of the user using an oxygen saturation sensor of the sensor array 120.

In another example, the electronic device 110 can monitor biological systems, organs, body parts, body system, or other areas of a user. In another example, the electronic device 110 can monitor or aggregate stress measurements from the sensors of the sensor array with other measurements, such as a lung capacity of a user, a hematocrit (HCT), an oxygen saturation level, and/or other medical measurements. In another example, the electronic device 110 can analyze the aggregated measurements to determine stress on one or more biological systems, organs, body parts, and/or body system and use the aggregated measurements to determine medical, health, and/or safety conditions.

In one example, the electronic device 110 can use the sensor array 120 to monitor a medical condition of a user, such as a cardiac condition, under various environments or conditions for continuous, semi-continuous, or a periodic period of time on a long-term or protracted basis. In one example, sensor measurements may be collected using the sensor 130 in the sensor array 120 of the electronic device 110. In another example, the sensor measurements may be stored on a non-tangible computer readable medium device 160 (e.g., a memory device) coupled to the electronic device 110 or in communication with the electronic device 110.

In one embodiment, the battery management system (BMS) 180 may include: one or more batteries (such as a rechargeable battery), a charger, and a management device. The one or more batteries may be located in the housing 115, in a band coupled to the housing, and so forth. The management device can manage and control power, e.g., power to and from the one or more batteries or regulate the power of the electronic device 110. For example, the management device can direct power received from an external power source, such as wall outlet, via the data port 165 (e.g., a USB port) and can recharge the one or more batteries. In another example, the BMS 180 may include a wireless power system with a wireless power coil to receive power. In this example, the management device can direct power received via the wireless power system to the one or more batteries. In another example, the management device can direct power to components or systems of the electronic device 110, such as the sensor array 120, the sensor 130, the display 140, the processing device 150, the memory device 160, and/or the communication device 170. In one example, the management device may be a processor or another processing device, independent of the processing device 150, that can manage and control the power. In another example, the management device may be software executed by the processing device 150 or processing logic to manage the power.

In one embodiment, the BMS 180 can determine when a charge level the one or more batteries are below a threshold amount and can send a notification to the user indicating that the electronic device 110 needs to be charged. In one example, the electronic device can send the notification to the user using a sensory device such as a vibrator, a speaker, a display, and so forth.

Figure 2:
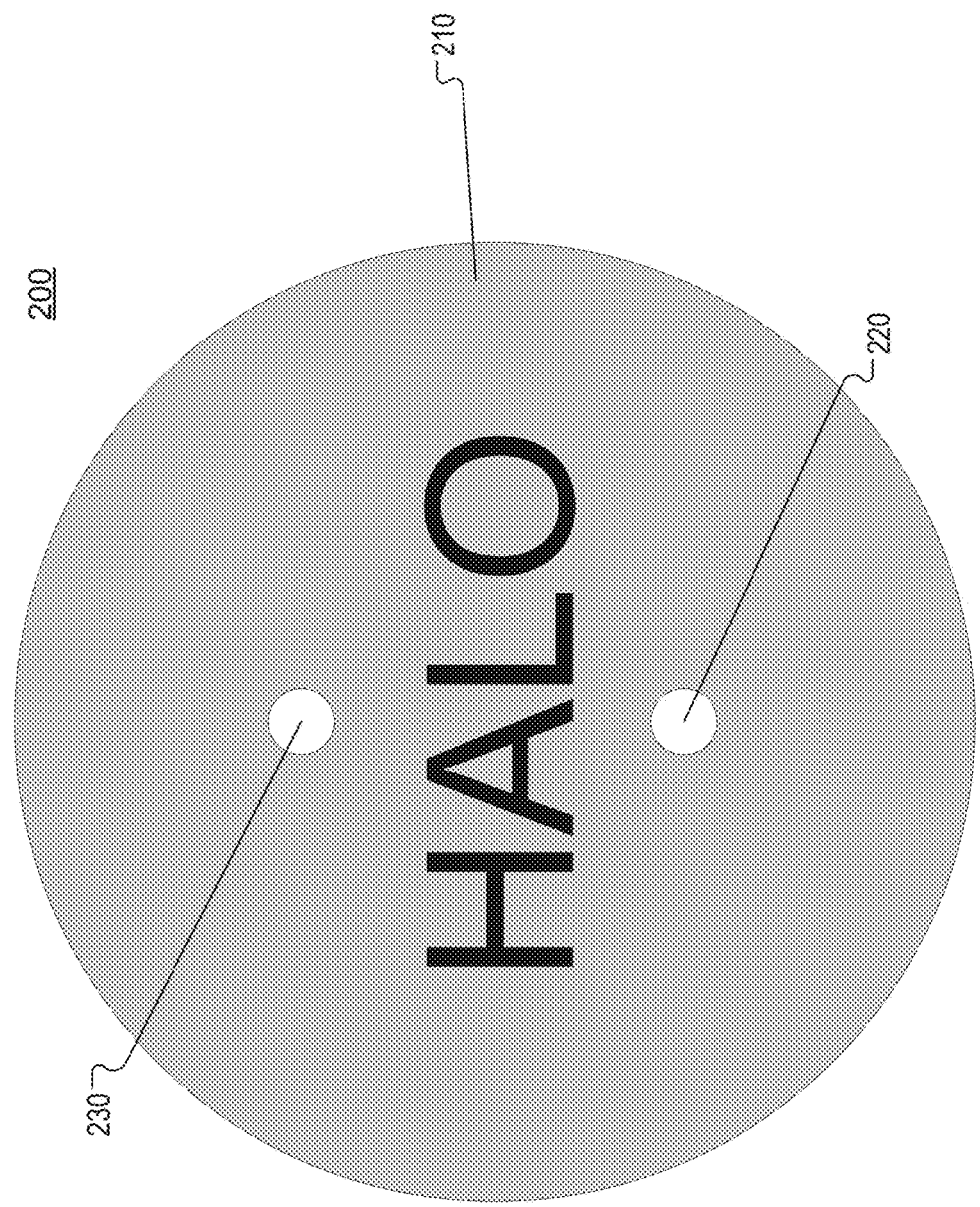
FIG. 2 illustrates a top view of an electronic device according to one embodiment.

FIG. 2 illustrates a top view of an electronic device 200 according to one embodiment. The electronic device 200 may have a top wall 202 that includes a display 210 on the exterior surface of the top wall 202. The top wall 202 may have a perimeter 204. The display 210 may provide information to a user such as indicating the user's hydration condition, temporal information such as the user's hydration condition over time, a time and date, and any information about a user's physiological state. In one embodiment, the display 210 may be a graphical user interface (GUI) that allows a user to interact with the device. In another embodiment, the display may be located on an external device, such as a cellular telephone, a personal computer, or other mobile devices. The electronic device 200 may further include a power and charging indicator 220 to indicate a state of the electronic device 200. In another embodiment, the electronic device 200 may include one or more ports such as a humidity, air flow, and/or temperature sensor port 230. In another embodiment, the electronic device 200 may include one or more sensors such as humidity, air flow, and/or temperature sensors which may be located on the surface (e.g., exterior surface of a perimeter wall, top wall 202, or bottom wall, and so forth) of the electronic device 200 or inside the humidity, air flow, and/or temperature sensor port 230. In one embodiment, a humidity sensor may detect the humidity level of the user's environment or a sweat rate of a user. A temperature sensor may detect the temperature of the user's environment or a surface temperature of a user. An air flow sensor may detect one or more measurements (e.g., first and second pressure measurements, first and second temperature measurements, and so forth) from which the air flow rate of the user's environment may be calculated.

Figure 3:
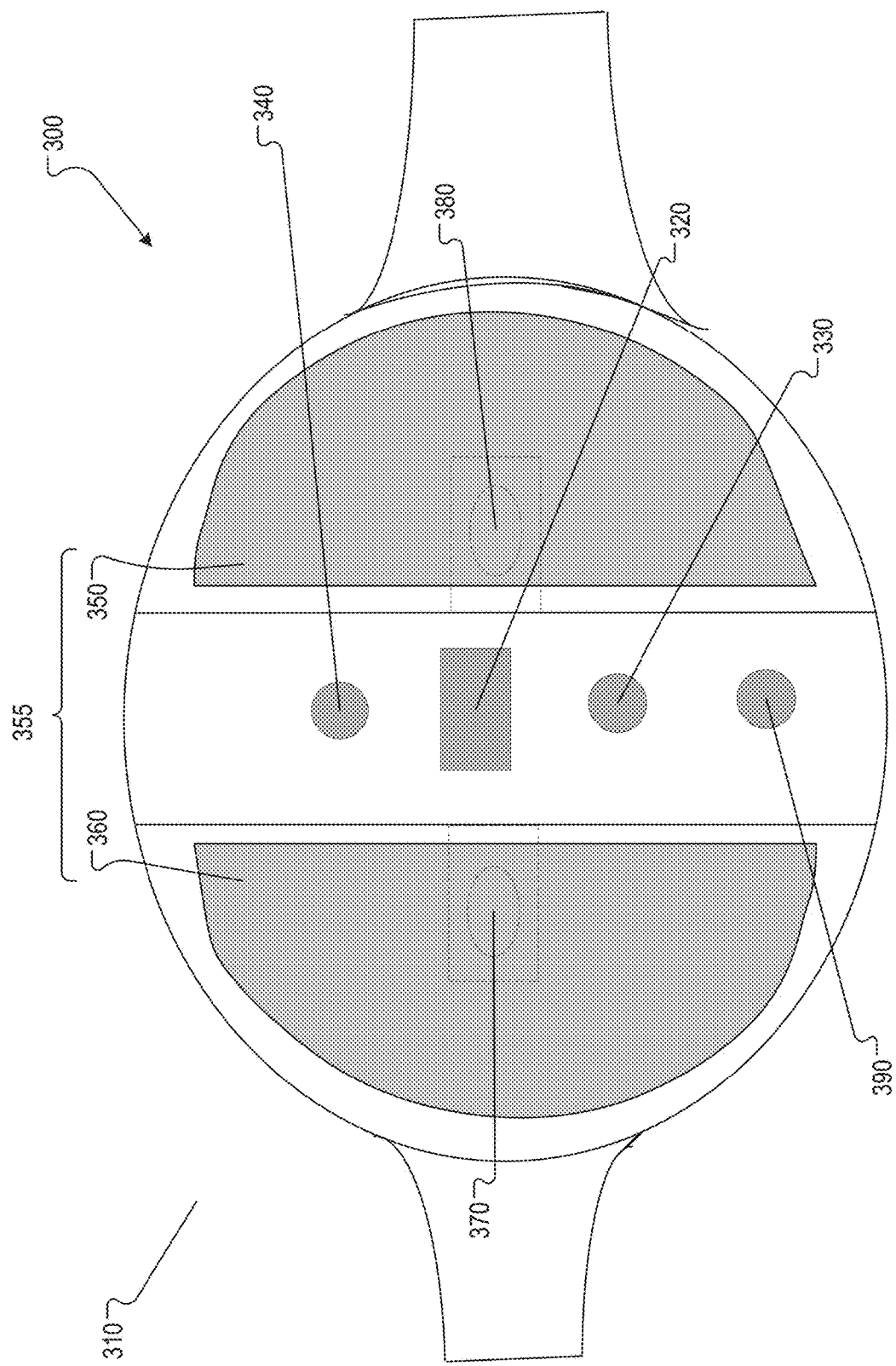
FIG. 3 illustrates a bottom view of an electronic device according to one embodiment.

FIG. 3 illustrates a bottom view of an electronic device 300 according to one embodiment. The electronic device 300 includes a housing 310, an optical sensor 320, light sources 330 and 340, an impedance sensor having impedance pads or contact terminals 350 and 360, contact wings 370 and 380, and one or more ports such as a humidity, air flow, and/or temperature sensor port 390. The port 390 may be an inlet to a flume.

The housing 310 of the electronic device 300 may have a bottom wall that has a perimeter. A perimeter wall may be disposed around the perimeter of the housing 310. The perimeter wall may be disposed between the bottom wall and the top wall. The top wall, bottom wall, and the perimeter wall may form an inner cavity. The housing 310 may be cylindrical.

The housing 310 of the electronic device 300 may be shaped to affix to the wrist, head, arm, chest, leg, ankle, earlobe, fingertip, or another surface of the body to determine a hydration condition of the body. In one embodiment, one or more components of the electronic device 300 may be located adjacent or pass through a wall (e.g., the bottom wall, perimeter wall, top wall, and so forth) of housing 310. The sensor components such as the optical sensor 320, light sources 330 and 340, impedance pads 350 and 360, and one or more ports such as a humidity, air flow, and/or temperature sensor port 390 may pass through the bottom wall of the housing 310 of the electronic device 300. In another embodiment, the underside of the housing 310 may be defined by a plane and one or more of the sensor components may sit flush with the plane such that when affixed to a user, the sensor components contact the skin of the user without extending beyond the plane. In another embodiment, the underside of the housing 310 may be defined by a plane and one or more of the sensor components may extend beyond the plane such that when affixed to a user, the sensor components contact the skin of the user and cause a slight indentation in the skin of the user by extending beyond the plane.

In one embodiment, the electronic device 300 includes one or more ports such as a humidity, air flow, and/or temperature sensor port 390. In one example, the humidity and/or temperature sensors in the humidity and/or temperature sensor port 390 may perform measurements to determine an amount the body is perspiring. In another example, the humidity and/or temperature sensors in the humidity and/or temperature sensor port 390 may perform a surface temperature measurement of the skin. In one example, a first humidity measurement and a first temperature measurement of an individual may be measured. A first vapor pressure measurement of the individual may be calculated from the first humidity measurement and the first temperature measurement. A second humidity measurement and a second temperature measurement of an individual may be measured. A second vapor pressure measurement of the individual may be calculated from the second humidity measurement and the second temperature measurement. The individual's sweat rate may be determined from the first vapor pressure measurement and the second vapor pressure measurement.

The humidity, air flow, and/or temperature sensors may perform measurements to determine an adjusted hydration condition. An air flow measurement may be determined from one or more measurements (e.g., first and second pressure measurements, first and second temperature measurements, and so forth) of the air flow sensor. An ambient temperature may be measured by an ambient temperature sensor. An ambient humidity may be measured by an ambient humidity sensor. A skin temperature may be measured by a temperature sensor. An ambient condition may be determined from the ambient temperature, the ambient humidity, and the air flow measurements. An adjusted hydration condition may be determined in view of the ambient condition, the skin temperature, and one or more physiological measurements.

FIG. 4 illustrates a block diagram of an electronic device 400 according to one embodiment. The electronic device 400 may include a power source 402, a processing device 404, a sensor interface unit 406, a data analysis unit 408, a data storage unit 410, a data communication unit 412, a graphical user interface 414, and a time reference unit 416.

In one embodiment, the electronic device 400 includes a power unit 402 that supplies power to components of the electronic device 400. The power unit 402 may include a battery to supply power and a charging unit that charges the battery. Alternatively, electronic device 400 is connectable to an energy source that powers the electronic device 400. In one embodiment, a charger may be used to recharge a battery or other energy source of the power unit 402. In one embodiment, an external battery (e.g., located in the band, and so forth) is coupled to the power unit 402.

In one embodiment, the electronic device 400 includes a processing device 404. The processing device 404 may include a central processor to process the data and/or information of the other components that include the electronic device 400 or other units, interfaces, and/or devices attached to or in communication with the electronic device 400.

In another embodiment, the electronic device 400 may include a sensor interface unit 406. The sensor interface unit 406 may be coupled to one or more sensors, such as the optical sensor, the impedance sensor, or the humidity and/or temperature sensors, and may perform one or more measurements relating to a physiological condition of a body using one or more of the sensors. In one embodiment, the sensor interface 406 and the processing device 404 may be the same component. In another embodiment, the sensor interface 406 may be coupled to the processing device 404. The sensor interface 406 can use the one or more sensors to take measurements relating to a hydration condition of a body, an impedance measurement, a backscatter measurement, a temperature measurement of a body or of an environment, a sweat rate measurement, a humidity measurement of a body or of an environment, an air flow measurement (e.g., temperature measurements, pressure measurements, and so forth) of the environment, or another physiological state or environment condition measurement. In one example, the sensor interface 406 may be coupled to the processing device 404 and the sweat rate, ambient humidity, air flow, skin temperature, and/or ambient temperature sensors. In this example, the sensor interface 406 may receive data from the sweat rate, ambient humidity, air flow, skin temperature, and/or ambient temperature sensors relating to the sweat rate, ambient humidity, air flow, skin temperature, and ambient temperature at the location of the electronic device 400.

In one example, the sensor interface 406 may be communicatively coupled to the processing device 404 and the optical sensor. In this example, the sensor interface unit 406 may receive data from the optical sensor relating to a portion of light that was reflected off an artery or another muscular-walled tube. Alternatively, the sensor interface 406 and the processing device 404 may be the same component. The sensor interface unit 406 may measure the backscatter of one or more wavelengths that have been reflected off a vein, artery, or other muscular-walled tube using the portion of light. In one example, the sensor interface 406 may be communicatively coupled to the processing device 404 and the impedance sensor. In this example, the sensor interface 406 may receive data from the impedance sensor relating to the detection portion of an electric current. In one example, the sensor interface 406 may be communicatively coupled to the processing device 404 and a first humidity sensor, a second humidity sensor, a first temperature sensor, and a second temperature sensor. In this example, the sensor interface 406 may receive data from the humidity and temperature sensors relating to the humidity and temperature of the user at the location of the electronic device 400.

In another embodiment, the electronic device 400 may include a time reference unit 416 that generates time reference data usable to control the time at which data is collected from the sensor interface unit 406. The time reference unit 416 may also be used to calculate spatial and/or temporal derivatives between information received from the sensor interface unit 406. In one embodiment of the disclosure, the time reference unit 416 may keep track of the calendar time, such as a clock. Alternatively, the time reference unit 416 may act as a timer, keeping track of a lapsed time or decrementing from a defined time to zero. The timer of the time reference unit 416 may be used to collect information or data from the sensor interface 406 for a defined period of time or to record how long the sensor interface 406 collects data.

In another embodiment, the electronic device 400 includes a data analysis unit 408. The data analysis unit 408 may be communicatively coupled to the processing device 404, sensor interface unit 406, time reference unit 416, and other components of the electronic device 400. The data analysis unit 408 may determine that a hydration condition has changed for a user by comparing temporal data from the time reference unit 416 to measurement data from the sensor interface unit 406. The data analysis unit 408 may communicate the hydration condition to a user through the graphical user interface (GUI) 414.

In another embodiment, the electronic device 400 includes a GUI 414. The graphical user interface may be a monitor screen, liquid crystal display (LCD), light-emitting diode (LED) display, or the like. In another embodiment, the GUI may present information such as a hydration condition to the user. In another embodiment, the user may be able to interact with the electronic device through inputs or icons on the GUI.

Figure 5A:
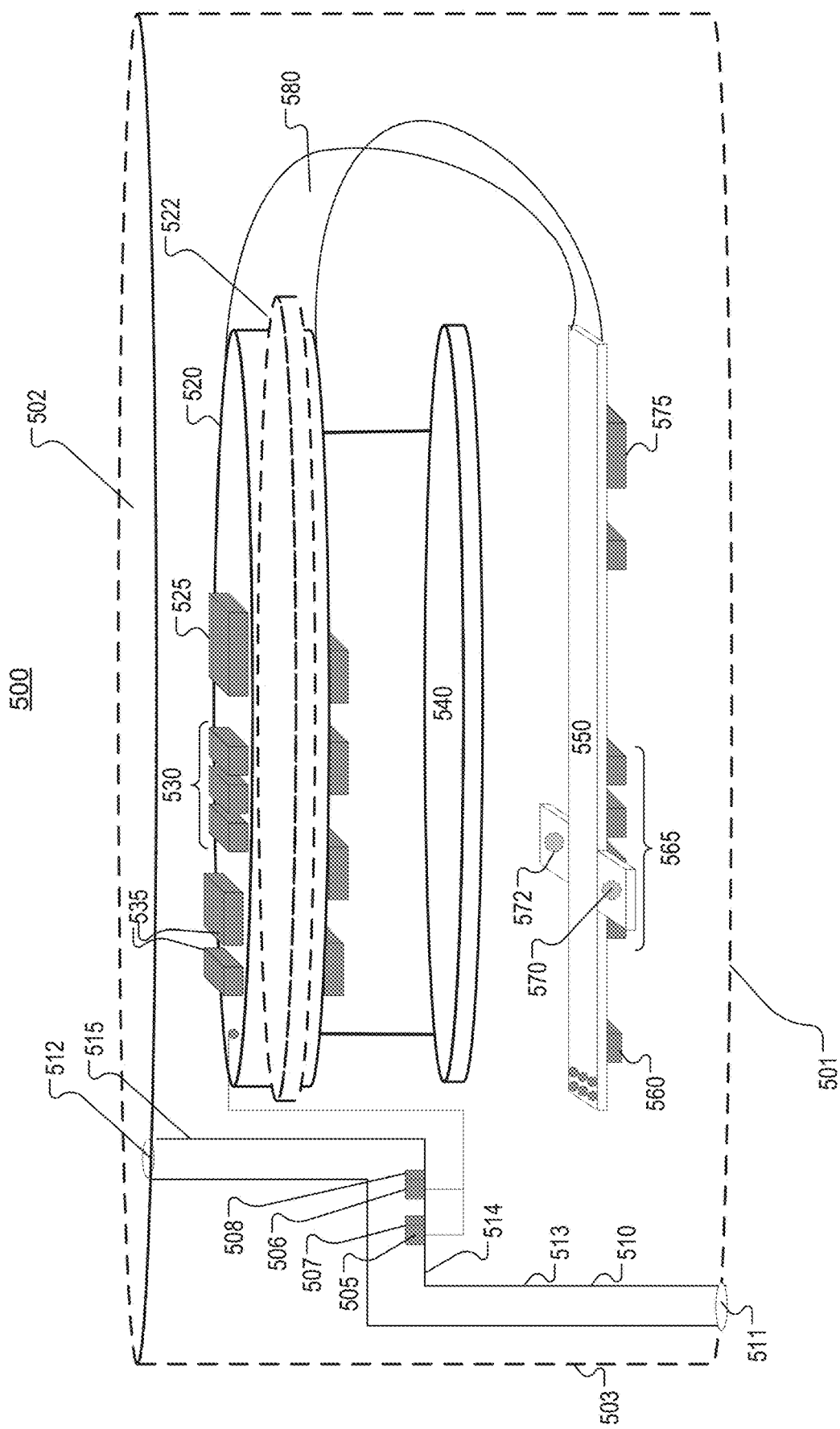
FIG. 5A illustrates an interior view of an electronic device according to one embodiment.

FIG. 5A illustrates an interior view of an electronic device 500 according to one embodiment. The electronic device 500 may be in the form of a cylinder, a polyhedron, a tetrahedron, a hexahedron (e.g., cube, parallelepiped, rectangular prism, and so forth), an octagonal prism, an ellipsoid, or some other shape. The electronic device 500 may include a bottom wall 501, a top wall 502, and a perimeter wall 503. A wall (e.g., bottom wall 501, top wall 502, perimeter wall 503, and so forth) of the housing may be a barrier, a layer, a composite, an area, and so forth. The perimeter wall 503 may be disposed around a perimeter of the electronic device 500 between the top wall 502 and the bottom wall 501. The top wall 502, the bottom wall 501, and the perimeter wall 503 may form an inner cavity. The exterior side of the bottom wall 501 may be shaped to affix to a user. For example, the exterior side of the bottom wall 501 may contact a body surface of the user. The top wall 502 may be opposite the exterior side of the bottom wall 501. In one example, the exterior side of the top wall 502 may face away from the body surface of the user and not directly contact the user when affixed to the user.

In one embodiment, the electronic device 500 may have a circuit board that includes a first portion 550, a second portion 570, a third portion 572, and a fourth portion 520. The circuit board may flip up or curl up adjacent to the flume 510 or perimeter wall 503 if it is too long to fit along the interior surface of the bottom wall 501. The first portion 550 may be a sensor board. The first portion 550 may be disposed adjacent the bottom wall 501. The second portion 570 may be a first contact wing 570. The third portion may be a second contact wing 572. The fourth portion 520 may be a main circuit board. The fourth portion may be located adjacent the top wall 502. In one embodiment, the sensor board 550 may be a flexible circuit board. In another embodiment, the main circuit board 525 may be a printed circuit board (PCB) on a substrate, such as a fiberglass or glass-reinforced plastic substrate with copper traces. The contact wings 570 and 572 may be foldable or flexible. The sensor board 550 may be coupled to the main circuit board 520 by a flexible connector 580. One or more components may be coupled to the sensor board 550. The components may include a vibrator 560, contact wings 570 and 572 (e.g., impedance sensor contacts, and so forth), optical components 565 (e.g., optical sensor, first light source, second light source, and so forth), and a thermistor 575. In one embodiment, the vibrator 560 may be activated to inform the user when a hydration condition has changed or to provide additional information to the user. The main PCB 520 may have double sided mounting and may include a motion processing unit (MPU) 525, display light emitting diodes (LEDs) or graphical user interface (GUI) 530, one or more communication components 535, such as a personal area network component (e.g., BLUETOOTH® Low Energy (BLE) component, cellular antenna, and so forth), an induction coil 522, and so forth. The components on the flexible circuit board may be layered. In one embodiment, the MPU 525 may detect movement of the electronic device and relay motion information to the sensor interface unit 506 (FIG. 4). Additionally, the display LEDs or the GUI 530 may be used to inform the user of a hydration condition. The communication components 535 may be located on the main PCB 525 to reduce or eliminate interference.

The LEDs may be located adjacent to the top wall 502. A portion of the top wall 502 may include a light diffusing material. The light diffusing material and LEDs 530 may provide backlighting. The processing device 404 (FIG. 4) may turn on the LEDs 530 in response to an activation event. The activation event may include tapping the top wall 502 to wake up the electronic device 500, raising the electronic device 500 (e.g., raising the electronic device 500 up to the face of the user, and so forth), tilting the electronic device 500 (e.g., tilting the electronic device 500 towards the eyes of the user, and so forth).

In one embodiment, the electronic device 500 may include a flume 510. The flume 510 may be different geometries. For example, the flume 510 may be an s-shape. For example, the flume 510 may include a first portion 513 extending from a first opening 511 at the bottom wall 501 along a first axis that is parallel to the perimeter wall 503 of the electronic device 500. The flume 510 may include a second portion 514 that is connected to a first portion 513. The second portion 514 extends along a second axis that is at a defined angle from the first axis. In one example, the defined angle is approximately 90 degrees. The second portion 514 may include humidity sensors 505 and 506 and temperature sensors 507 and 508. In one embodiment, the sensors 505, 506, 507, and 508 may be located on the second portion 514. An advantage of the sensors 505, 506, 507, and 508 being located at the second portion 514 may decrease the amount of outside influences on the measurements.

The outside influences may include interference from ambient temperatures, humidity, or an air flow that is exterior to the device. In one example, the temperature, the humidity, or the air flow that is exterior to the device may be an outdoor temperature, humidity, or air flow. In another example, the temperature, the humidity, or the air flow that is exterior to the device may be an indoor temperature, humidity, or air flow that enters the flume 510 when the user is moving.

The second portion 514 should be long enough to allow locating the humidity sensors 505 and 506 far enough apart to measure a change in humidity and to allow locating the temperature sensors 507 and 508 far enough apart to measure a change in temperature to then be able to measure a change in vapor pressure from the change in humidity and change in temperature. The sensitivity of the humidity sensors 505 and 506 may determine how far apart the sensors 505 and 506 need to be to be able to measure a difference in humidity. For example, the more sensitive the humidity sensors 505 and 506 are, the closer the humidity sensors 505 and 506 may be located and still measure a difference in humidity. The sensors should be close enough together to minimize the size of the flume and the electric device 500.

The flume 510 may include a third portion 515 that is connected to the second portion 514. The third portion 515 extends along a third axis that is parallel to the first axis. The third portion 515 extends to a second opening 512 at the top wall 502. The flume may be insulated to avoid interference of the sensors inside the flume from heat from the electronics in the electronic device 500, environmental temperature, and so forth. The flume may reduce and/or remove condensation from the flume. In one embodiment, the flume may reduce condensation by insulating the flume from ambient temperature (e.g., insulate from cold outside temperature). In another embodiment, the flume may reduce condensation by heating a portion of the flume 510 proximate the second opening 512 (e.g., not insulating the portion of the flume 510 proximate the second opening 512 from heat from electronics inside the electronic device 500). In another embodiment, the flume may remove condensation by having a lining that wicks the condensation to the exterior of the electronic device 500. In another embodiment, the flume may remove condensation by a condensation pathway to the exterior of the electronic device 500. In another embodiment, the flume may remove condensation capturing and reheating the condensation so that it leaves the electronic device 500 as vapor.

In another embodiment, the flume 510 may be at least one of inclined or u-shaped. The flume may extend from a first opening 511 at the bottom wall 501 to a second opening 512 at the top wall 502. The flume 510 may extend from the bottom wall 501 to the top wall 502. A membrane may be disposed proximate the first opening 511 and/or the second opening 512 to filter fluid and dirt particles, as discussed in greater detail in the proceeding paragraphs.

The flume 510 may allow humidity and/or temperature sensors 505 to measure the humidity and/or temperature proximate the skin of the user. For example, heat is radiated from the skin of the user, the heat goes up the flume 510, temperature sensor 507 takes a first temperature measurement, and temperature sensor 508 takes a second temperature measurement. In another example, as sweat evaporates from the skin of a user, the air proximate the skin of the user will have a humidity level due to the sweat evaporating from the skin as vapor. The vapor will enter the flume 510 at the first opening 511 in the bottom wall 501, humidity sensor 505 will take a first humidity measurement and humidity sensor 506 will take a second humidity measurement, and the vapor can exit the second opening 512 in the top wall 502. Humidity sensor 505 and temperature sensor 507 may be a single sensor. Humidity sensor 506 and temperature sensor 508 may be a single sensor.

In one embodiment, the electronic device 500 may have an ambient humidity sensor integrated proximate the top wall 502. In one embodiment, the ambient humidity sensor is the same as the humidity sensor 505 or 506. In another embodiment, the ambient humidity sensor may measure an environmental humidity that is not caused by vapor from the sweat evaporating from the skin of the user. The electronic device 500 may have an air flow sensor integrated into the top wall 502 or perimeter wall 503 of the electronic device. In one embodiment, the air flow sensor may include a first heating element and a second heating element. In one embodiment, the air flow sensor may include a pressure sensor (e.g., a pitot tube, a venturi tube, venturi pump, and so forth). The electronic device 500 may have a skin temperature sensor (e.g., thermistor, thermocouple, and so forth) integrated into the bottom wall 501. In one embodiment the skin temperature sensor may be the temperature sensor 507 or 508. The electronic device 500 may have an ambient temperature sensor located proximate the top wall 502. The ambient temperature sensor may measure an environmental temperature that is not radiating from the body. The ambient humidity sensor, ambient temperature sensor, air flow sensor, and so forth may be located in one or more flumes, recesses, cavities, and so forth.

In one embodiment, one or more sensors (e.g., impedance sensors, optical sensors, humidity sensors, temperature sensors, ambient temperature sensor, ambient humidity sensor, air flow sensor, skin temperature sensor, and so forth) may be coupled to a sensor interface unit 406 (FIG. 4). The sensor interface unit 406 (FIG. 4) may make an ambient humidity measurement using an ambient humidity sensor, one or more measurements using an air flow sensor (e.g., first and second temperature measurements, first and second pressure measurements, and so forth), a skin temperature measurement using a skin temperature sensor, an ambient temperature measurement using an ambient temperature sensor, an impedance measurement using impedance sensors, a vapor measurement using a humidity sensor and temperature sensor, and/or an amount of a wavelength of light measurement using an optical sensor.

In one embodiment, the electronic device 500 may include an information interface to receive user information from an input device such as GUI 530, or an external device such as a smartphone, a computer, and so forth. The user information may include demographic or personal information of a user including one or more of: a height of the user, a weight of the user, a gender of the user, a past hydration condition, a past event, and so forth. The processing device 404 (FIG. 4) may be coupled to the sensor interface unit 406 (FIG. 4) and the information interface.

Figure 5B:
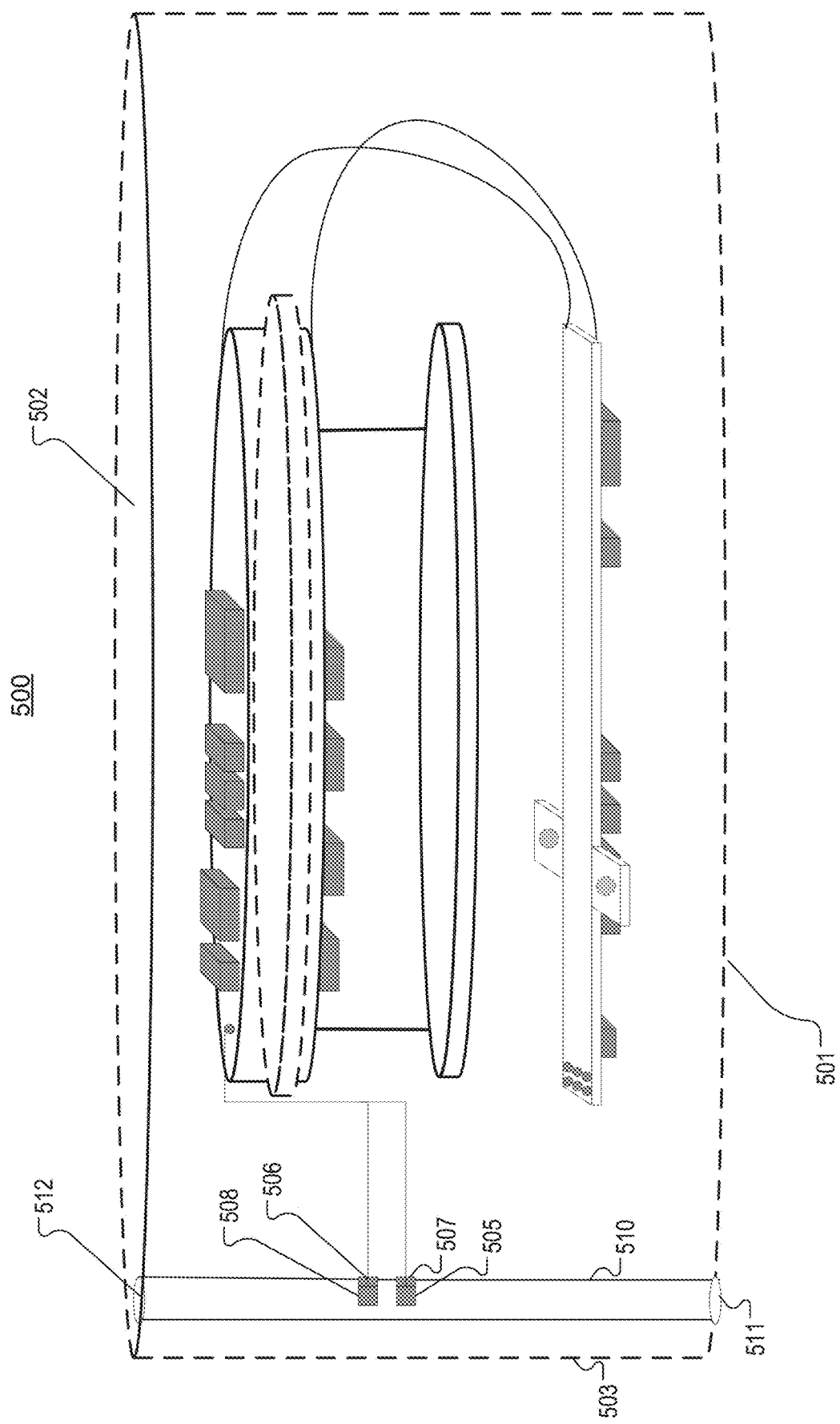
FIG. 5B illustrates an interior view of the electronic device according to another embodiment.

FIG. 5B illustrates an interior view of the electronic device 500 according to another embodiment. Some components of the electronic device 500 of FIG. 5B are similar to some components of the electronic device 500 of FIG. 5A as noted by similar reference numbers unless expressly described otherwise. In one embodiment, the electronic device 500 may have a flume 510 that is straight. For example, the entire length of the flume 510 from the first opening 511 at the bottom wall 501 to the second opening 512 at the top wall 502 may be substantially parallel with the perimeter wall 503. Humidity sensors 505 and 506 and temperature sensors 507 and 508 may be located in the flume 510. The sensors 505, 506, 507, and 508 should be located far enough away from the top wall 502 to decrease the amount of outside influences on the measurements.

The outside influences may include interference from the outdoor temperature, outdoor humidity, and outdoor air flow. The sensors 505, 506, 507, and 508 may be located far enough away from the bottom wall 501 to decrease the amount of other influences on the measurements such as conductive heat transfer from the skin, sweat buildup on the skin, condensation at the bottom of the flume 510, and so forth. The flume 510 should be long enough to allow locating the humidity sensors 505 and 506 and the temperature sensors 507 and 508 far enough apart to measure a change in humidity and a change in temperature. The sensors should be far enough apart to be able to measure a change in vapor pressure from the change in humidity and change in temperature without outside and other influences. The sensors should be close enough together to minimize the size of the flume and the electric device 500. A membrane may be disposed at the first opening 511 and/or the second opening 512 to filter fluid and dirt particles.

Figure 6A:
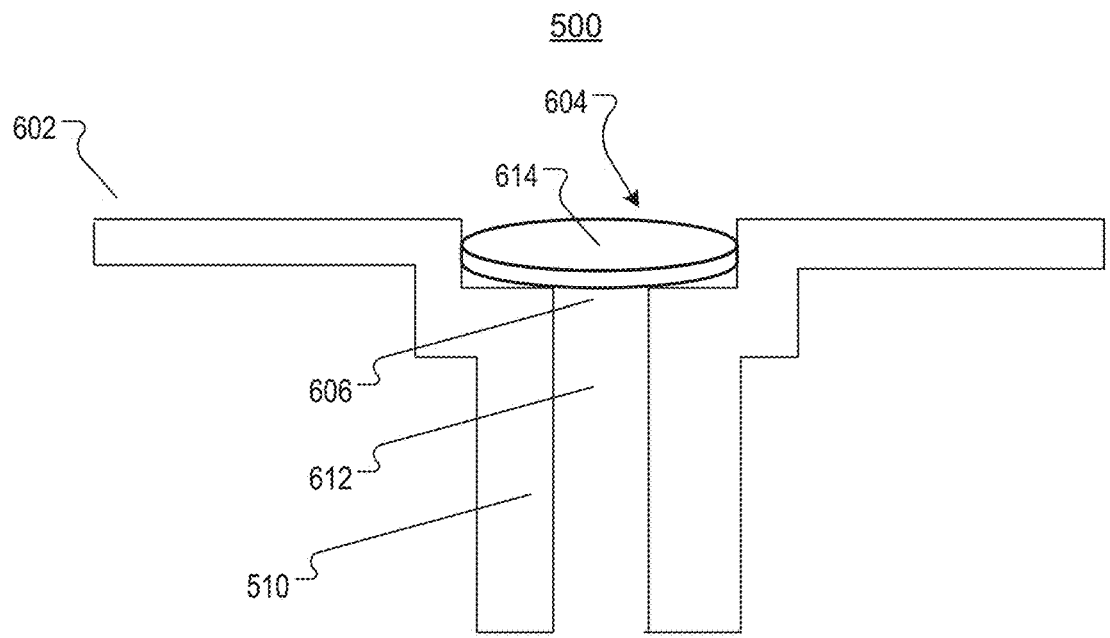
FIG. 6A illustrates a cross-sectional view of a flume of an electronic device according to one embodiment.

FIG. 6A illustrates a cross-sectional view of a flume 510 of an electronic device 500 according to one embodiment. Some components of the electronic device 500 of FIG. 6A are similar to some components of the electronic device 500 of FIGS. 5A and 5B as noted by similar reference numbers unless expressly described otherwise. The electronic device 500 may include a recess 604 in a wall 602 (e.g., perimeter wall 503, top wall 502, bottom wall 501, and so forth). The recess 604 may have an opening 606 (e.g., first opening 511, second opening 512, and so forth). In one embodiment, the electronic device 500 may have a flume 510 with a first end 612 disposed proximate the opening 606. The opening 606 may have a smaller cross-sectional area than the recess 604. The opening 606 may have substantially the same cross-sectional area as the flume 510. A membrane 614 may be disposed in the recess 604 in the wall 602 at the first end 612 of the flume 510.

The membrane may include one or more materials including a semipermeable membrane, GORE-TEX®, hydrophobic filter material, expanded polytetrafluoroethylene (ePTFE), and so forth. The membrane 614 may be substantially coplanar with the external surface of the wall 602. The membrane 614 may have pores that are smaller than liquid droplets (e.g., water, sweat, and so forth) and solid particles (e.g., dirt, sand, and so forth) to prevent fluid and solid particles from entering the flume 510. In one embodiment, the membrane 614 may have nine billion pores per square inch, each pore being 20,000 times smaller than a water droplet, but large enough to allow vapor to pass through. The membrane 614 may allow at least one of vapor, air flow, and heat to exit the flume 510. The membrane 614 may allow at least one of vapor, air flow, and heat to enter the flume 510. The membrane may allow vapor and air to pass through to the flume 510 so that humidity and temperature measurements may be taken by the humidity sensors 505 and 506 and temperature sensors 507 and 508 in FIGS. 5A and 5B to calculate vapor pressure measurements.

In one embodiment, the electronic device 500 may be substantially waterproof, water resistant, hermetically sealed, or in some other way protect the components from moisture damage. In one embodiment, each flume 510 of the electronic device 500 may include a membrane 614 to hermetically seal the flume 510 so that fluid cannot enter the housing 501. The electronic device 500 may be hermetically sealed, having no physical external ports that are not hermetically sealed. In one embodiment, one or more components of the electronic device 500 may have a component coating (e.g., nano-film, and so forth). In one embodiment, gaskets (e.g., o-rings, rubber seals, molded shapes, custom sealing devices, and so forth) and/or other components (e.g., epoxy, and so forth) may be used to seal openings into the electronic device 500. In one embodiment, the electronic device 500 does not have external data ports. The flexible circuit board may be flashed with a wireless area network protocol (e.g., BLE protocol, and so forth) before sealing the electronic device 500 so that the electronic device will not require the external data ports.

Figure 6B:
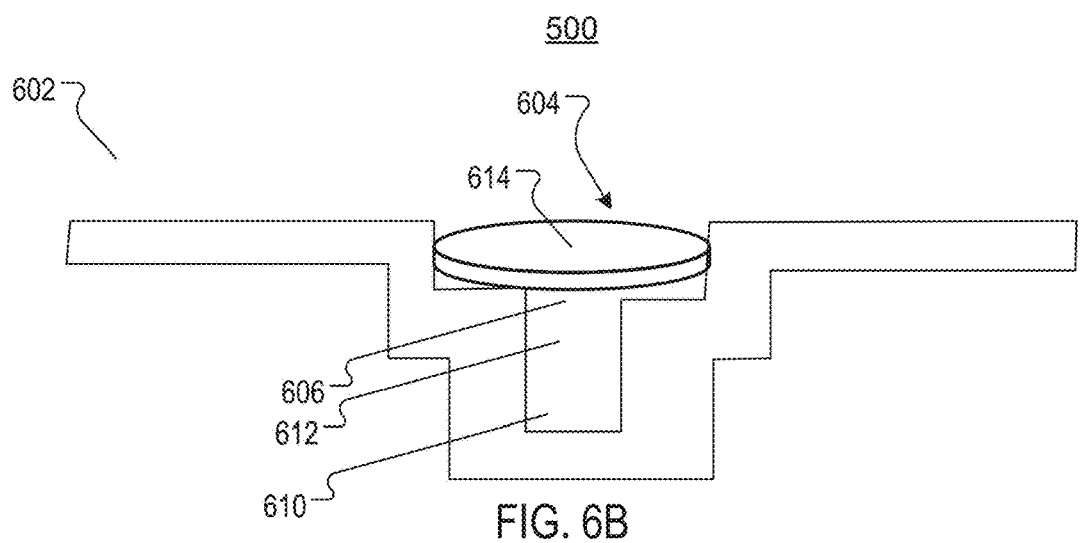
FIG. 6B illustrates a cross-sectional view of a cavity of an electronic device according to one embodiment.

FIG. 6B illustrates a cross-sectional view of a cavity 610 of an electronic device 500 according to one embodiment. Some components of the electronic device 500 of FIG. 6B are similar to some components of the electronic device 500 of FIG. 5A, 5B, or 6A or the electronic device of FIGS. 5A and 5B as noted by similar reference numbers unless expressly described otherwise. The electronic device 500 may include a recess 604 in a wall 602 (e.g., perimeter wall 503, top wall 502, bottom wall 501, and so forth). The recess 604 may have an opening 606. In one embodiment, the electronic device 500 may have a cavity 610 with a first end 612 disposed proximate the opening 606. The opening 606 may have a smaller cross-sectional area than the recess 604. The opening 606 may have substantially the same cross-sectional area as the cavity 610. A membrane 614 may be disposed in the recess 604 in the wall 602 at the first end 612 of the cavity 610. A sensor (e.g., ambient temperature sensor, ambient humidity sensor, air flow sensor, skin temperature sensor, and so forth) may be disposed in the cavity 610. In one embodiment the membrane 614 may have small pores (e.g., nine billion pores per square inch or a different amount of pores) that reduce or prevent air flow from entering the cavity 610. In another embodiment, the membrane 614 may have larger pores that allow air flow to enter the cavity 610.

Figure 6C:
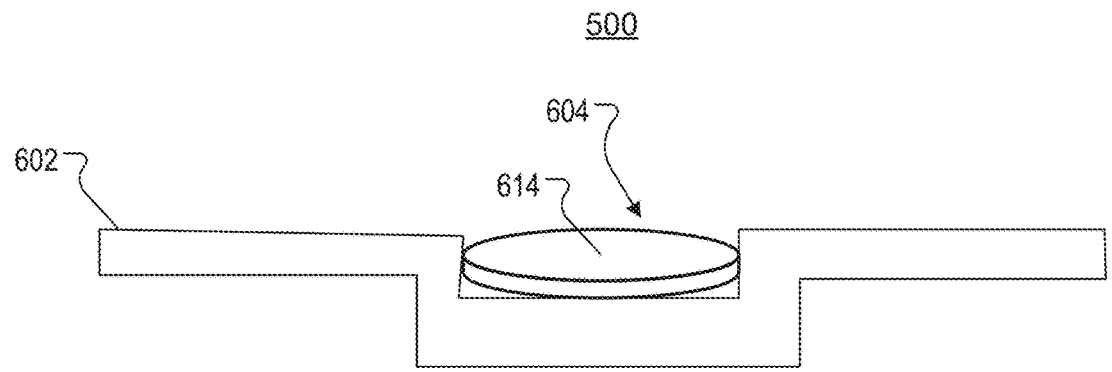
FIG. 6C illustrates a cross-sectional view of a recess in a wall of an electronic device according to one embodiment.

FIG. 6C illustrates a cross-sectional view of a recess 604 in a wall 602 of an electronic device 500 according to one embodiment. Some components of the electronic device 500 of FIG. 6C are similar to some components of the electronic device 500 of FIG. 5A, 5B, 6A, or 6B as noted by similar reference numbers unless expressly described otherwise. The electronic device 500 may include a recess 604 in a wall 602 (e.g., perimeter wall 503, top wall 502, bottom wall 501, and so forth). A membrane 614 may be disposed in the recess 604 in the wall 602. A sensor (e.g., ambient temperature sensor, ambient humidity sensor, air flow sensor, skin temperature sensor, and so forth) may be disposed in the recess 604, between the membrane 614 and the recess 604.

Figure 6D:
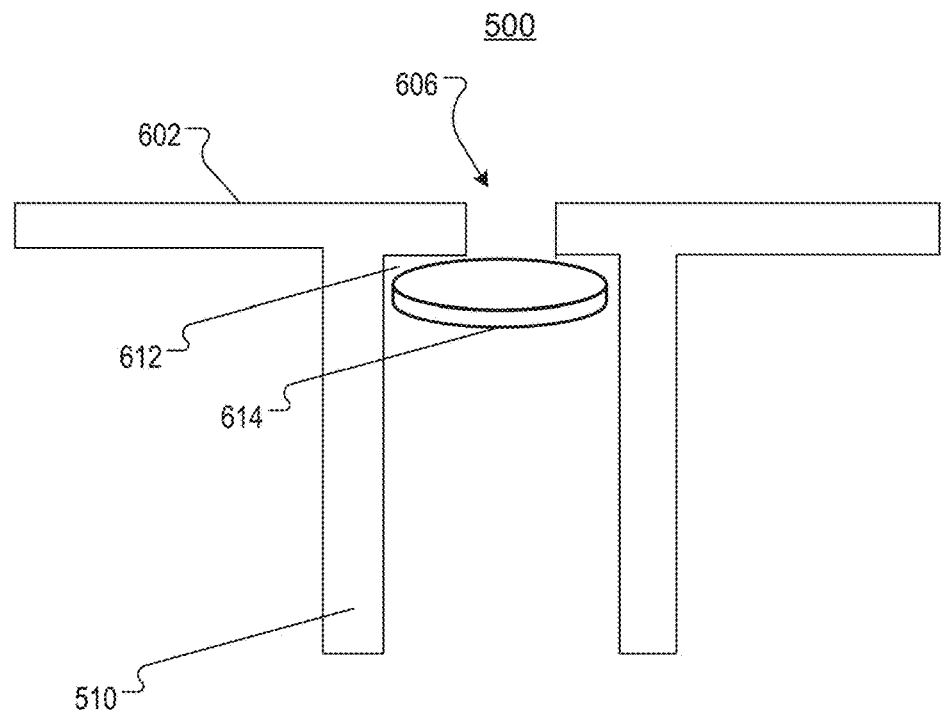
FIG. 6D illustrates a cross-sectional view of a flume of an electronic device according to one embodiment.

FIG. 6D illustrates a cross-sectional view of a flume 510 of an electronic device 500 according to one embodiment. Some components of the electronic device 500 of FIG. 6D are similar to some components of the electronic device 500 of FIG. 5A, 5B, 6A, 6B, or 6C as noted by similar reference numbers unless expressly described otherwise. The electronic device 500 may include an opening 606 (e.g., first opening 511, second opening 512, and so forth). In one embodiment, the electronic device 500 may have a flume 510 with a first end 612 disposed proximate the opening 606. The opening 606 may have a smaller cross-sectional area than the cross-sectional area of the flume 510. A membrane 614 may be disposed in the flume 510 proximate the opening 606 in the wall 602 at the first end 612 of the flume 510. Sensors may be disposed inside the flume 510 as described above.

Figure 6E:
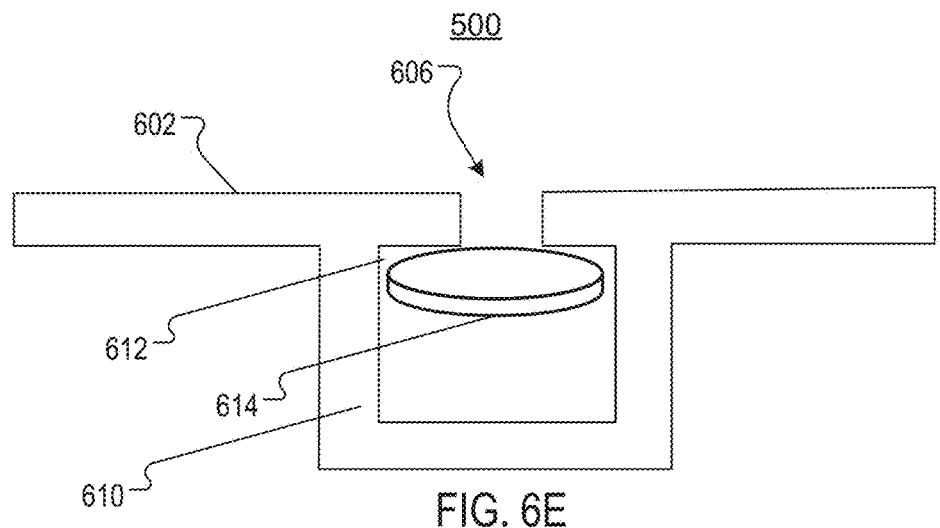
FIG. 6E illustrates a cross-sectional view of a cavity of an electronic device according to one embodiment.

FIG. 6E illustrates a cross-sectional view of a cavity 610 of an electronic device 500 according to one embodiment. Some components of the electronic device 500 of FIG. 6E are similar to some components of the electronic device 500 of FIG. 5A, 5B, 6A, 6B, 6C, or 6D as noted by similar reference numbers unless expressly described otherwise. The electronic device 500 may include a recess 604 in a wall 602 (e.g., perimeter wall 503, top wall 502, bottom wall 501, and so forth). The wall 602 may have an opening 606. In one embodiment, the electronic device 500 may have a cavity 610 with a first end 612 disposed proximate the opening 606. The opening 606 may have a smaller cross-sectional area than the cross-sectional area of the cavity 610. A membrane 614 may be disposed in the recess 604 in the wall 602 at the first end 612 of the cavity 610. One or more sensors may be disposed inside the cavity 610 as described above.

Figure 6F:
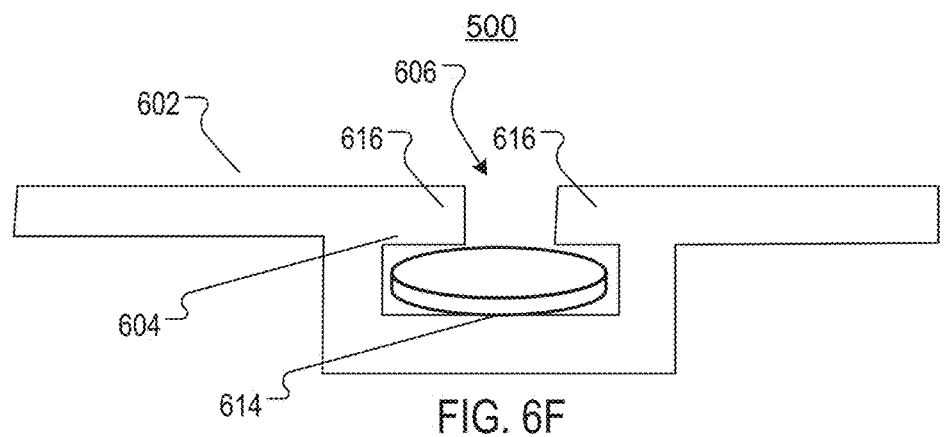
FIG. 6F illustrates a cross-sectional view of a recess in a wall of an electronic device 500 according to one embodiment.

FIG. 6F illustrates a cross-sectional view of a recess 604 in a wall 602 of an electronic device 500 according to one embodiment. Some components of the electronic device 500 of FIG. 6F are similar to some components of the electronic device 500 of FIG. 5A, 5B, 6A, 6B, 6C, 6D, or 6E as noted by similar reference numbers unless expressly described otherwise. The electronic device 500 may include an opening 606 in a wall 602 (e.g., perimeter wall 503, top wall 502, bottom wall 501, and so forth). The electronic device 500 may include a recess 604 in the wall 502. The recess 604 may have a larger cross-sectional area than the cross-sectional area of the opening 606 creating a lip 616. A membrane 614 may be disposed in the recess 604 between the recess 604 and the lip 616.

Figure 7:
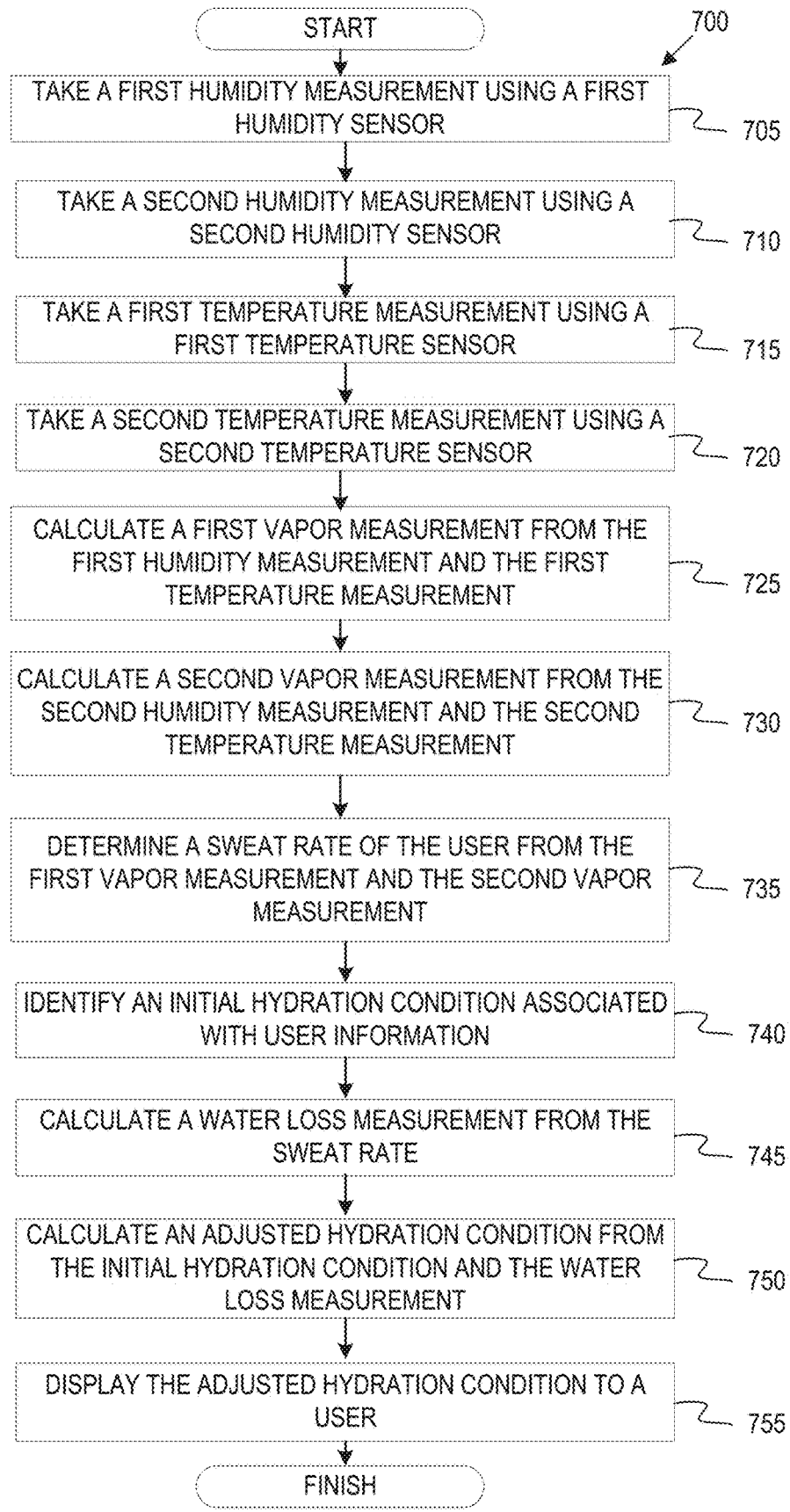
FIG. 7 illustrates a flow diagram of a method of determining a hydration condition according to one embodiment.

FIG. 7 illustrates a flow diagram of a method 700 of determining a hydration condition according to one embodiment. The method 700 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 700 may be performed, in part, by processing logic of processing device 404 (FIG. 4).

For simplicity of explanation, the method 700 is illustrated and described as a series of acts. However, acts in accordance with this disclosure can occur in various orders and/or concurrently and with other acts not presented as described herein. Furthermore, not all illustrated acts may be performed to implement the method 700 in accordance with the disclosed subject matter. In addition, those skilled in the art will understand and appreciate that the method 700 could alternatively be represented as a series of interrelated states via a state diagram or events.

The method may include, taking a first humidity measurement using a first humidity sensor (705). The first humidity measurement may be a relative humidity measurement of the air in the flume 510 (FIG. 5A or 5B) at a first location.

The method may include, taking a second humidity measurement using a second humidity sensor (710). The second humidity measurement may be a relative humidity measurement of the air in the flume 510 (FIG. 5A or 5B) at a second location. The second location may be a threshold distance or spacing from the first location.

The method may include, taking a first temperature measurement using a first temperature sensor (715). The first temperature measurement may be a dry bulb temperature measurement of the air in the flume 510 (FIG. 5A or 5B) at a first location. Dry bulb temperature may be a temperature of air measured by a sensor freely exposed to the air but shielded from radiation and moisture.

The method may include, taking a second temperature measurement using a second temperature sensor (720). The second temperature measurement may be a dry bulb temperature measurement of the air in the flume 510 (FIG. 5A or 5B) at a second location.

The method may include, calculating a first vapor pressure measurement from the first humidity measurement and the first temperature measurement (725). In one embodiment, the processing device 504 (FIG. 5A or 5B) may calculate a water vapor saturation pressure for the first temperature measurement. The processing device 504 (FIG. 5A or 5B) may use the equation $Pws = (e^{(77.3450 + 0.0057*T - 7235/T)})/(T^{8.2})$, where Pws is the water vapor saturation pressure (Pa), e is a constant 2.718, and T is the dry bulb temperature of the moist air (K). For example, if the temperature is 25 degrees Celsius (77 degrees Fahrenheit), the water vapor saturation pressure may be calculated at 3130 Pa (0.454 psi). In another embodiment, the processing device 404 (FIG. 4) may look up the water vapor saturation pressure in a database by the first temperature measurement. In another embodiment, the processing device 404 (FIG. 4) may calculate the first vapor pressure measurement directly from the first humidity measurement and the first temperature measurement. For example, the processing device 404 (FIG. 4) may calculate a first vapor pressure measurement by multiplying the water vapor saturation pressure (calculated using the first temperature measurement) by the first humidity measurement. For example, when the relative humidity is 50% and the water vapor saturation pressure is 3130 Pa at 25 degrees Celsius, the calculated first vapor pressure measurement is 1565 Pa.

The method may include, calculating a second vapor pressure measurement from the second humidity measurement and the second temperature measurement (730). The second vapor pressure measurement may be calculated in the same or similar manner or in a different manner as the first vapor pressure measurement.

The method may include, determining a sweat rate of the user from the first vapor pressure measurement and the second vapor pressure measurement (735). The processing device 404 (FIG. 4) may calculate the difference in time between the first vapor pressure measurement and the second vapor pressure measurements. The processing device 404 (FIG. 4) may obtain the difference in time from the time reference unit 416 (FIG. 4).

In one embodiment, the sweat rate may be a change in vapor pressure over time. The processing device 404 (FIG. 4) may calculate a change in vapor pressure rate at the flume by taking the difference between the first vapor pressure measurement and the second vapor pressure measurement and dividing by the difference in time.

In another embodiment, the sweat rate may be a mass flow rate. The processing device 404 (FIG. 4) may determine a first density of the air at the first vapor pressure measurement and a second density of the air at the second vapor pressure measurement. The density of air may be determined from a database given the vapor pressure of the air. The processing device 404 (FIG. 4) may determine a volume of the flume. The processing device 404 (FIG. 4) may calculate a change in mass flow rate by determining a change in density, multiplying by the volume, and dividing by the difference in time.

In another embodiment, the sweat rate may be a volume flow rate. In another embodiment, the sweat rate may be some other calculation or determination.

The processing device 404 (FIG. 4) may determine a sweat rate of the user from the sweat rate at the flume. The sweat rate at the flume may be the sweat rate measured in a defined size of flume of an electronic device located in a specific location on the user. In one embodiment, the processing device 404 (FIG. 4) may determine a ratio of sweat rate at the flume to the sweat rate of the user. The processing device 404 (FIG. 4) may use the sweat rate at the flume and the ratio of sweat rate at the flume to sweat rate of the user to determine the sweat rate of the user (e.g., entire body sweat rate, and so forth). For example, if the ratio of sweat rate at the flume to the sweat rate of the user were determined to be 0.01%, that sweat rate at the flume could be multiplied by 10,000 to calculate the total sweat rate.

The method may include, identifying an initial hydration condition associated with user information (740). In one embodiment, the user information may include one or more of a height of the user, a weight of the user, or a gender of the user. In another embodiment, the user information may also include one or more of medical history, cardiovascular condition, past measurements, activity level, or recent liquid intake. In another embodiment, the initial hydration condition may be a volume or weight of water in the user. In another embodiment, the volume or weight of water in the user may be limited to the interstitial fluid or tissue water in the skin tissue of the user. In another embodiment, the initial hydration condition may be obtained from a database that includes average hydration information for a user by weight, height, gender and/or other user information. In another embodiment, the initial hydration condition may be received from an input device. The input device could be a GUI or touchscreen display of the device, a smart phone, a weight scale, and so forth. In another embodiment, the initial hydration condition may be calculated from the user information. For example, given the user information, it may be determined that 60% of the weight of a user is body water, that ⅓ of the body water is extracellular fluid, and that ⅘ of the extracellular fluid is interstitial fluid. Therefore, it may be determined that 16% of the body weight of the user is interstitial fluid. The initial hydration condition may be determined to be 16% of the weight of the user or may be the water volume equivalent of 16% of the weight of the user.

The method may include, calculating a water loss measurement from the sweat rate (745). The processing device 404 (FIG. 4) may calculate a water loss measurement from the sweat rate of the user and a time measurement from the time reference unit 416 (FIG. 4). For example, if the total sweat rate is 1 liter per hour, it may be calculated that over the course of one hour, the user had one liter or one kilogram of water loss. The total water loss measurement may be a total volume of water loss, a total mass of water loss, or some other determination.

The method may include, calculating an adjusted hydration condition from the initial hydration condition and the water loss measurement (750). In one embodiment, the initial hydration condition may be a total mass or volume of water in the interstitial fluid or skin tissue water. In another embodiment, the initial hydration condition may be a total mass or volume of water of the user. In one embodiment, the adjusted hydration condition may be the difference between the initial hydration condition and the water loss measurement. In another embodiment, the adjusted hydration condition may be a percentage of interstitial fluid or skin tissue water that is remaining given the water loss measurement (e.g., adjusted hydration condition=(initial hydration condition−water loss measurement)/(initial hydration condition), and so forth). In another embodiment, the processing device 404 (FIG. 4) may receive user input of water intake and water discharge (e.g., urination, vomiting, and so forth). The processing device 404 (FIG. 4) may calculate the adjusted hydration condition by subtracting water loss and water discharge from the initial hydration condition and adding water intake. In another embodiment, a hydration of the individual may include a hypo-hydrated level (dehydrated or under hydrated condition), a euhydrated level (normal hydration condition), or a hyper-hydrated level (over hydrated condition). In one embodiment, the adjusted hydration condition may indicate that the individual is trending towards a dehydrated condition. In another embodiment, the adjusted hydration condition may indicate a user is trending towards a normal hydration condition. In another embodiment, the adjusted hydration condition may indicate that the individual is trending towards an over-hydrated condition.

The method may include, displaying the adjusted hydration condition to a user (755). In one embodiment, the adjusted hydration condition may be displayed on a display device integrated into the housing (e.g., LEDs, GUIs, and so forth). In one embodiment, LEDs may provide an indication of the user's hydration level (e.g., different colors for dehydrated, normal hydration, and overhydrated, an amount of LEDs activated indicates the amount of hydration, activating a LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smartphone, a computer, and so forth). The other device may display the adjusted hydration condition.

Figure 8A:
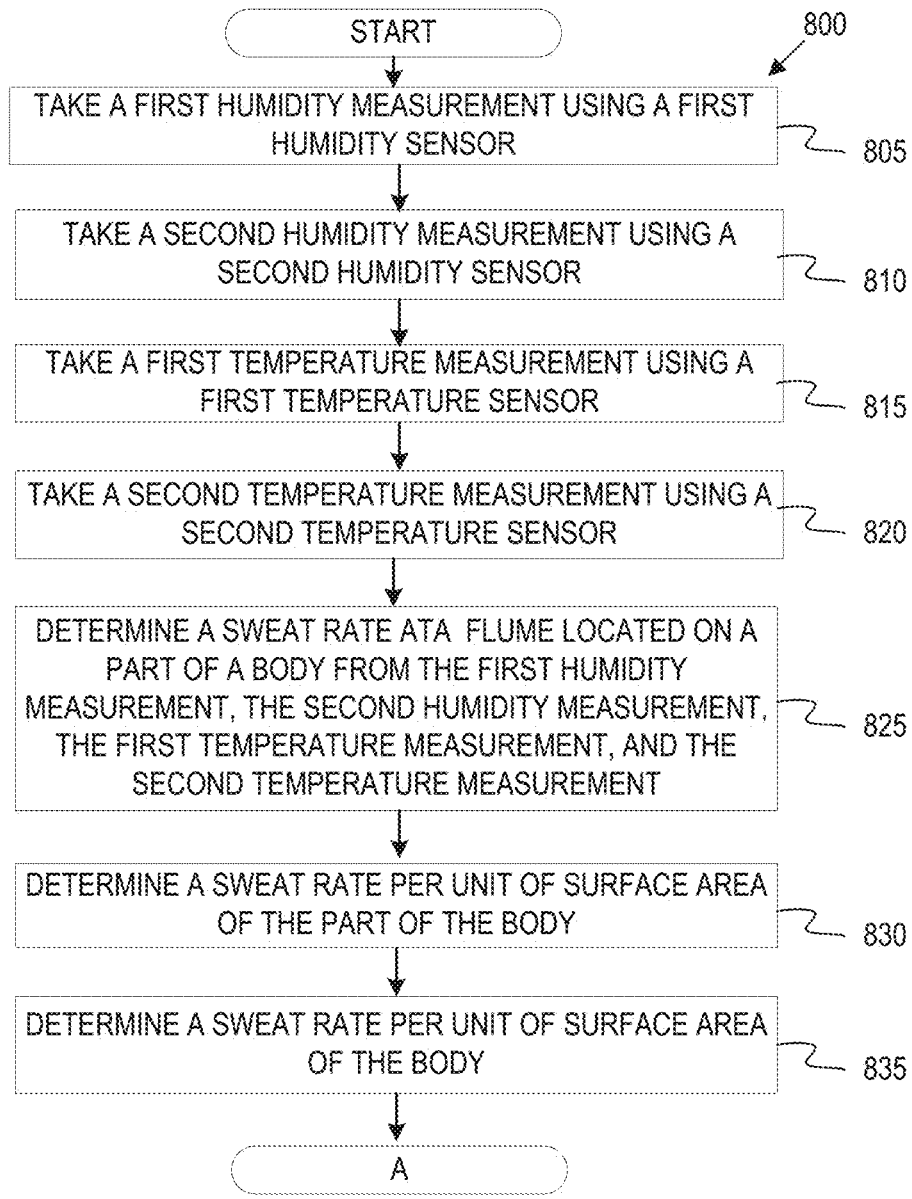
FIG. 8A illustrates a flow diagram of a method for determining a total sweat rate according to one embodiment.

FIG. 8A illustrates a flow diagram of a method 800 for determining a total sweat rate according to one embodiment. The method 800 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 800 may be performed, in part, by processing logic of processing device 404 (FIG. 4).

For simplicity of explanation, the method 800 is illustrated and described as a series of acts. However, acts in accordance with this disclosure can occur in various orders and/or concurrently and with other acts not presented as described herein. Furthermore, not all illustrated acts may be performed to implement the method 800 in accordance with the disclosed subject matter. In addition, those skilled in the art will understand and appreciate that the method 800 could alternatively be represented as a series of interrelated states via a state diagram or events.

The method may include, taking a first humidity measurement using a first humidity sensor (805). The first humidity measurement may be a relative humidity measurement of the air in the flume 510 (FIG. 5) at a first location. The method may include, taking a second humidity measurement using a second humidity sensor (810). The method may include, taking a first temperature measurement using a first temperature sensor (815). The method may include, taking a second temperature measurement using a second temperature sensor (820).

The method may include, determining a sweat rate at a flume located on a part of a body from a first humidity measurement, the second humidity measurement, the first temperature measurement, and the second temperature measurement (825). In one embodiment, The processing device 404 (FIG. 4) may calculate sweat from a first vapor pressure measurement and a second vapor pressure measurement as discussed in the preceding paragraphs. The processing device 404 (FIG. 4) may calculate the first vapor pressure measurement may be calculated from the first humidity measurement and the first temperature measurement as discussed in the preceding paragraphs. The processing device 404 (FIG. 4) may calculate the second vapor pressure measurement may be calculated from the second humidity measurement and the second temperature measurement as discussed in the preceding paragraphs.

The method may include, determining a sweat rate per unit of surface area of the part of the body where the flume is disposed (830). In one embodiment, a body mapping of sweating patterns may be used. The body mapping of sweating patterns may include determining a sweat rate for different parts of the body. In one embodiment, the body mapping of sweating patterns may be determined by taking measurements of sweat at different locations (e.g., attaching pads to an individual and measuring sweat in the pads, and so forth) of the body during one or more activities (e.g., exercising, working, and so forth). In one embodiment, the measurements may be previously taken of the user of the electronic device. In another embodiment, the measurements may be averaged for a group of individuals with similar characteristics. In another embodiment, the measurements may be located in a database. For example, it may be determined that for an average male at a certain intensity has a sweat rate of 226 grams per meter squared of body surface area per hour ($g*m\hat{~}-2*h\hat{~}-1$) at the forearm/wrist area.

The method may include, determining a sweat rate per unit of surface area of the body (835). In one embodiment, the sum of the sweat rates per unit area of each body part determined through body mapping may equal the total sweat rate per unit area for the body. For example, it may be determined that for an average male at a certain intensity has a sweat rate of 226 grams per meter squared of body surface area per hour ($g*m\hat{~}-2*h\hat{~}-1$) at the forearm/wrist area and the sum of all of the sweat rates gives a total sweat rate of 9477 $g*m\hat{~}-2*h\hat{~}-1$ for the entire body.

Figure 8B:
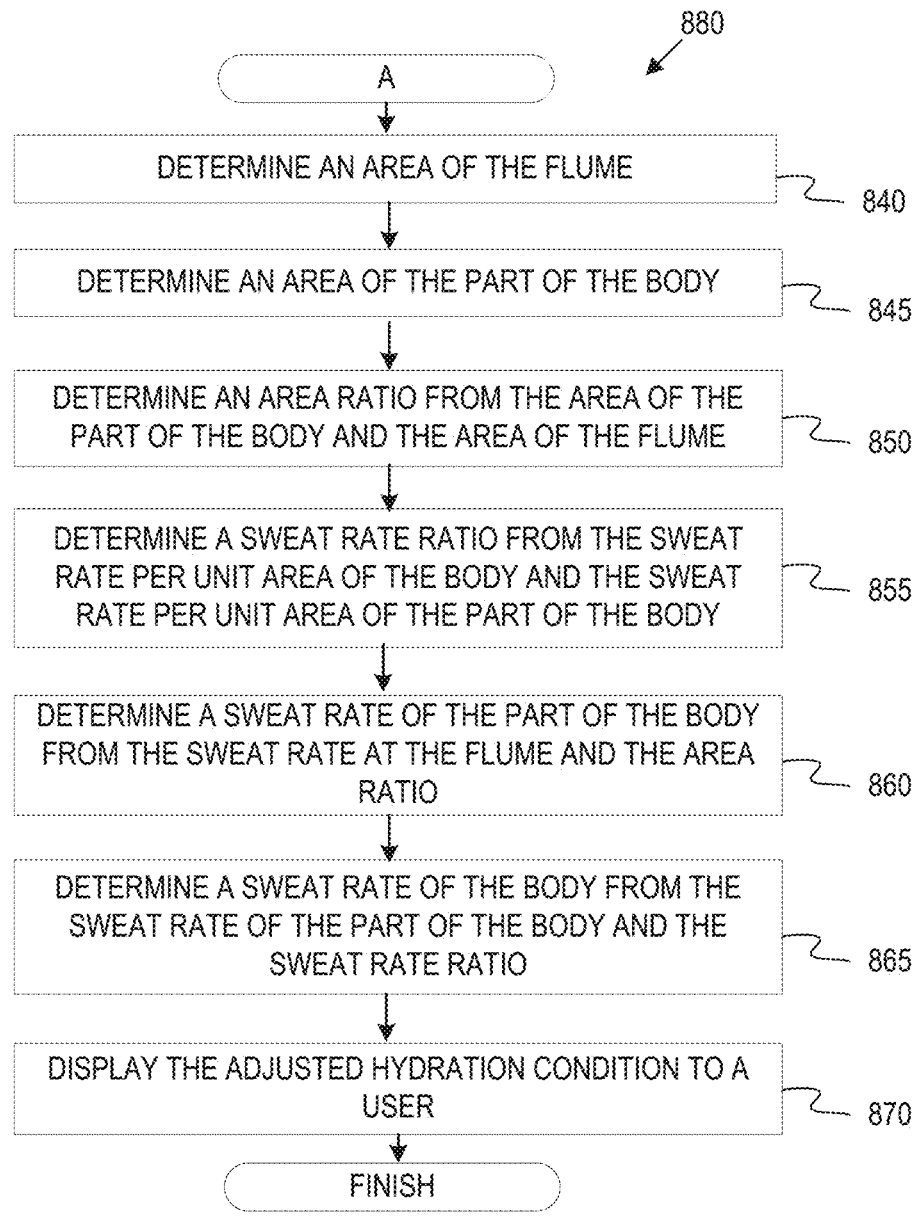
FIG. 8B illustrates another flow diagram of a method for determining a total sweat rate according to one embodiment.

FIG. 8B illustrates a flow diagram of a method 880 for determining a total sweat rate according to one embodiment. The method 880 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 880 may be performed, in part, by processing logic of processing device 404 (FIG. 4).

The method 880 may continue from block 835 of FIG. 8A. The method may include, determining an area of the flume (840). In one embodiment, the area of the flume is a cross-sectional area of a portion of the tube proximate the bottom wall of the electronic device. In one embodiment, the area of the flume is the area of the skin that directly communicates with the flume.

The method may include, determining an area of the part of the body where the flume is disposed (845). The area of the part of the body may be a surface area. In one embodiment, an area of the body part may be determined during body mapping. In another embodiment, an area of the body part may be located in a database. The area of the body part in the database may be indexed by one or more of gender, weight, height, age, or other information. In another embodiment, a body surface area (BSA) may be calculated. For example, the Du Bois formula may be used where BSA=$0.007184*(W\hat{~}0.425)*(H\hat{~}0.725)$, where W is the weight in kilograms and H is the height in centimeters. For another example, the Mosteller formula may be used where BSA=$((W*H)\hat{~}0.5)/60$, where W is weight in kilograms and H is height in centimeters. Other examples of formulas include the Haycok, Gehan and George, Boyd, Fujimoto, Takahira, Schlich, or other formulas. In another embodiment, a database including average BSA for individuals by age may be used. The BSA may be multiplied by an average ratio of the body part to entire body surface area to calculate the body part surface area. For example, if the BSA for an individual were determined to be 1.9 m^2 and if the ratio of forearm to entire body surface area were 0.03, the surface area of the forearm would be calculated at 0.057 m^2.

The method may include, determining an area ratio from the area of the part of the body and the area of the flume (850). In one embodiment, the area ratio may be calculated by dividing the area of the part of the body by the area of the flume.

The method may include, determining a sweat rate ratio from the sweat rate per unit area of the body and the sweat rate per unit area of the part of the body (855). In one embodiment, the sweat rate ratio may be calculated by dividing the sweat rate per unit area of the body by the sweat rate per unit area of the part of the body.

The method may include, determining a sweat rate of the part of the body from the sweat rate at the flume and the area ratio (860). In one embodiment, the sweat rate of the part of the body may be calculated by multiplying the sweat rate at the flume by the area ratio.

The method may include, determining a sweat rate of the body from the sweat rate of the part of the body and the sweat rate ratio (865). The processing device 404 (FIG. 4) may determine the sweat rate of the body by multiplying the sweat rate at the part of the body by the sweat rate ratio.

The method may include, displaying the adjusted hydration condition to a user (870). In one embodiment, the adjusted hydration condition may be displayed on a display device integrated into the housing (e.g., LEDs, GUIs, and so forth). In one embodiment, LEDs may provide an indication of the user's hydration level (e.g., different colors for dehydrated, normal hydration, and overhydrated, an amount of LEDs activated indicates the amount of hydration, activating a LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smartphone, a computer, and so forth). The other device may display the adjusted hydration condition.

FIG. 9 illustrates an air flow sensor 900 according to one embodiment. The electronic device 500 (FIG. 5A or 5B) may include an air flow sensor 900. The air flow sensor 900 may include a micro-heating element 910. The micro-heating element 910 may be a thermistor, a heated wire, a piezometer, a piezometer ring, and so forth. The air flow sensor 900 may include a first heat sensor 920 at a first location and a second heat sensor 930 at a second location. The first heat sensor 920 may determine a first temperature measurement at the first location and the second heat sensor 930 may determine a second temperature measurement at the second location. As air passes over the micro-heating element 910, a temperature gradient (e.g., a difference in temperature over a distance, etc.) may form in the air passing by the first heat sensor 920 and the second heat sensor 930. As the velocity of the air passing by the first heat sensor 920 and the second heat sensor 930 increases, the difference in temperature measured at the first heat sensor 920 and second heat sensor 930 may increase. The processing device 404 (FIG. 4) may determine an air speed measurement from the first temperature measurement and the second temperature measurement. In one embodiment, the processing device 404 (FIG. 4) may determine the air speed measurement from a database in view of the first temperature measurement and the second temperature measurement. In one embodiment, the processing device 404 (FIG. 4) may calculate the air speed measurement from the first temperature measurement and the second measurement as described below.

In one embodiment, the processing device 404 (FIG. 4) may determine the air speed measurement from a voltage or current of the micro-heating element 910. The processing device 404 (FIG. 4) may heat the micro-heating element 910 electrically by delivering an electrical signal (e.g., voltage, electrical current, and so forth). The micro-heating element may have a resistance. The heat generated at the micro-heating element 910 may be dependent on the electrical signal (e.g., voltage or electrical current) and the resistance of the micro-heating element 910. The air passing by the micro-heating element 910 may have a cooling effect on the micro-heating element 910. The resistance of the micro-heating element may be dependent upon the temperature of the micro-heating element 910. As the resistance changes due to the change in temperature caused by the air flow, the processing device 404 (FIG. 4) may determine a voltage output as the electronic device 500 (FIG. 5A or 5B) attempts to maintain a specific variable (e.g., current, voltage, temperature, and so forth) constant following Ohm's law (current equals voltage divided by resistance). The processing device 404 (FIG. 4) can determine the air flow from the change in temperature at the micro-heating element 910. In one embodiment, the processing device 404 (FIG. 4) may determine a change in ambient temperature from a temperature sensor (e.g., the ambient temperature sensor, and so forth) to determine a change in temperature at the micro-heating element due to air flow and not due to change in ambient temperature.

As the air flow changes, the feels-like temperature may change. Air flow may be created by the user moving, wind, or some other factor. In one embodiment, air flow can facilitate sweat evaporation and create a lower feels-like temperature. In another embodiment, air flow can transfer heat from the user to the air through convection causing a lower-feels like temperature.

The processing device 404 (FIG. 4) may combine the air flow measurement determined by an air flow sensor 900 with an ambient temperature measurement to determine an adjusted baseline (e.g., wind chill factor, and so forth). A baseline may also be referred to herein as a baseline condition. The processing device may combine the air flow measurement, the ambient temperature measurement, and an ambient humidity measurement to determine an adjusted baseline (e.g., feels-like temperature, and so forth). The processing device 404 (FIG. 4) may compare the adjusted baseline with one or more other measurements (e.g., skin temperature measurement, previous sweat rate measurements, and so forth) to determine at least one of a current sweat rate, a predicted sweat rate, a change in sweat rate, and so forth.

Figure 10:
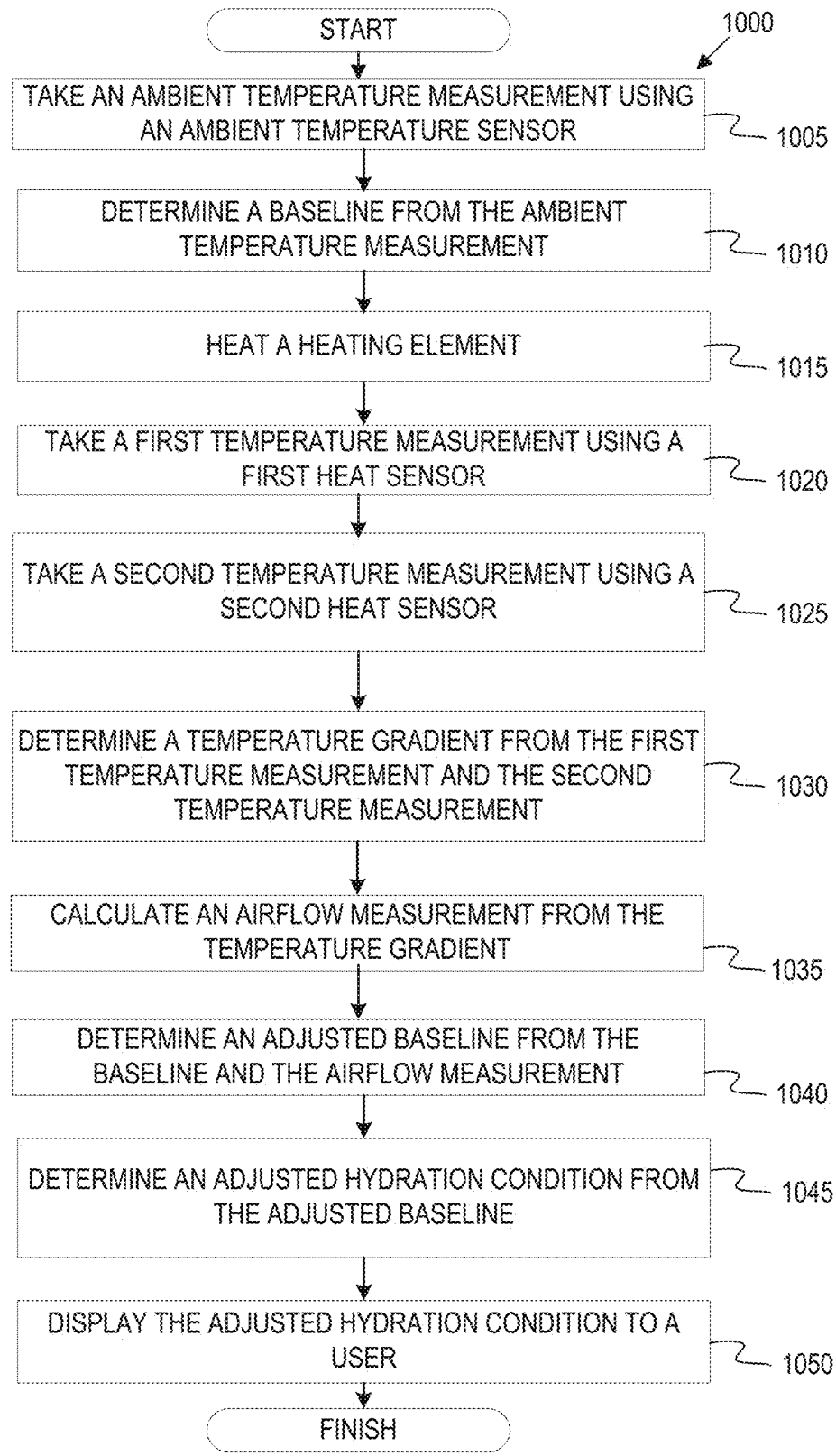
FIG. 10 illustrates a flow diagram of a method of determining a hydration condition according to one embodiment.

FIG. 10 illustrates a flow diagram of a method 1000 of determining a hydration condition according to one embodiment. The method 1000 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 1000 may be performed, in part, by processing logic of processing device 404 (FIG. 4).

For simplicity of explanation, the method 1000 is depicted and described as a series of acts. However, acts in accordance with this disclosure can occur in various orders and/or concurrently and with other acts not presented as described herein. Furthermore, not all illustrated acts may be performed to implement the method 1000 in accordance with the disclosed subject matter. In addition, those skilled in the art will understand and appreciate that the method 1000 could alternatively be represented as a series of inter-related states via a state diagram or events.

The method may include, taking an ambient temperature measurement using an ambient temperature sensor (1005). The method may include, determining a baseline from the ambient temperature measurement (1010). For example, if the ambient temperature measurement is 75 degrees Fahrenheit (° F.), the baseline may also be 75° F.

Figure 11:
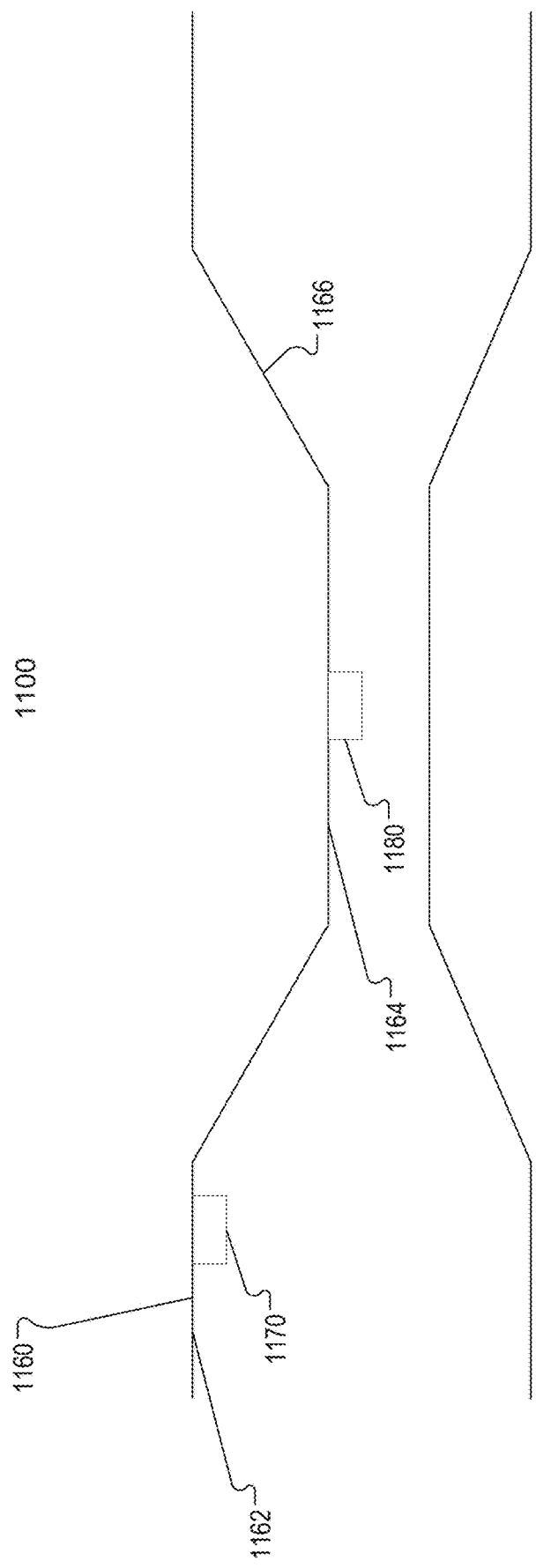
FIG. 11 illustrates an air flow sensor according to another embodiment.

The method may include, determining a first cross-sectional area at a first location (1015). As discussed below, the first location may be a first passage 1162, a second passage 1164, or a third passage 1166 of a tube 1160 (FIG. 11). In one embodiment, the first location may be an inlet or first passage 1162 of the tube 1160 (FIG. 11). In another embodiment, the second location may be the throat or the second passage 1164 of the tube 1160 (FIG. 11). The first location (e.g., a passage of tube 1160 (FIG. 1), or other location) may be located on the electronic device 500 (FIG. 5A or 5B) to be exposed to air flow when the user is moving, when there is wind, and so forth.

The method may include, determining a second cross-sectional area at a second location (1020). As discussed below, the second location may be a first passage 1162, a second passage 1164, or a third passage 1166 of a tube 1160 (FIG. 11). In one embodiment, the second location may be the throat or the second passage 1164 of the tube 1160 (FIG. 11). In another embodiment, the second location may be an outlet or the third passage 1166 of the tube 1160 (FIG. 11). The second location (e.g., a passage of tube 1160 (FIG. 11), or other location) may be located on the electronic device 500 (FIG. 5A or 5B) to be exposed to air flow when the user is moving, when there is wind, and so forth.

The method may include, taking a first pressure measurement using a first pressure sensor at a first location (1025).

The method may include, taking a second pressure measurement using a second pressure sensor at a second location (1030). The first location and second location may be located on the electronic device 500 (FIG. 5A or 5B) at a distance and at different cross-sectional areas to allow the processing device 404 (FIG. 4) to determine a difference in pressure depending on the velocity of the air flow.

The method may include, determining an air flow measurement from the first pressure measurement, the first cross-sectional area, the second pressure measurement, and the second cross-sectional area (1035). The processing device 404 (FIG. 4) may use a Bernoulli equation (e.g., $V=C*\text{sqrt}(2*(P1-P2)/(\text{density}*(1-(A2/A1)^2)))$, where C is a discharge coefficient, P1 is the first pressure measurement, A1 is the first cross-sectional area, P2 is the second pressure measurement, and A2 is the second cross-sectional area, and so forth) or some other equation. In another embodiment, the processing device 404 (FIG. 4) may use empirical data to determine the air flow measurement. In one embodiment, the empirical data may be stored in a database and may include a plurality of measurements and a plurality of corresponding measurements as measured by the electronic device 500 (FIG. 5A or 5B). For example, the database may list a baseline air flow velocity corresponding to a first pressure measurement, a first cross-sectional area, a second pressure measurement, and a second cross-sectional area as measured by the electronic device 500 (FIG. 5A or 5B). In another embodiment, the empirical data may be stored in a database and may include a plurality of measurements and a plurality of corresponding measurements as measured by one or more electronic devices other than the electronic device 500 (FIG. 5A or 5B). For example, the database may list a baseline air flow velocity corresponding to a first pressure measurement, a first cross-sectional area, a second pressure measurement, and a second cross-sectional area as measured by one or more electronic devices other than the electronic device 500 (FIG. 5A or 5B).

The method may include, determining an adjusted baseline from the baseline and the air flow measurement (1040). In one embodiment, the processing device 540 (FIG. 5) may determine the adjusted baseline as discussed above.

The method may include, determining an adjusted hydration condition from the adjusted baseline (1045). In one embodiment, the processing device 540 (FIG. 5) may determine the adjusted hydration condition as discussed above.

The method may include, displaying the adjusted hydration condition to a user (1050). In one embodiment, the adjusted hydration condition may be displayed on a display device integrated into the housing (e.g., LEDs, GUIs, and so forth). In one embodiment, LEDs may provide an indication of the user's hydration level (e.g., different colors for dehydrated, normal hydration, and overhydrated, an amount of LEDs activated indicates the amount of hydration, activating a LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smartphone, a computer, and so forth). The other device may display the adjusted hydration condition.

FIG. 11 illustrates an air flow sensor according to another embodiment. The electronic device 500 (FIG. 5A or 5B) may include an air flow sensor 1100. The air flow sensor 1100 includes a tube 1160 (e.g., a venturi meter, and so forth). The tube 1160 may have a first passage 1162, a second passage 1164, and a third passage 1166. The first passage 1162, the second passage 1164, and third passage 1166 may each be cylindrical and may share a central axis. Air may flow from the first passage 1162 to the second passage 1164 to the third passage 1166. The first passage 1162 may have a first diameter, the second passage 1164 may have a second diameter, and the third passage 1166 may have a third diameter. The first passage 1162 may be an inlet 1162, the second passage 1164 may be a throat 1164, and the third passage may be an outlet 1166. A first pressure sensor 1170 may be located in the tube 1160 at a first location. A second pressure sensor 1180 may be located in the tube 1160 at a second location. In one embodiment, the first pressure sensor 1170 may be located at the first passage 1162 and the second pressure sensor 1180 may be located at the second passage 1164. In another embodiment, the first pressure sensor 1170 may be located at the first passage 1162 and the second pressure sensor may be located at the third passage 1166. In another embodiment, the first pressure sensor 1170 may be located at the second passage 1164 and the second pressure sensor 1180 may be located at the third passage 1166. The first pressure sensor 1170 may provide a first pressure measurement at the first location (e.g., first passage 1162, second passage 1164, third passage 1166, and so forth). The first location may have a first cross-sectional area. The second pressure sensor 1180 may provide a second pressure measurement at the second location (e.g., a passage different than the first location, etc.). The second location may have a second cross-sectional area. In one embodiment, the processing device 404 (FIG. 4) may determine an air speed measurement by accessing a database in view of the first pressure measurement, the first cross-sectional area, the second pressure measurement, and the second cross-sectional area. In one embodiment, the processing device 404 (FIG. 4) may calculate the air speed measurement in view of the first pressure measurement, the first cross-sectional area, the second pressure measurement, and the second cross-sectional area as described below.

In other embodiments, the pressure sensor may be a thermal anemometer (e.g., hot-wire anemometer, and so forth), a mechanical anemometer (e.g., cup anemometer, vane anemometer, and so forth), a laser Doppler anemometer, a sonic anemometer, an acoustic resonance anemometer, a plate anemometer, a tube anemometer, a pitot tube, a thermistor probe with sensors, a manometer, an orifice, and so forth.

As the air flow changes, the feels-like temperature may change. Air flow may be created by the user moving, wind, or some other factor. In one embodiment, air flow can facilitate sweat evaporation and create a lower feels-like temperature. In another embodiment, air flow can transfer heat from the user to the air through convection causing a lower-feels like temperature.

The processing device 404 (FIG. 4) may combine the air flow measurement determined by an air flow sensor 1100 with an ambient temperature measurement to determine an adjusted baseline (e.g., wind chill factor, and so forth). The processing device may combine the air flow measurement, the ambient temperature measurement, and an ambient humidity measurement to determine an adjusted baseline (e.g., feels-like temperature, and so forth). The processing device 404 (FIG. 4) may compare the adjusted baseline with one or more other measurements (e.g., skin temperature measurement, previous sweat rate measurements, and so forth) to determine at least one of a current sweat rate, a predicted sweat rate, a change in sweat rate, and so forth.

Figure 12:
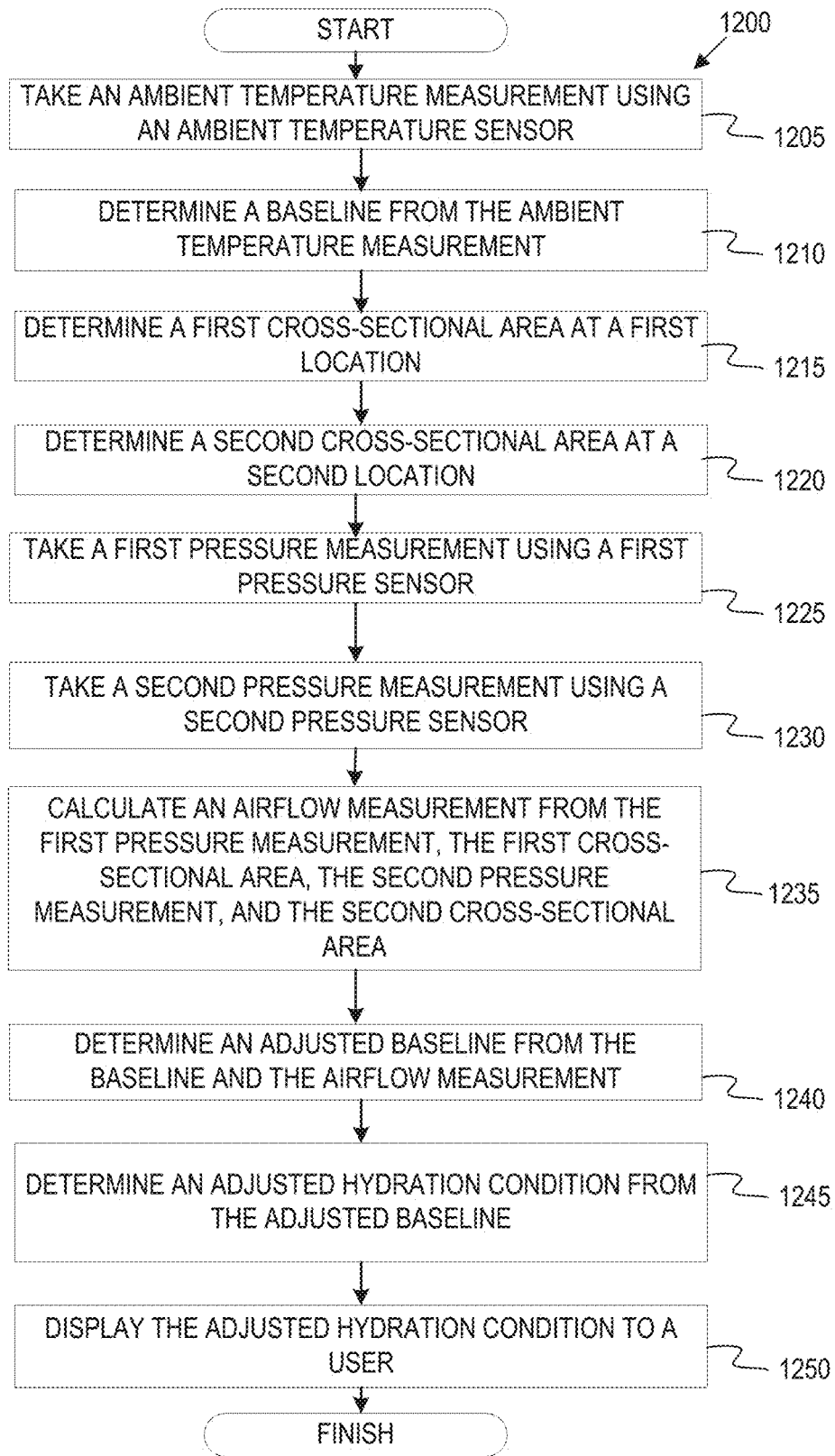
FIG. 12 illustrates a flow diagram of a method of determining a hydration condition according to one embodiment.

FIG. 12 illustrates a flow diagram of a method 1200 of determining a hydration condition according to one embodiment. The method 1200 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 1200 may be performed, in part, by processing logic of processing device 404 (FIG. 4).

For simplicity of explanation, the method 1200 is depicted and described as a series of acts. However, acts in accordance with this disclosure can occur in various orders and/or concurrently and with other acts not presented as described herein. Furthermore, not all illustrated acts may be performed to implement the method 1200 in accordance with the disclosed subject matter. In addition, those skilled in the art will understand and appreciate that the method 1200 could alternatively be represented as a series of interrelated states via a state diagram or events.

The method may include, taking an ambient temperature measurement using an ambient temperature sensor (1205). The method may include, determining a baseline from the ambient temperature measurement (1210). For example, if the ambient temperature measurement is 75 degrees Fahrenheit (° F.), the baseline may also be 75° F. The method may include, taking an ambient humidity measurement using an ambient humidity sensor (1215).

The method may include, taking one or more measurements using an air flow sensor (1220). In one embodiment, the air flow sensor may include a micro-heating element, a first heat sensor, and a second heat sensor as described above. The one or more measurements may be a first temperature measurement and a second temperature measurement. In another embodiment, the air flow sensor may include a first pressure sensor at a first cross-sectional area and a second pressure sensor at a second cross-sectional area as described above. The one or more measurements may include a first pressure measurement and a second pressure measurement. In other embodiments, the pressure sensor may be a thermal anemometer (e.g., hot-wire anemometer, and so forth), a mechanical anemometer (e.g., cup anemometer, vane anemometer, and so forth), a laser Doppler anemometer, a sonic anemometer, an acoustic resonance anemometer, a plate anemometer, a tube anemometer, a pitot tube, a thermistor probe with sensors, a manometer, an orifice, and so forth. The processing device 404 (FIG. 4) may calculate the air flow measurement from one or more measurements from the air flow sensor.

The method may include, calculating an air flow measurement from the one or more measurements (1235). The air flow measurement may be calculated as discussed above. The method may include, determining an adjusted baseline from the baseline, the ambient humidity measurement, and the air flow measurement (1240). In one embodiment, as the body temperature rises due to an event (e.g., the ambient temperature is above skin temperature, heat generation due to exercising or a medical condition, and so forth), the body may attempt to dissipate heat through sweating. Heat dissipation will occur when the sweat evaporates, thereby influencing the adjusted baseline that is perceived (e.g., apparent temperature, relative temperature, feels-like temperature, and so forth). Air flow can increase the rate of sweat evaporation, thereby causing an adjusted baseline that feels cooler. High ambient humidity can decrease the rate of sweat evaporation, thereby causing an adjusted baseline that feels warmer.

As the body continues to generate heat due to an ongoing event, the body may attempt to dissipate heat at a sweat rate. The ambient temperature, ambient humidity, and air flow may affect the sweat evaporation rate. If the sweat rate is above the sweat evaporation rate, the adjusted baseline may feel warmer.

In one embodiment, as the body temperature decreases due to an event (e.g., ambient temperature is below skin temperature, a medical condition, and so forth), the body may constrict blood vessels to reduce flow of blood to the skin to reduce heat loss from the skin to the environment. Constriction of blood vessels may decrease the body's thirst response and may increase the body's urine production which may affect the body's hydration condition. Air flow can make the adjusted baseline feel cooler as the air flow wicks heat away from the body through convection. High humidity can make the adjusted baseline feel cooler because the water in the humid air has a higher specific heat than air. Therefore cold air with a higher humidity may transfer heat from a body at a higher rate than cold air at a lower humidity.

The ambient temperature, ambient humidity, and air flow may affect the adjusted baseline. In one embodiment, the processing device 404 (FIG. 4) may access a database to determine the adjusted baseline. The database may include an index that combines air temperature and humidity (e.g., heat index, humiture, humidex, and so forth), an index that combines air temperature and air flow (e.g., wind chill, and so forth) an index that combines air temperature, humidity, and air flow (e.g., wet-bulb globe temperature (WBGT), and so forth), or some other database. In one embodiment, the processing device 404 (FIG. 4) may calculate an adjusted baseline from the ambient humidity measurement, the air flow measurement, and the ambient temperature measurement.

For example, the wind chill in degrees Fahrenheit (° F.) may be calculated by Wind Chill (° F.)=35.74+0.6215*T−35.75(V*0.16)+0.4275T*(V0.16), where V is the wind speed value in miles per hour (mph) and T is the temperature in ° F. In another example, WBGT (in degrees Celsius (° C.) or ° F.) may be calculated by WBGT=0.7*Tw+0.2*Tg+0.1*Td, where Tw is the wet bulb temperature (a temperature air where it is cooled to saturation (100% relative humidity)), Tg is the global thermometer temperature or mean radiant temperature (uniform temperature of an imaginary enclosure in which the radiant heat transfer from the human body is equal to the radiant heat transfer in the actual non-uniform enclosure, Tg may be measured with a globe thermometer or black globe thermometer), and Td is the dry-bulb temperature (temperature of air measured by a thermometer freely exposed to the air but shielded from radiation and moisture).

In another embodiment, the processing device 404 (FIG. 4) may use empirical data to determine the adjusted baseline. In one embodiment, the empirical data may be stored in a database and may include a plurality of measurements and a plurality of corresponding measurements as measured by the electronic device 500 (FIG. 5A or 5B). For example, the database may list an adjusted baseline corresponding to two or more of a temperature measurement, a humidity measurement, and an air flow measurement as measured by the electronic device 500 (FIG. 5A or 5B). In another embodiment, the empirical data may be stored in a database and may include a plurality of measurements and a plurality of corresponding measurements as measured by one or more electronic devices other than the electronic device 500 (FIG. 5A or 5B). For example, the database may list an adjusted baseline corresponding to a two or more of a temperature measurement, a humidity measurement, and an air flow measurement as measured by one or more electronic devices other than the electronic device 500 (FIG. 5A or 5B).

The method may include, taking a skin temperature measurement using a skin temperature sensor (1235). The skin temperature measurement may be located on the bottom wall 601 of the electronic device 500 (FIG. 5A or 5B). The method may include, determining an adjusted hydration condition from the adjusted baseline and the skin temperature measurement (1245). In one embodiment, the processing device 404 (FIG. 4) may determine a first hydration condition from one or more physiological measurements (e.g., a sweat rate, a vapor pressure measurement, a humidity measurement, an impedance measurement, a backscatter measurement, a sodium level, a potassium level, a past hydration condition, a current hydration condition, events that triggered a hydration condition, and so forth). In one embodiment, the adjusted hydration condition may indicate a current hydration condition. In another embodiment, the adjusted hydration condition may predict a future hydration condition.

The processing device 404 (FIG. 4) may determine a sweat rate from the adjusted baseline and skin temperature measurement. The processing device 404 (FIG. 4) may determine an adjusted hydration condition based on the first hydration condition and the sweat rate. If the first hydration condition is a previous hydration condition, the adjusted hydration condition may be a current or future hydration condition. If the first hydration condition is a current hydration condition, the adjusted hydration condition may be a future hydration condition.

In one embodiment, the processing device 404 (FIG. 4) may have access to a database of hydration conditions in view of at least one of adjusted baselines, skin temperature measurements, or physiological measurements. The processing device 404 (FIG. 4) may access the database and determine an adjusted hydration condition in view of at least one of an adjusted baseline, a skin temperature measurement, or one or more physiological measurements. The adjusted hydration condition may be a current hydration condition, a future hydration condition, a hydration condition rate (e.g., a sweat rate, and so forth), and so forth. In one embodiment, the database may include an average of hydration conditions of a plurality of individuals in view of at least one of adjusted baselines, skin temperature measurements, or physiological measurements. In one embodiment, the database may include previous hydration conditions of the user of the electronic device in view of at least one of previously adjusted baselines, previous skin temperature measurements, or previous physiological measurements.

For example, the database may include an adjusted hydration condition in view of a skin temperature drop (e.g., dehydration due to heat exhaustion, dehydration due to hypovolema, and so forth). As another example, the database may include an adjusted hydration condition in view of a specific skin temperature rise (e.g., dehydration due to direct exposure to the sun, dehydration due to heat stroke, dehydration due to hyperthyroidism, dehydration due to certain infections, and so forth). The processing device 404 (FIG. 4) may access the database and determine an adjusted hydration condition of dehydration in view of the skin temperature rise or drop.

The method may include, displaying the adjusted hydration condition to a user (1250). In one embodiment, the adjusted hydration condition may be displayed on a display device integrated into the housing (e.g., LEDs, GUIs, and so forth). In one embodiment, LEDs may provide an indication of the user's hydration level (e.g., different colors for dehydrated, normal hydration, and overhydrated, an amount of LEDs activated indicates the amount of hydration, activating a LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smartphone, a computer, and so forth). The other device may display the adjusted hydration condition.

Figure 13:
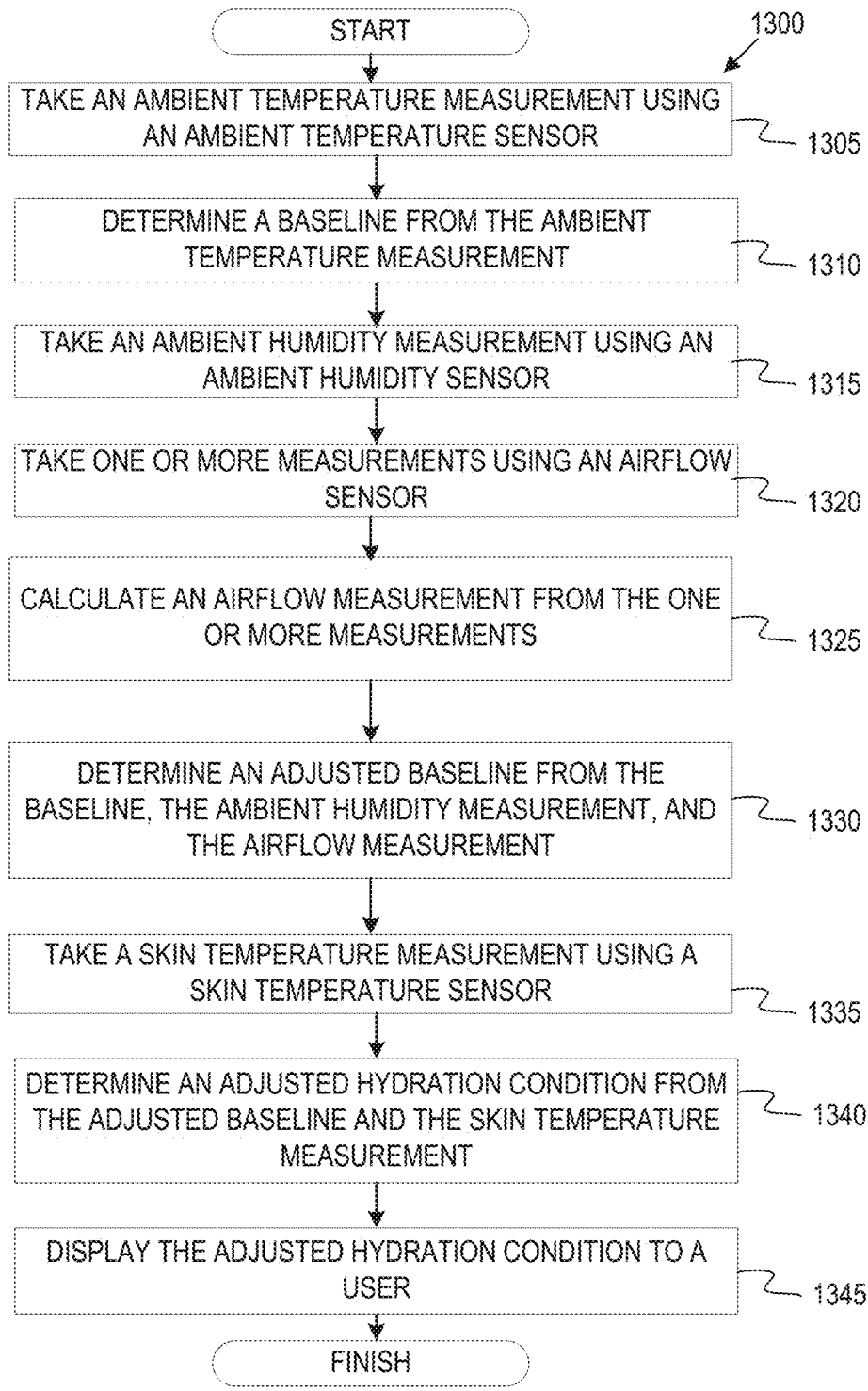
FIG. 13 illustrates a flow diagram of a method of determining a hydration condition according to one embodiment.

FIG. 13 illustrates a flow diagram of a method 1300 of determining a hydration condition according to one embodiment. The method 1300 may be performed by processing logic that may include hardware (e.g., circuitry, dedicated logic, programmable logic, microcode, and so forth), software (such as instruction run on a processing device, a general purpose computer system, or a dedicated machine, firmware, or a combination thereof. In one embodiment, the method 1300 may be performed, in part, by processing logic of processing device 404 (FIG. 4).

For simplicity of explanation, the method 1300 is depicted and described as a series of acts. However, acts in accordance with this disclosure can occur in various orders and/or concurrently and with other acts not presented as described herein. Furthermore, not all illustrated acts may be performed to implement the method 1300 in accordance with the disclosed subject matter. In addition, those skilled in the art will understand and appreciate that the method 1300 could alternatively be represented as a series of interrelated states via a state diagram or events.

The method may include, taking an ambient temperature measurement using an ambient temperature sensor (1305). The method may include, determining a baseline from the ambient temperature measurement (1310). For example, if the ambient temperature measurement is 75 degrees Fahrenheit (° F.), the baseline may also be 75° F. The method may include, heating a heating element (1315). The heating element may be a micro-heating element 710 (FIG. 7) such as a thermistor, a heated wire, a piezometer, a piezometer ring, or another type of heating element. The heating element may be located on the electronic device 500 (FIG. 5A or 5B) to be exposed to air flow when the user is moving, when the wind is blowing, and so forth.

The method may include, taking a first temperature measurement using a first heat sensor (1320). The first heat sensor may be similar to first heat sensor 720 (FIG. 7). The first heat sensor may be located on the electronic device 500 (FIG. 5A or 5B) to be exposed to air flow when the user is moving, when there is wind, and so forth. The first heat sensor may be located on the electronic device 500 (FIG. 5A or 5B) to be exposed to heat generated by the heating element.

The method may include, taking a second temperature measurement using a second heat sensor (1325). The second heat sensor may be located on the electronic device 500 (FIG. 5A or 5B) to be exposed to air flow when the user is moving, when there is wind, and so forth. The second heat sensor may be located on the electronic device 500 (FIG. 5A or 5B) to be exposed to heat generated by the heating element. The first heat sensor and second heat sensor may be located on the electronic device 500 (FIG. 5A or 5B) to determine a difference in temperature depending on the velocity of the air flow.

The method may include, determining a temperature gradient from the first temperature measurement and the second temperature measurement (1330). In one embodiment, the temperature gradient may be in all three of the X-, Y-, and Z-directions. In another embodiment, the temperature gradient may be two of the X-, Y-, and Z-directions. In another embodiment, the temperature gradient may be in one of the X-, Y-, and Z-directions. The temperature gradient may be the change in temperature in one direction between the first heat sensor and the second heat sensor.

The method may include, determining an air flow measurement from the temperature gradient (1335). The processing device 404 (FIG. 4) may calculate the air flow measurement in view of the first and second temperature measurements. In one embodiment, the processing device 404 (FIG. 4) may use a root-mean-square speed equation (e.g., vrms=sqrt(3*R*T/Mm), vrms=sqrt(3*k*T/m), and so forth (where vrms is the root mean square of speed, Mm is the molar mass of the gas, R is the molar gas constant, T is the temperature, m is the mass of one molecule of gas, and k is the Boltzmann constant)). In one embodiment, the processing device 404 (FIG. 4) may use the Mach number (e.g., V=a*Ma*sqrt(T/To), where V is the airspeed, a is the speed of sound at standard sea level, Ma is the Mach number, T is the temperature, and To is the standard sea level temperature, and so forth). In one embodiment, the processing device 404 (FIG. 4) may use some other equation (e.g., V=sqrt((To−T)/(2*cp)), V=sqrt(k*R*T), and so forth (where To is the stagnation temperature, cp is the air specific heat, V is the velocity, k is the ratio of specific heats, R is the gas constant, and so forth)). In another embodiment, the processing device 404 (FIG. 4) may use empirical data to determine the air flow measurement.

The method may include, determining an adjusted baseline from the baseline and the air flow measurement (1340). In one embodiment, the processing device 404 (FIG. 4) may calculate a wind chill factor. For example, the wind chill in degrees Fahrenheit (° F.) may be calculated by Wind Chill (° F.)=35.74+0.6215*T−35.75*(V*0.16)+0.4275T*(V*0.16), where V is the wind speed value in miles per hour (mph) and T is the temperature in ° F. For example, if the baseline is 75° F. and the air flow measurement is 50 mph, the adjusted baseline may be 53° F.

The method may include, determining an adjusted hydration condition from the adjusted baseline (1345). The adjusted hydration condition may be a current hydration condition, a future hydration condition, a hydration condition rate (e.g., a sweat rate, and so forth), and so forth. In one embodiment, the processing device 404 (FIG. 4) may determine an adjusted hydration condition in view of previous hydration conditions of the user at a similar adjusted baseline. In another embodiment, the processing device 404 (FIG. 4) may determine an adjusted hydration condition in view of an average hydration condition stored in a database at a similar adjusted baseline. In another embodiment, the processing device 404 (FIG. 4) may determine an adjusted hydration condition in view of the adjusted baseline and one or more other measurements (e.g., ambient humidity measurement, skin temperature measurement, one or more physiological measurements, or another measurement).

The method may include, displaying the adjusted hydration condition to a user (1350). In one embodiment, the adjusted hydration condition may be displayed on a display device integrated into the housing (e.g., LEDs, GUIs, and so forth). In one embodiment, LEDs may provide an indication of the user's hydration level (e.g., different colors for dehydrated, normal hydration, and overhydrated, an amount of LEDs activated indicates the amount of hydration, activating a LED when the user is becoming dehydrated, and so forth). In one embodiment, a GUI may display a hydration level (e.g., percent hydrated, amount of water that the user needs to consume, time until dehydration, and so forth). In one embodiment, the adjusted hydration condition may be communicated to another device (e.g., a smartphone, a computer, and so forth). The other device may display the adjusted hydration condition.

FIG. 14 illustrates a body area network (BAN) devices 1462-1480 communicating using a BAN according to one embodiment. In one embodiment, the BAN may include a wired body area network, a wireless body area network (WBAN), and/or a body sensor network (BSN). The BAN may include multiple wearable computing devices or wearable sensor devices 1462-1476 that are in communication with each other to send and receive data and information. In one example, the BAN devices may include: a BAN device 1460 that is attached or coupled to the body of the user; an BAN device 1462 that is implanted into the body of the user; a BAN device 1468 that is embedded into the body of a user; a BAN device 1470 that is mounted on a surface of the body, and so forth.

In another example, the BAN devices may include devices adjacent the user including: a BAN device 1464 or 1480 shaped to fit in a clothes pockets of the user, a BAN device 1466 that a user can carry, such as a handheld device; a BAN device 1472 that is integrated into clothes of the user; a BAN device 1476 located in a user's bag, a BAN device 1474 integrated into a user's bag, and so forth. In one embodiment, an electronic device is a BAN device. In another embodiment, the BAN devices 1462-1476 may be body sensor units (BSUs) that include a processing device, a sensor, and a communication device. The BSUs can communicate with a body central unit (BCU) 1478 that is a hub for the BAN devices. The BCU 1478 may be located at any of the locations discussed above for the BAN devices 1462-1476. The BCU 1478 may include a processing device, memory, a communication device, and a display.

The BCU 1478 can receive data from a BAN device 1462-1480 and analyze the data. In one example, the BCU 1478 can display the analyzed data using the display of the BCU 1478. In another example, the BCU 1478 can send the analyzed data to a BAN device 1462-1480 or another device. In one embodiment, the BAN devices 1462-1478 may be configured to be minimal sensor devices with low power consumption and a compact design where the BCU 1478 performs the processing of the data.

In another embodiment, the BCU 1478 may be a data hub or data gateway to manage the BAN devices 1462-1480. In another embodiment, the BCU 1478 can provide a user interface to control the BAN devices 1462-1476 and 1480. In another embodiment, the BAN devices 1462-1476, 1480, and/or the BCU 1478 can use wireless private area networks (WPAN) technology as a gateway or relay to reach longer ranges. In one example, the BCU 1478 may use a WPAN to connect the BAN device 1462-1476 or 1480 on the body to the internet. For example, medical professionals can access patient data from the BAN devices 1462-1476 or 1480 online using the internet independent of a location of a patient.

Figure 15:
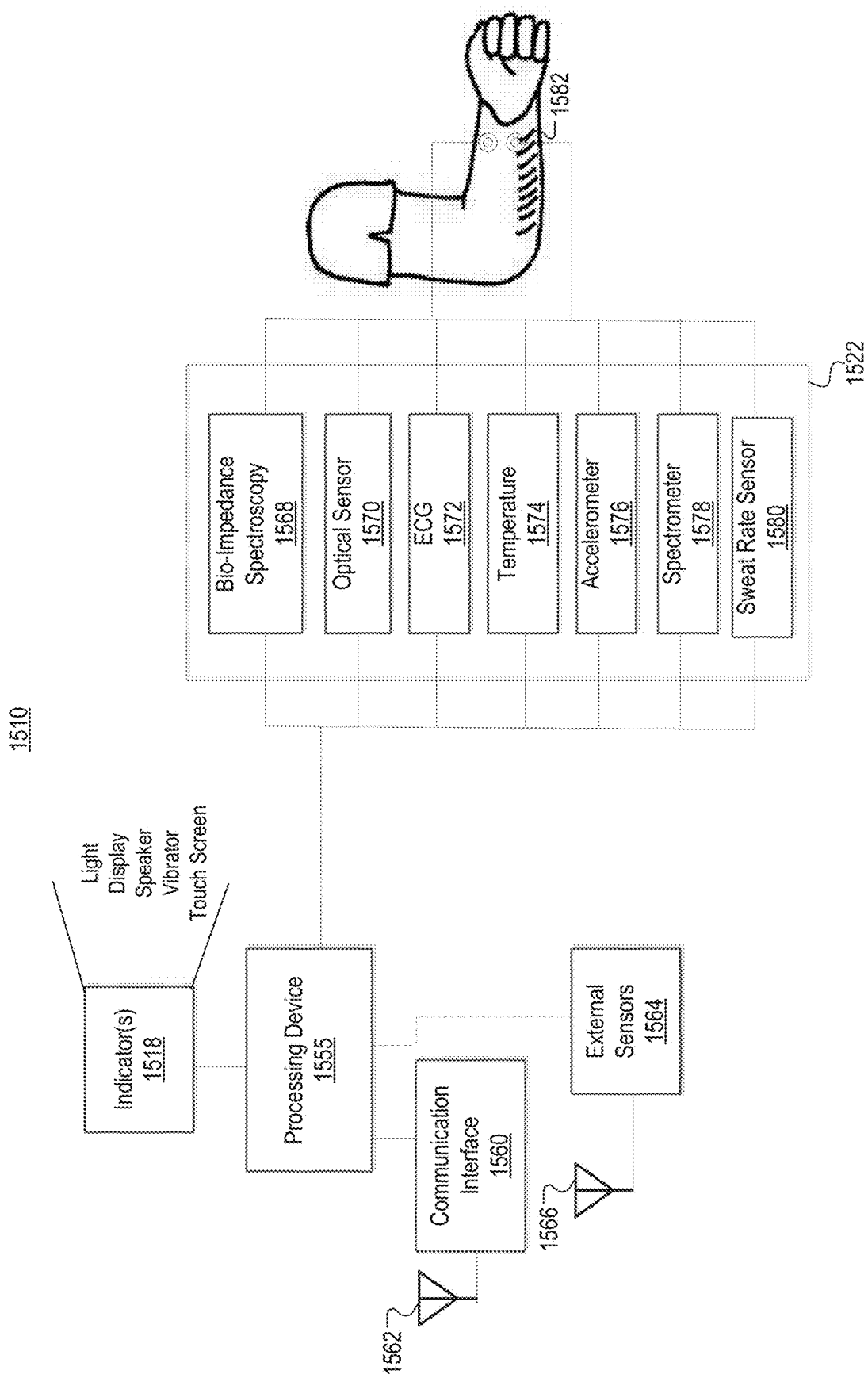
FIG. 15 illustrates a schematic view of an electronic device according to one embodiment.

FIG. 15 illustrates a schematic view of an electronic device 1510 according to one embodiment. The electronic device 1510 may include the indicators 1518, a sensor array 1522 (to include at least one of the sensors in FIG. 1, 2, 3, 4, 5A, or 5B), a processing device 1555, a communications interface 1560, an antenna 1562 coupled with the communications interface 1560, external sensors 1564, and accompanying antenna(s) 1566. In one example, the sensor array 1522 may include one or more physiological sensors to take physiological measurements (e.g., measurements related to the body of the user or animal). The sensor array 1522 may include one or more sensors to engage a user of the electronic device to take measurements. In various examples, the sensor array 1522 may include, without limitation: a bio-impedance spectroscopy sensor 1568 (or simply impedance sensor 1568), an optical sensor 1570, an electrocardiogram (ECG) sensor 1572, a temperature sensor 1574 (such as a thermometer or thermistor), an accelerometer 1576, a spectrometer 1578, a sweat rate sensor 1580, and so forth. In one example, the sensor array 1522 can contact or engage the body of the user at a location 1582.

Figure 16:
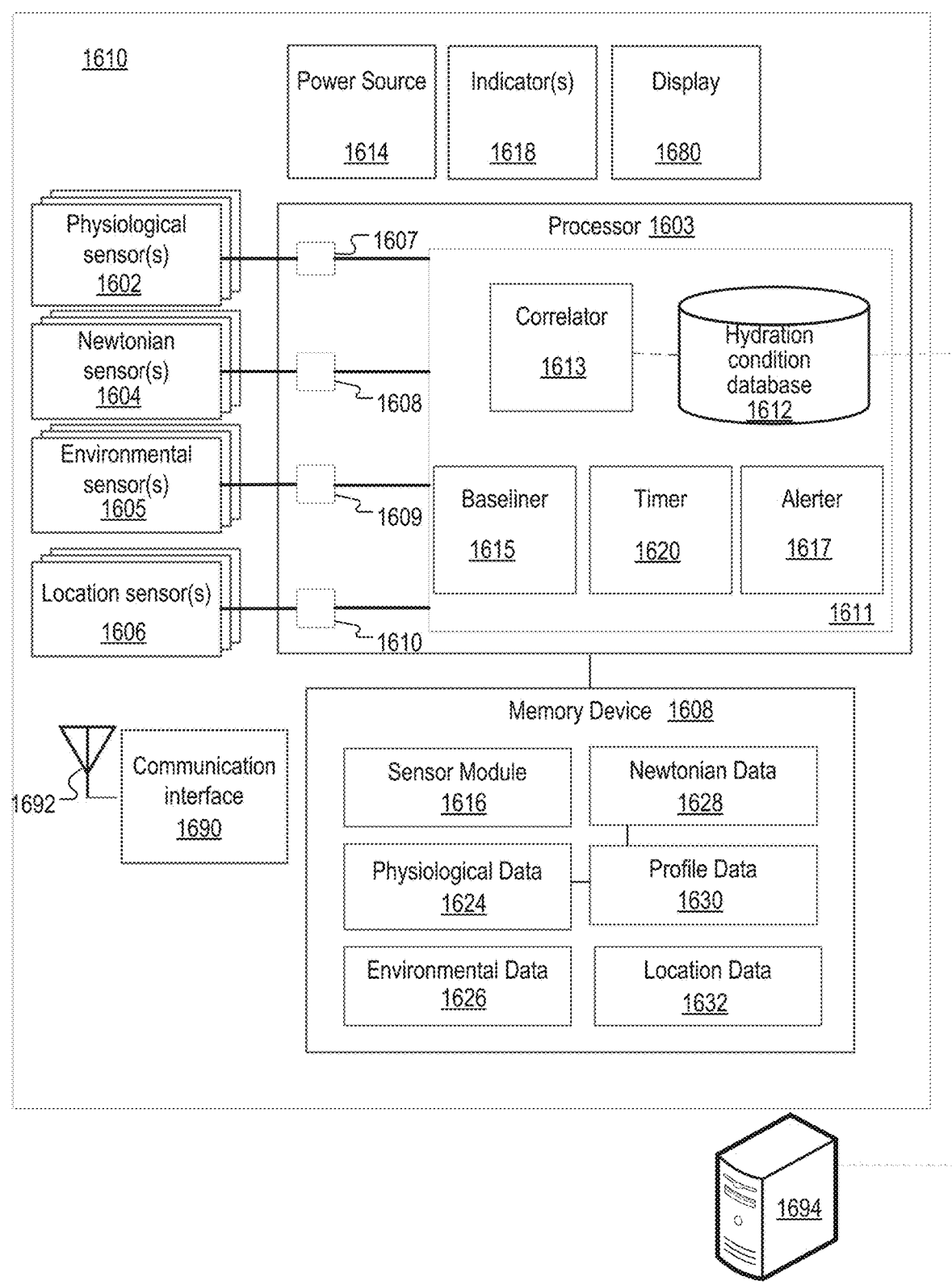
FIG. 16 illustrates a block diagram of the electronic device with a correlator, a baseliner, and an alerter according to one embodiment.

FIG. 16 illustrates a block diagram of the electronic device 1610 with a correlator 1613, a baseliner 1615, and an alerter 1617 according to one embodiment. The electronic device 1610 may include, without limitation, one or more physiological sensor(s) 1602, one or more Newtonian sensor(s) 1604, one or more environmental sensor(s) 1605, one or more location sensor(s) 1606, a processor 1603, a memory device 1608, a display 1680, a communication interface 1690 (such as a radio frequency (RF) circuit), and an antenna 1692 coupled to the communication interface 1690.

In one embodiment, the communication interface 1690 may communicate, via the antenna 1692, with an external electronic device, a computing device, and with other wireless devices such as electronic device 1610 of other users. In one example, the communication interface 1690 may communicate the information using a cellular network, a wireless network, or a combination thereof. In one example, the communications network may be a cellular network employing a third generation partnership project (3GPP®) release 8, 9, 10, 11, or 12 or Institute of Electronics and Electrical Engineers (IEEE®) 802.16p, 802.16n, 802.16m-2011, 802.16h-2010, 802.16j-2009, 802.16-2009. In another example, the electronic device 1610 may provide a secure wireless area network (WLAN), secure PAN, or private wireless Wide Area Network (WAN) to communicate with a device. The electronic device 1610 in the WLAN may use the WI-FI® technology and IEEE® 802.11 standards defined by the WI-FI ALLIANCE® such as the IEEE® 802.11-2012, IEEE® 802.11ac, or IEEE® 802.11ad standards. Alternatively, the devices in the WLAN may use other technologies and standards. Similarly, the electronic device 1610 in the PAN or WPAN may use the BLUETOOTH® technology and IEEE® 802.15 standards defined by the BLUETOOTH® Special Interest Group, such as BLUETOOTH® v1.0, BLUETOOTH® v2.0, BLUETOOTH® v3.0, or BLUETOOTH® v4.0. Alternatively, the electronic device 1610 in the secure PAN may use other technologies and standards. In another embodiment, the communications network may be a ZIGBEE® connection developed by the ZIGBEE® Alliance such as IEEE® 802.15.4-2003 (ZIGBEE® 2003), IEEE® 802.15.4-2006 (ZIGBEE® 2006), IEEE® 802.15.4-2007 (ZIGBEE® Pro). The WAN or PWAN may be used to transmit data over long distances and between different LANs, WLANs, metropolitan area networks (MANs), or other localized computer networking architectures.

In one embodiment, the electronic device 1610 can communicate data with the other devices via another device, such as a smartphone or tablet computing device. For example, the communication interface 1690 can pair with a smartphone via the wireless network. The smartphone can receive data using the wireless network and can communicate the data to the other device. In another embodiment, the electronic device 1610 may communicate information with the other device via repeaters or a relay system. For example, a user of the electronic device 1610 may be outside a coverage area for the cellular network or the wireless network, e.g., a farm worker out in the field. In this example, the electronic device 1610 can determine that it is outside the coverage area and switch to communicating via the repeaters or the relay system.

In one embodiment, the electronic device 1610 can determine it is outside a coverage area when it does not receive a signal from the cellular network or the wireless network. In another embodiment, the electronic device 1610 can ping the cellular network or the wireless network (such as a tower within the cellular network or the wireless network) and determine that it is outside the coverage area when the electronic device 1610 does not receive a reply to the ping. In another embodiment, multiple electronic devices 1610 can communicate with each other to form a piconet. In this embodiment, a first electronic device can determine it is outside the coverage area and can scan for a second electronic device, where the second electronic device is in the coverage area or in communication with another electronic device in the coverage area. When the first wearable safety finds the second electronic device, the electronic device can communicate information to an end device or to the cellular network or the wireless network via the second electronic device.

The processor 1603 may include a first sensor interface 1607 for receiving sensor data from the physiological sensor(s) 1602, a second sensor interface 1608 for receiving sensor data from the Newtonian sensor(s) 1604, a third sensor interface 1609 for receiving sensor data from the environmental sensor(s) 1605, a fourth sensor interface 1610 for receiving sensor data from the location sensor(s) 1606, and a processing element 1611. The processing element 1611 in turn may include a correlator 1613, a baseliner 1615 and/or an alerter 1617. The memory device 1608 may also include, without limitation, a sensor module 1616, physiological data 1624, environmental data 1626, Newtonian data 1628, and profile data 1630, location data 1632.

The electronic device 1610 may include the sensor array 120 (FIG. 1) with two or more sensors. In the depicted embodiment, the electronic device 1610 may include one or more physiological sensors 1602, one or more Newtonian sensors 1604, one or more environmental sensors 1605, one or more location sensors 1606, or a combination thereof. In some instances, the Newtonian sensors 1604 may be physiological sensors. That is, in some embodiment, the activity level may be determined from one or more physiological measurements.

A physiological measurement may be any measurement related to a living body, such as a human's body or an animal's body. The physiological measurement is a measurement made to assess body functions. Physiological measurements may be simple, such as the measurement of body or skin temperature, or they may be more complicated, for example measuring how well the heart is functioning by taking an ECG (electrocardiograph), or determining a hydration condition of the body. Physiological measurements may also include motion and/or movement of the body. In some cases, these physiological measurements may be taken as an aggregate, e.g., as physiological data, with which to correlate to other physiological measurements, a physiological parameter, and/or an environmental parameter.

A parameter may be considered a measurable quantity (such as heart rate, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 1602 may include a sweat rate sensor, a pulse oximeter sensor, an electrocardiography (ECG) sensor, a fluid level sensor, an oxygen saturation sensor, a body core temperature sensor, a skin temperature sensor, a plethysmograph sensor, a respiration sensor, a breath rate sensor, a cardiac sensor (e.g., a blood pressure sensor, a heart rate sensor, a cardiac stress sensor, or the like), an impedance sensor (e.g., bio-impedance spectroscopy sensor), an optical sensor, a spectrographic sensor, an oxygen saturation sensor, or humidity and/or temperature sensors. Alternatively, other types of sensors may be used to measure physiological measurements, including measurements to determine activity levels of a person wearing the electronic device.

The Newtonian sensors 1604 may be any of the physiological sensors described above, but in some cases, the Newtonian sensors 1604 are activity or motion sensors, such as, for example, a gyroscope sensor, a vibration sensor, an accelerometer sensor (e.g., a sensor that measures acceleration and de-acceleration), a three-dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 1602 may be used for specific physiological measurements.

In one embodiment, an environmental measurement may be any measurement of an area approximate or adjacent a user. The environmental sensors 1605 may be a humidity sensor, an ambient temperature sensor, an altitude sensor, a barometer, and so forth. A location measurement may be any measurement of a location of the user or a movement of the user. The location sensor 1606 may be a global positioning system (GPS), a triangulation system, or a location sensor. One or a combination of the physiological data 1624, the environmental data 1626, the Newtonian data 1628, the profile data 1630, and the location data 1632 may be obtained from other sources such as through the network from sources reachable in the cloud or online.

In another embodiment, the environmental measurement may be any measurement of a local or central location measurement of where a user is located. For example, one or more environmental sensors 1605 may be located at a location within a threshold radius of the user, such as a threshold radius from the user location. In this example, the environmental sensors 1605 can take environmental measurements and relay the information to the electronic device 1610 or to a communication hub that has a communication channel established with the electronic device 1610. Alternatively, the environmental sensors 1605 can take environmental measurements and relay the information to a processing hub that can analyze the environmental measurements to determine selected environmental factors (such as a humidity level, a heat index, and so forth) and can communicate the environmental factors to the electronic device 1610 or to another electronic device. In another embodiment, the processing hub can receive the environmental measurements from the environmental sensors 1605 and other measurements (such as physiological measurements) from the electronic device 1610. The processing hub can analyze the environmental measurements and the other measurements to determine selected result data, such as a hydration level of a user or a health level of the user. In another embodiment, the electronic device 1610 can take a first set of environmental measurements and the local environmental sensors 1605 can take a second set of environmental measurements. The first set of environmental measurements and the set of environmental measurements may be combined or aggregated and the processing hub and/or the electronic device 1610 can analyze the aggregated environmental measurements.

In another embodiment, the environmental measurements may be from an environmental information outlet or provider. For example, the environmental information outlet or provider is a weather station, a news station, a television station, an online website, and so forth. The electronic device 1610 or the processing hub can receive the environmental information from the environmental information outlet or provider can use the environmental information to determine selected physiological and/or environmental data or factors.

The first sensor interface 1607 may be coupled with the one or more physiological sensors 1602, a second sensor interface 1608 may be coupled with the one or more Newtonian sensors 1604, a third sensor interface 1609 may be coupled with the one or more environmental sensors 1605, and a fourth sensor interface 1610 may be coupled with the one or more location sensors 1606. The processing element 1611 may be operable to execute one or more instructions stored in the memory device 1608, which may be coupled with the processor 1603. In some cases the processing element 1611 and memory device 1608 may be located on a common substrate or on a same integrated circuit die. Alternatively, the components described herein may be integrated into one or more integrated circuits as would be appreciated by one having the benefit of this disclosure. The memory device 1608 may be any type of memory device, including non-volatile memory, volatile memory, or the like. Although not separately illustrated the memory device may be one or more types of memory configured in various types of memory hierarchies.

The memory device 1608 may store physiological data 1624, such as current and past physiological measurements, as well as profile data 1630, including user profile data, bibliographic data, demographic data, and the like. The physiological data 1624, and in some cases the profile data 1630, may also include processed data regarding the measurements, such as statistical information regarding the measurements, as well as data derived from the measurements, such as predictive indicators, results, and/or recommendations.

In one example, the profile data 1630 may also include information connected to user profiles of the users that wear the electronic device 1610, such as a gender of the user, an age of the user, a body weight or mass of the user, a health status of the user, a fitness level of the user, or a family health history of the user. In another example, the profile data 1630 may include occupational information of the users that wear the electronic device 1610, such as a job type, a job title, whether the job is performed indoors or outdoors, a danger level of the job, and so forth. For example, the job types may include an elderly live-at-home job, an oil driller, a construction worker, a railroad worker, a coal mine worker, a job in confined spaces, a fireman, a construction worker, an outdoor worker, an office worker, a truck driver, a child, or a disabled individual.

In one example, the electronic device 1610 can receive the profile data 1630 via a touch screen device integrated into the electronic device 1610 or coupled to the electronic device 1610. In another example, the electronic device 1610 can receive the profile data 1630 via a communication port of the electronic device 1610. For example, the electronic device 1610 can receive profile data 1630 from another device via a wired communication connection (e.g., a universal serial bus) or via a wireless communication connection (e.g., a BLUETOOTH® communication technology).

The profile data 1630 may also be linked to various physiological data 1624 and Newtonian data 1628 and be tracked over time for the users. The profile data 1630 may also include baselines of physiological parameters for respective users. In one example, the baselines are of a heart rate, a blood pressure, bio-impedance, skin temperature, oxygen levels, hydration levels, electrolyte levels and so forth. When the baselines are included with the user profiles, the user profiles may be referred to as baseline profiles for the respective users.

The memory device 1608 may also store one or a combination of the environmental data 1626, the Newtonian data 1628, the profile data 1630, and the location data 1632. The Newtonian data 1628, environmental data 1626, or location data 1632 may be current and past measurements, as well predictive data for predictive modeling of activity levels, environmental levels, or locations. The memory device 1608 may store instructions of the sensor module 1616 and instructions and data related to the correlator 1613, the baseliner 1615 and the alerter 1617, which perform various operations described below.

In particular, the sensor module 1616 may perform operations to control the physiological sensors 1602, Newtonian sensors 1604, environmental sensors 1605, and location sensors 1606, such as when to turn them on and off, when to take a measurement, how many measurements to take, how often to perform measurements, and so forth. For example, the sensor module 1616 may be programmed to measure a set of physiological measurements according to a default pattern or other adaptive patterns to adjust when and how often to take certain types of measurements. The measurements may be stored as the physiological data 1624, the environment data 1626, and the Newtonian data 1628, location data 1632, and some of them may also be integrated as a part of the profile data 1630, as discussed.

In the depicted embodiment, the processing element 1603 (e.g., one or more processor cores, a digital signal processor, or the like) executes the instructions of the sensor module 1616 and those related to the correlator 1613, the baseliner 1615, the alerter 1617 and possibly other modules or routines. Alternatively, the operations of the sensor module 1616 and the correlator 1613, the baseliner 1615, and the alerter 1617 may be integrated into an operating system that is executed by the processor 1603. In one embodiment, the processing element 1611 measures a physiological measurement via the first sensor interface 1607. The processing element 1611 may measure an amount of activity of the electronic device 1610 via the second sensor interface 1608. The amount of activity could be movement or motion of the electronic device 1610 (e.g., by tracking location), as well as other measurements indicative of the activity level of a user, such as heart rate, body temperature, skin luminosity, or the like. The processing element 1611 measures an environmental measurement via the third sensor interface 1609. The processing element 1611 measures a location measurement via the fourth sensor interface 1610.

In one embodiment, the Newtonian sensors 1604 may include a hardware motion sensor to measure at least one of movement or motion of the electronic device 1610. The processing element 1611 may determine the amount of activity-based the movement or motion of the electronic device 1610. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 1603 may further execute instructions to facilitate operations of the electronic device 1610 that receive, store and analyze measurement data, environmental data, location data, and profile data. The indicator(s) 1618 may include one or more of a light, a display, a speaker, a vibrator, and a touch display, usable to alert the user to take actions in response to trending levels of: physiological parameters during or after physical activity and/or prepare for undertaking anticipated physical activity; environmental parameters; activity parameters, or location parameters.

In some embodiments, for example, the correlator 1613 may analyze measurement data to correlate physiological data, environmental data, activity data, location data, or user experienced feedback with a physiological parameter, environmental parameter, activity parameter, a location parameter, or user experienced feedback to predict a change in a level of the physiological parameter, environmental parameter, activity parameter, or a location parameter. In one embodiment, the user experienced feedback may be physiological or psychological symptoms experienced by the user. For example the physiological or psychological symptoms may include: headaches, dizziness, tiredness, mental fatigue, increased thirst, dry mouth, swollen tongue, physical weakness, confusion, sluggishness, and so forth.

Such prediction may enable timely and accurate recommendations to a user in terms of hydrating, adjusting effort levels or other specific actions to address a trend or a change in the physiological parameter, the environmental parameter, the activity parameter, or the location parameter. The recommendations may be displayed in the display 1680, sent via an alert through one of the indicator(s) 1618 or displayed on another device such as a smartphone or tablet or another computing device.

In another embodiment, the correlator 1613 may also track and analyze Newtonian data of the user related to physiological or determined parameters (such as heart rate, oxygenation, skin luminosity, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the electronic device 1610 may track activity data over time, intelligently and continuously (or periodically) analyze all of this information, and alert the user through the indicator(s) 1618 to take a specific action at a proper time before a start of a dehydration condition. The specific action may include to hydrate extra hours before physical activity and to eat at least two hours before any physical activity, or other such timing that may be general to most users, or customized to a training or nutrition routine of a specific user.

In another embodiment, the correlator 1613 can build an individualized profile for the user. The correlator 1613 can receive the individualized profile information from an input device of the electronic device 1610. For example, the correlator 1613 can receive the individualized profile information from a touch screen of the electronic device 1610. In another example, the correlator 1613 can receive the individualized profile information from a device in communication with the electronic device (such as via a USB port or using a BLUETOOTH® technology). In another embodiment, the electronic device 1610 may include a memory that stores the individualized profile information for the user.

The individualized profile may include physiological information associated with the user. For example, the physiological information may include a hydration condition, an average heart rate of the user, an age of the user, a health level of the user, and so forth. The individualized profile can also include information associated with a location or environment that the user is located. For example, the individualized profile may include: humidity level information, such as when the user is located in a dry climate or in a humid climate; altitude level information, such as when the user is located at a relatively high altitude or a relatively low altitude; seasonal information, such as if it is winter where the user is located or summer. The correlator 1613 can also determine an environmental effect on the user for the location where the user is located. For example, if the user is located at their home that is at a high altitude with a dry climate and it is a winter season, the correlator 1613 can determine that the user is acclimated to high altitudes, dry climates, and the winter season. The correlator 1613 can also update the user profile when the user changes location. For example, when the user leaves their home location and goes on a vacation to a location that is at a low altitude, a humid climate, and it is a summer season, the correlator 1613 can determine that the user is not acclimated to the low altitude, humid climate, and summer season.

In one embodiment, the electronic device 1610 can alert the user of the changes to the individualized profile. In another embodiment, the electronic device 1610 can alert the user of the changes to effects associated with the changes to the individualized profile. For example, the electronic device 1610 can access a table of predetermined effects of the user changing their user profile. In one example, the table can indicate that when the user switches from a low altitude to a high altitude location, the user may experience altitude sickness. In another example, the table can indicate that when the user switches from a dry climate to a humid climate location, an ability of the user's body to cool itself down when an ambient temperature is relatively high. In another embodiment, the table can indicate when the current user profile indicates safety risks or physiological performance changes.

In another embodiment, the individualized profile can also include information associated with clothing or apparel worn by the user of the electronic device 1610. For example, the individualized profile can indicate that a user may wear different types of apparel for different environments including: a thickness of fabric; a type of a fabric, such as wool or cotton; a number of clothes layers worn by the client; accessories worn by the client, such as hard hats, steeled toed shoes, safety goggles, safety belts, and so forth; and gender types of apparel, such as women and men's apparel. In one example, the correlator can adjust measurement information or measurement results based on the different types of clothing or apparel. For example, the correlator 1613 can determine that the user is a firefighter and is wearing multiple layers of clothing to protect against fire. In this example, the correlator 1613 can determine that a cause of a hydration level of the user decreasing is the multiple layers of clothing cause the firefighter to sweat more and lose more fluid than a typical number of layers of clothing worn by the user.

In one embodiment, the alerter 1617 may decide the most appropriate timing and mode of alert, whether through one of the indicator(s) 1618, the display 1680 or another device such as a smartphone, tablet or the like. The type of indicator used to alert the user may also be customized to or by the user.

In one embodiment, the correlator 1613 may determine a correlation between different data points or data sets of the input data (such as data collected from different sensors, devices, or obtained from the cloud or online). The correlator 1613 may determine different types of correlations of the data points or data sets. In one example, the correlator 1613 may execute a Pearson product moment correlation coefficient algorithm to measure the extent to which two variables of input data may be related. In another example, the correlator 1613 may determine relations between variables of input data based on a similarity of rankings of different data points. In another example, the correlator 1613 may use a multiple regression algorithm to determine a correlation between a data set or a data point that may be defined as a dependent variable and one or more other data sets or other data points defined as independent variables. In another example, the correlator 1613 may determine a correlation between different categories or information types in the input data.

In further examples, when the correlator 1613 determines a correlation between the different data points or data sets, the correlator 1613 may use the correlation information to predict when a first event or condition may occur based on a second event or condition occurring. In another example, when the correlator 1613 determines a correlation between the different data points or data sets, the correlator 1613 may use the correlation information to determine a hydration condition. As discussed in the preceding paragraphs, a hydration may be an event that negatively impacts a user's safety or health. In another example, when the correlator 1613 determines a correlation between the different data points or data sets, the correlator 1613 may use the correlation information to determine a cause of a condition and/or event, such as a hydration condition.

Additionally, or alternatively, the correlator 1613 may determine a correlation between physiological data 1624, environmental data 1626, Newtonian data 1628, profile data 1630, and location data 1632. For example, the input data may include hydration level data (physiological data) and ambient temperature data (environmental data). In this example, the correlator 1613 may identify a correlation between an increase in the ambient temperature, a decrease in a hydration level of a user, and a heat stroke. The correlator 1613 may identify the correlation between the ambient temperature, the hydration level, and the heat stroke by using a regression algorithm with the heat stroke as an independent variable and the ambient temperature and the hydration level as dependent variables. When the correlator 1613 has identified the correlation between the heat stroke, the ambient temperature, and the hydration level, the correlator 1613 may predict a heat stroke based on a change in a hydration level of a user or a rate of change of a hydration level of a user and a change in the ambient temperature or a rate of change in the ambient temperature.

Additionally, or alternatively, the correlator 1613 may determine a correlation between a fatigue event, an altitude level, and an oxygenation level of a user. For example, the correlator 1613 may determine a correlation between an increase in the altitude level, a decrease in the oxygenation level of the user, and an increase in a fatigue event. When the correlator 1613 determines the correlation between the altitude level, the oxygenation level, and the fatigue event, the correlator 1613 may predict an increase or decrease in a probability of a hydration condition change based on a change in the oxygenation level of the user and the altitude level at which the user is currently at. In one example, the correlator 1613 can use the individualized profile information (as discussed in the preceding paragraphs) of the user to determine the predicted increase or decrease in the probability of a hydration condition change. For example, the correlator 1613 can determine a change in altitude level of the user from a relatively low altitude to a relatively high altitude. The correlator 1613 can use the individualized profile information to determine that the user is acclimated to the relatively high altitude (such as if they live at a high altitude) and adjust the predicted increase or decrease in the probability of a hydration condition change for the change in altitude in view of the individualized profile information. For example, the correlator 1613 can predict that the change from the low altitude to the high altitude will not increase or decrease the probability of a user becoming dehydrated.

In a further example, the correlator 1613 may identify a correlation between location information and physiological data of a user. For example, the correlator 1613 may determine a location of a user for at a period of time, such as by using GPS sensor data or triangulation sensor data. In this example, the correlator 1613 may receive physiological measurement data (such as heart rate measurement data, optical spectroscopy data, hydration level measurement data, blood pressure measurement data, and so forth). The correlator 1613 may correlate the location of the user with the physiological measurement data to increase an accuracy of data analysis, a diagnosis, or result data and/or provide additional details regarding a cause of a change in a hydration condition.

In one example, the correlator 1613 may determine that a user is at work in an office location. When the correlator 1613 detects an increase in a heart rate or a blood pressure of a user, the correlator 1613 may correlate heart rate or blood pressure data and the location information to determine a cause of the cognitive ability reduction event. For example, when a heart rate or blood pressure of a user increases while at work in an office, the correlator 1613 may determine that the heart rate or blood pressure increase may be due to psychological causes (such as stress) rather than physiological causes (such as exercising or working out) because the user is at a location where the user is not likely to physically exert himself or herself.

In another example, the correlator 1613 may determine an occupation of the user, such as by using the profile data 1630. In one embodiment, the correlator 1613 can determinate that the occupation of the user is a higher risk occupation (e.g., a statistically more dangerous occupation). For example, the correlator 1613 can access a database or list (stored at the memory device 1608 or externally) that includes information associated with an occupation, such as environmental exposure. When the correlator 1613 detects that the occupation of the user is a higher risk occupation (e.g., an occupation with a risk level that exceeds a threshold value), the correlator 1613 may correlate heart rate data, blood pressure data, hydration level data, with the occupational information to determine a cause of a hydration condition change. For example, when a heart rate and blood pressure of a user increases and a hydration level of the individual decreases while the individual is working at an oil refinery or on a farm, the correlator 1613 may determine that the heart rate or blood pressure increase may be due to physiological influences of the occupation (such as strenuous labor or no breaks) rather than psychological causes (such as stress) because the occupation where the individual is working at is likely to include physical exertion.

In a further example, the correlator 1613 may use a multiple regression algorithm to determine a correlation between multiple data points or data sets and a hydration condition. For example, the correlator 1613 may receive heart rate data, skin temperature, bio-impedance data, skin luminosity and hydration level data of a user. In this example, the correlator 1613 may determine a correlation between these types of physiological data and a dehydration event of the individual. For example, the physiological data could be from optical spectroscopy (skin luminosity) and/or bio-impedance data. The correlator 1613 may then determine that as the bio-impedance of a user increases and skin luminosity decreases, a probability of a dehydration event occurring increases.

Additionally, or alternatively, the correlator 1613 may filter out a correlation determination (e.g., a determination that data points or data sets and a hydration condition may be correlated) when a correlation level is below a threshold level. For example, when the correlator 1613 determines that there may be a 30 percent correlation between a skin temperature or a bio-impedance level of a user and a fall event, the correlator 1613 may filter out or disregard the correlation information when determining a cause of the fall event. In another example, the correlator 1613 can use a learning algorithm or machine learning to determine when to filter out a correlation determination. For example, at a first instance of a fall, there may be a 30 percent correlation between a skin temperature or a bio-impedance level of a user and a fall event. The correlator 1613 can monitor multiple fall events and use machine learning to determine that the initial 30 percent correlation is actually a 60 percent correlation and adjust the filter to not filter out the correlation between the skin temperature or the bio-impedance level of a user and a fall event or assign the correlation of the skin temperature or the bio-impedance level of a user and a fall event a different weight.

Additionally, or alternatively, the correlator 1613 may filter out the correlation determination based on a schedule of a user. For example, when the correlator 1613 determines that a user is taking a lunch break, off of work, or sleeping, the correlator 1613 may filter out environmental conditions that are associated with the occupation of the user, e.g., the correlator 1613 can filter out false positives.

Additionally, or alternatively, the correlator 1613 may discount or weight a correlation determination based on the correlation level of the correlation determination. For example, when the correlator 1613 determines that there may only be a 30 percent correlation between an occupation of a user and a hydration level of a user, the correlator 1613 may discount or assign a lower weight to the correlation determination (relative to a higher correlation percentage such as 90 percent) when determining a change in hydration condition.

Additionally, or alternatively, the correlator 1613 may assign weights to different factors, such as: physiological data 1624 (e.g., different types or qualities of physiological parameters), environmental data 1626 (e.g., different types or quality of environmental parameters), Newtonian data 1628 (e.g., different types or quality of Newtonian parameters), profile data 1630, location data 1632 (e.g., different types or quality of location parameters), a time of day, and so forth. In one example, the correlator 1613 may assign a first weight to hydration level data of a user and a second weight to profile data of a user when determining a probability of a change in hydration condition for a user. In this example, when determining the probability of a change in a hydration condition, the correlator 1613 may assign a higher weight to the hydration level data relative to the profile data, for example.

The correlator 1613 may additionally, or alternatively, use predetermined weights for the physiological data 1624, environmental data 1626, Newtonian data 1628, profile data 1630, and location data 1632. In another example, the correlator 1613 may receive user-defined or predefined weights from an input device indicating the weights for the different physiological and/or environmental data. In another example, the correlator 1613 may determine the weights to assign to the physiological data 1624, environmental data 1626, Newtonian data 1628, profile data 1630, and location data 1632 based on correlation levels of the physiological data 1024, environmental data 1626, Newtonian data 1628, profile data 1630, and location data 1632. For example, when a correlation level between a hydration condition and a heart rate of a user may be relatively low over a threshold period of time and/or under a threshold number of different conditions, the correlator 1613 may assign a low weight to heart rate data when determining a cause of a change in hydration condition.

In one example, the correlator 1613 may assign different weights to one or more of the physiological data 1624, environmental data 1626, Newtonian data 1628, profile data 1630, and location data 1632 based on other physiological data 1624, environmental data 1626, Newtonian data 1628, profile data 1630, and location data 1632. For example, based on a location of a user, the correlator 1613 may assign a first weight to environmental data 1626 and a second weight to profile data 1630. In another example, the correlator 1613 may assign weights to different hydration conditions.

Additionally, or alternatively, the correlator 1613 may use environmental data 1726 or location data 1632 to determine a cause of a change in hydration condition. For example, when a user is located at a fitness facility working out, the correlator 1613 may increase a weight for a physical exertion related to a change in a hydration condition occurring because of in physical exertion of a user (such as an increase in a heart rate or decrease in a hydration level of a user). In another example, when a user is located at home in bed resting or sleeping, the correlator 1613 may correlate a location of the user with the hydration condition of the user. In this example, the correlator 1613 may determine that a decrease in probability of a change in a hydration condition occurring due to a user being is located in their bedroom for a threshold period of time (e.g., a safer environment).

In one embodiment, the correlator 1613 can determine a weighting of measurement information or physiological information using medical evaluation information. In one example, the medical evaluation information includes medical evaluation information of the user, such as a medical physical. The medical evaluation information may include: medical history and health history information, such as whether the user is a smoker or a non-smoker; a user's blood pressure information; hereditary diseases information; a user's sexual health information; a user's dietary information, a user's exercise routine information, such as how often the user exercises; a user's heart or lung examine information; and so forth. In one example, the correlator 1613 can use the medical evaluation information to set initial weight for different data types. The correlator can update or adjust the weights for the different data types using machine learning. For example, the physiological data 1624, environmental data 1626, and Newtonian data 1628 is assigned a first set of weights based on the medical evaluation information. As the electronic device 1610 uses the sensors to collect the physiological data 1624, environmental data 1626, and the Newtonian data 1628, the correlator 1613 can use the physiological data 1624, the environmental data 1626, and the Newtonian data 1628 to customize the weighting of the measurement information or physiological information to the individual. For example, the correlator 1613 can receive medical evaluation information for the user input device of the electronic device 1610 using an input device of the electronic device 1610.

The correlator 1613 may track, sort and/or filter input data. The input data may include: user schedule information, such as a daily schedule of the user; survey information, such as information received from surveys of individuals; research information, such as clinical research information or academic research information associated with one or more hydration conditions of the electronic device; and so forth.

The correlator 1613 may use location-based tracking and/or scheduling information of the user in determining an expected or probable change in a hydration condition. For example, when a user is a member of a sports team, the user's schedule may include practice schedule information and/or game schedule information. In this example, the correlator 1613 may use the schedule information to anticipate that the user may be participating in physical activity and increase a probability that a change in hydration condition may occur.

The correlator 1613 may use timer information determining an expected or probable occurrence of a change in a hydration condition. For example, the correlator can monitor how long it may have been since a user took a break or consumed water. In this example, as the length of time increase between a break or water consumption, the probability that a change in hydration condition may occur increases. In another example, the correlator can use the timer information to periodically request a response from the user. For example, when a change in hydration condition has not occurred within a threshold amount of time that would trigger a user response, the electronic device can request a user response from the user when the threshold amount of time has been exceeded.

In another example, the correlator 1613 can have a work mode (the user is at work) and a home mode (the user is at home), where a type of environmental condition that the electronic device monitors for and/or a probability of a change in a hydration condition occurring can increase or decrease when switching between the work mode and the home mode. For example, when the user has a high-risk occupation, the correlator 1613 can monitor for a change in hydration condition related to the high-risk occupation when the correlator is in a work mode and switch to monitoring for changes in a hydration condition related to low risk activities when the correlator is in a home mode.

In another example, the correlator 1613 may use the scheduling information in correlation with a location of the user to determine an expected or probable change in a hydration condition. For example, the scheduling information may indicate that the user may be scheduled to attend a lecture at a physical fitness facility and the correlator 1613 may adjust the types or probabilities of a change in a hydration condition occurring in view of the scheduling information. In this example, while the correlator 1613 may typically increase a probability of a change in hydration condition occurring for the user in anticipation of physical activity based on the location information (e.g., the physical fitness facility), the correlator 1613 may adjust the adjust the types or probabilities of a change in a hydration condition occurring in view of the scheduling information that the user may be attending a lecture rather than working out.

Additionally, or alternatively, the correlator 1613 may track and update activity levels of users and correlate these levels with hydration conditions over time. For example, the GPS sensor of the electronic device 1610 may indicate that the user usually works out at the gym on Monday, Wednesday and Friday at 7 a.m. and goes on a long bike ride on Saturday, usually starting about 8:30 a.m. Although these activities may not be available within the scheduling information or data of the electronic device 1610 (or another tethered device), the correlator 1013 may execute machine learning to add to a user's activity data these events that normally occur.

The electronic device 1610 may store historical or previous hydration condition information of the user. In one example, the correlator 1013 may store the historical information on the memory device 1608 of the electronic device 1610. In another example, the correlator 1613 may use the communication device 170 (illustrated in FIG. 1), the communication unit 1070 (illustrated in FIG. 10), or the communication interface 1690 to store the hydration condition information on a memory device coupled to or in communication with the electronic device, such as a cloud-based storage device or a memory device of another computing device. In another example, the correlator 1613 may be part of a cloud-based system or the other computing device, as will be discussed in more detail with reference to FIGS. 13 and 14.

The correlator 1618 may filter and/or sort hydration condition information. In one example, the correlator 1618 may receive a filter or sort command from the electronic device or an input device to filter and/or sort the hydration information. In another example, the filter or sort command may include filter parameters and/or sort parameters.

In another example, the correlator 1613 may sort and/or filter the input data based on a trending of hydration conditions. For example, the correlator 1613 may sort hydration conditions that may be trending in an increasing direction or a decreasing direction and may sort the hydration conditions based on the trending. In this example, different hydration conditions for a user may be trending in different directions, such as a dehydration events of a user may be increasing in trending and fall events may be stable or stagnant.

In another embodiment, the baseliner 1615 may receive profile information from a new user to include any or a combination of gender, age, weight, health, fitness level, and family health histories. The health and fitness levels of the user may be based at least in part on physiological measurements received from the physiological sensor(s) 1602 and the activity data received from the Newtonian sensors 1604. The baseliner 1615 may then identify, from one or more baseline profiles of other users (e.g., a group of users), a baseline profile that is most-similar to the user profile based on a correlation between the user profile information and baseline profile information. The baseline profiles may include baseline information of a probability of a change in hydration conditions occurring for a user. The user profiles may include information about the types of hydration conditions that may be probable to occur for the user.

The baseliner 1615 may then be able to set a baseline against which to judge a hydration condition. In an alternate embodiment, the baseline profile that is most-similar to the user profile is identified from an aggregated baseline profile for one or more individuals corresponding to the one or more baseline profiles. Alternatively, or additionally, the most-similar profiles may look at a hydration condition that occurs for the individual as compared to a group. For example, the user may be most similar to another individual because they both react physiologically similarly to hot temperatures outside. In another example, the user may have a similar dehydration profile to the most-similar profile, meaning, when the user works out the user may reach a dehydration level at a certain point in time that substantially matches the timing of the most-similar profile.

The electronic device 1610 may further receive survey information and/or research information from an input device with which to build or add to the user and/or baseline profiles. For example, the electronic device 1610 may receive survey information that includes: gender information, age information, physical weight information, general health information, family information, fitness level information, and so forth. In one example, the correlator 1613 may determine a correlation between the survey information and user input data. For example, the correlator 1613 may correlate the age, weight, fitness level, and general health level of a user with survey information from other individuals to determine a correlation between the survey information for the individual and the other individuals. In this example, the baseliner 1615 may set a baseline for a measurement of the electronic device 1610 for the individual based on baselines for the other individuals with the same or similar survey information.

In another example, the correlator 1613 may correlate the user information with research information (such as research papers, clinical studies, and so forth). For example, the electronic device may retrieve research information related to a physiological parameter, the correlator 1613 may then correlate the research information with hydration conditions for the user to generate a research correlation. The baseliner 1615 may then adjust the baseline set for the user related to the hydration conditions in response to the research correlation.

The correlator 1613 can store hydration condition information in a hydration condition database 1612. In one embodiment, the correlator 1613 can determine parameters associated with hydration conditions. The parameters may include threshold values for measurements or data values, such as physiological sensor measurements, environmental sensor measurements, Newtonian sensor measurements, location sensor measurements, or profile data 1630. The correlator 1613 can store the hydration condition and the associated hydration parameters in the hydration condition database 1612. For example, the correlator 1613 can determine that parameters for a heat stroke event may be a skin temperature above a 100-degree temperature, blood pressure above 160 systolic, and a bio-impedance level above 16000 ohms (e.g., a dehydration level threshold). In this example, the correlator 1613 can determine these parameters can store the hydration condition with the associated parameters in the hydration condition database 1612. In another example, the store predetermined hydration conditions with the associated parameters. In another example, the hydration condition database 1612 can receive the hydration conditions and the associated parameters from another device or server 1694.

The preceding examples are intended for purposes of illustration and are not intended to be limiting. The correlator 1613 may identify a correlation between various data points, data sets, data types, and/or hydration conditions. After having a correlation that informs, for example, a heat stroke event, the hydration level, and/or oxygenation level of the user, and further in consideration of a present activity level of the user, the alerter 1617 may alert the user at the proper time when to hydrate or how to moderate activity levels to avoid or minimize a dehydrated condition.

A module as used herein refers to any combination of hardware, software, and/or firmware. As an example, a module includes hardware, such as a microcontroller, associated with a non-transitory medium to store code adapted to be executed by the micro-controller. Therefore, a reference to a module, in one embodiment, refers to the hardware, which is specifically configured to recognize and/or execute the code to be held on a non-transitory medium. Furthermore, in another embodiment, use of a module refers to the non-transitory medium including the code, which is specifically adapted to be executed by the microcontroller to perform predetermined operations. And as may be inferred, in yet another embodiment, the term module (in this example) may refer to the combination of the microcontroller and the non-transitory medium. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices.

Use of the phrase 'configured to,' in one embodiment, refers to arranging, putting together, manufacturing, offering to sell, importing and/or designing an apparatus, hardware, logic, or element to perform a designated or determined task. In this example, an apparatus or element thereof that is not operating is still 'configured to' perform a designated task if it is designed, coupled, and/or interconnected to perform said designated task. As a purely illustrative example, a logic gate may provide a 0 or a 1 during operation. But a logic gate 'configured to' provide an enable signal to a clock does not include every potential logic gate that may provide a 1 or 0. Instead, the logic gate is one coupled in some manner that during operation the 1 or 0 output is to enable the clock. Note once again that use of the term 'configured to' does not require operation, but instead focus on the latent state of an apparatus, hardware, and/or element, wherein the latent state the apparatus, hardware, and/or element is designed to perform a particular task when the apparatus, hardware, and/or element is operating.

Furthermore, use of the phrases 'to,' 'capable of/to,' and or 'operable to,' in one embodiment, refers to some apparatus, logic, hardware, and/or element designed in such a way to enable use of the apparatus, logic, hardware, and/or element in a specified manner. Note as above that use of to, capable to, or operable to, in one embodiment, refers to the latent state of an apparatus, logic, hardware, and/or element, where the apparatus, logic, hardware, and/or element is not operating but is designed in such a manner to enable use of an apparatus in a specified manner.

A value, as used herein, includes any known representation of a number, a state, a logical state, or a binary logical state. Often, the use of logic levels, logic values, or logical values is also referred to as 1's and 0's, which simply represents binary logic states. For example, a 1 refers to a high logic level and 0 refers to a low logic level. In one embodiment, a storage cell, such as a transistor or flash cell, may be capable of holding a single logical value or multiple logical values. However, other representations of values in computer systems have been used. For example, the decimal number ten may also be represented as a binary value of 1010 and a hexadecimal letter A. Therefore, a value includes any representation of information capable of being held in a computer system.

Moreover, states may be represented by values or portions of values. As an example, a first value, such as a logical one, may represent a default or initial state, while a second value, such as a logical zero, may represent a non-default state. In addition, the terms reset and set, in one embodiment, refer to a default and an updated value or state, respectively. For example, a default value potentially includes a high logical value, i.e. reset, while an updated value potentially includes a low logical value, i.e. set. Note that any combination of values may be utilized to represent any number of states.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the foregoing specification, a detailed description has been given with reference to specific exemplary embodiments. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense. Furthermore, the foregoing use of embodiment and other exemplary language does not necessarily refer to the same embodiment or the same example, but may refer to different and distinct embodiments, as well as potentially the same embodiment.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here and generally, conceived to be a self-consistent sequence of operations leading to a specific result. The operations are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. The blocks described herein may be hardware, software, firmware or a combination thereof.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "defining," "receiving," "determining," "issuing," "linking," "associating," "obtaining," "authenticating," "prohibiting," "executing," "requesting," "communicating," or the like, refer to the actions and processes of a computing system, or similar electronic computing device, that manipulates and transforms data represented as physical (e.g., electronic) quantities within the computing system's registers and memories into other data similarly represented as physical quantities within the computing system memories or registers or other such information storage, transmission or display devices.

The words "example" or "exemplary" are used herein to mean serving as an example, instance or illustration. Any embodiment or design described herein as "example" or "exemplary" is not necessarily to be construed as preferred or advantageous over other embodiments or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," and so forth as used herein are meant as labels to distinguish among different elements and may not necessarily have an ordinal meaning according to their numerical designation.

What is claimed is:

1. A wearable device comprising:
    a housing comprising:
        a perimeter wall;
        a top wall;
        a bottom wall; and
        an inner cavity enclosed by the perimeter wall, the top wall, and the bottom wall, wherein:
            the perimeter wall defines a perimeter of the housing;
            the bottom wall is shaped to affix to a user; and
            the top wall, the bottom wall, and the perimeter wall form an inner cavity;
    a flume extending through the inner cavity, wherein the flume comprises:
        a first end disposed at the bottom wall;
        a second end disposed at the top wall; and
        a middle portion extending substantially parallel with the top wall;
    a sensor array comprising:
        an ambient humidity sensor integrated into a first port in the top wall;
        an air flow sensor integrated into the top wall of the housing;
        a skin temperature sensor integrated into the bottom wall of the housing;
        an ambient temperature sensor integrated into a second port in the top wall;
        a first vapor pressure sensor located at a first location of the middle portion of the flume; and
        a second vapor pressure sensor located at a second location, wherein the second location is a threshold distance from the first location;
    a sensor interface coupled to the sensor array, wherein the sensor interface is configured to:
        receive an ambient humidity measurement from the ambient humidity sensor;
        receive one or more measurements from the air flow sensor;
        receive a skin temperature measurement from the skin temperature sensor;
        receive an ambient temperature measurement from the ambient temperature sensor;
        receive a first vapor pressure measurement from the first vapor pressure sensor; and
        receive a second vapor pressure measurement from the second vapor pressure sensor; and
    a processor coupled to the sensor interface, the processor is configured to:
        calculate an air flow measurement from the one or more measurements from the air flow sensor;
        determine a baseline temperature from the ambient temperature measurement;
        determine an adjusted baseline temperature from the ambient humidity measurement and the air flow measurement;
        determine a hydration condition of the user from the adjusted baseline and the skin temperature measurement, wherein the hydration condition corresponds to a hydration level; and
        determine a sweat rate of the user using the first vapor pressure measurement and the second vapor pressure measurement generated by a pressure wave emanating from the user.

2. The wearable device of claim 1, wherein a membrane is disposed at the first end or the second end of the flume to filter fluid or particles.

3. The wearable device of claim 1, wherein:
    the first vapor pressure sensor comprises:
        a first humidity sensor integrated into the flume; and a first temperature sensor integrated into the flume;
    the second vapor pressure sensor comprises:
        a second humidity sensor integrated into the flume, wherein the second humidity sensor has a first spacing from the first humidity sensor;
        a second temperature sensor integrated into the flume, wherein the second temperature sensor has a second spacing from the first temperature sensor; and the sensor interface is configured to receive:
            a first humidity measurement from the first humidity sensor;
            a second humidity measurement from the second humidity sensor;
            a first temperature measurement from the first temperature sensor; and
            a second temperature measurement from the second temperature sensor.

4. The wearable device of claim 3, wherein the processor is further configured to:
    calculate the first vapor pressure measurement from the first humidity measurement and the first temperature measurement; and
    calculate the second vapor pressure measurement from the second humidity measurement and the second temperature measurement.

5. The wearable device of claim 1, wherein the wearable device further comprises a graphical user interface configured to receive user information from an input device, the user information comprising one or more of a height of the user, a weight of the user, or a gender of the user.

6. The wearable device of claim 5, wherein the processor is further configured to:

identify an initial hydration condition associated with user information in a database;
determine a water loss measurement from the sweat rate; and calculate an adjusted hydration condition from the initial hydration condition and the water loss measurement; and
display the adjusted hydration condition to the user, wherein the adjusted hydration condition corresponds to a hydration level.

7. A wearable device comprising:
a housing, wherein a bottom side of the housing is shaped to affix to a user, wherein a top side of the housing is opposite the bottom side of the housing;
a sensor array comprising:
an ambient humidity sensor;
an air flow sensor;
a skin temperature sensor;
an ambient temperature sensor;
a sensor interface coupled to the sensor array, wherein the sensor interface is configured to provide:
an ambient humidity measurement from the ambient humidity sensor;
an air flow measurement from the air flow sensor;
a skin temperature measurement from the skin temperature sensor; and
an ambient temperature measurement from the ambient temperature sensor; and
a processor coupled to the sensor array, the processor to:
determine a baseline condition using the ambient temperature measurement;
determine an adjusted baseline condition using the ambient humidity measurement and the air flow measurement; and
determine an adjusted hydration condition of the user using the adjusted baseline condition and the skin temperature measurement, wherein the adjusted hydration condition corresponds to a hydration level.

8. The wearable device of claim 7, further comprising:
a perimeter wall disposed around a perimeter of the housing between a top side and a bottom side, wherein the top side, bottom side, and perimeter wall form an inner cavity; and
a flume disposed in the inner cavity, wherein:
a first end of the flume is disposed at the bottom side; and
a second end of the flume is disposed at the top side, wherein the sensor array further comprises:
a first vapor pressure sensor located within the flume at a first location; and
a second vapor pressure sensor located within the flume at a second location.

9. The wearable device of claim 8, wherein:
the sensor interface is configured to:
take a first vapor pressure measurement using the first vapor pressure sensor; and
take a second vapor pressure measurement using the second vapor pressure sensor; and
the processor is configured to determine a sweat rate of the user using the first vapor pressure measurement and the second vapor pressure measurement.

10. The wearable device of claim 7, wherein the air flow sensor comprises:
a first heating element integrated into the housing;
a first temperature sensor integrated into the top side of the housing; and
a second temperature sensor integrated into the top side of the housing, wherein the sensor interface is further configured to provide a first temperature measurement from the first temperature sensor and a second temperature measurement from the second temperature sensor, wherein the first temperature measurement and the second temperature measurement comprise the air flow measurement from the air flow sensor.

11. The wearable device of claim 7, wherein the air flow sensor comprises a pressure sensor integrated into the housing, wherein the sensor interface is further configured to provide a pressure measurement from the pressure sensor, and wherein the pressure measurement is the air flow measurement from the air flow sensor.

12. The wearable device of claim 7, wherein:
the ambient humidity sensor is integrated into a first port in the top side of the housing;
the air flow sensor is integrated into the top side of the housing;
the skin temperature sensor is integrated into the bottom side of the housing; and
the ambient temperature sensor is integrated into a second port in the top side of the housing.

13. The wearable device of claim 12, wherein:
the first port comprises a first membrane to filter fluid and particles; and
the second port comprises a second membrane to filter fluid and particles.

14. The wearable device of claim 7, wherein:
the sensor interface is further configured to receive a plurality of air flow measurements from the air flow sensor; and
the processor is further configured to calculate an air flow measurement from the plurality of air flow measurements.

15. The wearable device of claim 7, further comprising a display to display the adjusted hydration condition to the user.

16. A wearable device comprising:
a housing comprising a perimeter wall disposed around a perimeter of the housing between a top wall and a bottom wall, wherein the bottom wall is shaped to affix to a user, wherein the top wall, bottom wall, and perimeter wall form an inner cavity;
a flume disposed in the inner cavity, wherein:
a first end of the flume is disposed at the bottom wall;
a second end of the flume is disposed at the top wall;
a sensor array comprising:
a first vapor pressure sensor located within the flume at a first location;
a second vapor pressure sensor located within the flume at a second location, wherein the second location is a threshold distance within the flume from the first location;
an ambient humidity sensor;
an air flow sensor;
a skin temperature sensor; and
an ambient temperature sensor;
a sensor interface coupled to the sensor array, wherein the sensor interface is configured to receive:
a first vapor pressure measurement from the first vapor pressure sensor;
a second vapor pressure measurement from the second vapor pressure sensor;
an ambient humidity measurement from the ambient humidity sensor;
an air flow measurement from the air flow sensor;
a skin temperature measurement from the skin temperature sensor; and an ambient temperature measurement from the ambient temperature sensor; and a processor coupled to the sensor interface, the processor configured to:
 determine a sweat rate of the user using the first vapor pressure measurement and the second vapor pressure measurement;
 determine a baseline temperature using the ambient temperature measurement;
 determine an adjusted baseline temperature using the ambient humidity measurement and the air flow measurement; and
 determine an adjusted hydration condition of the user using the adjusted baseline temperature and the skin temperature measurement, wherein the adjusted hydration condition corresponds to a hydration level.

17. The wearable device of claim 16, wherein:
the ambient humidity sensor is integrated into a first port in the top wall of the housing;
the air flow sensor is integrated into the top wall of the housing;
the skin temperature sensor is integrated into the bottom wall of the housing; and
the ambient temperature sensor is integrated into a second port in the top wall of the housing.

18. The wearable device of claim 17, wherein:
the first port comprises a first membrane configured to filter fluid and particles; and
the second port comprises a second membrane configured to filter fluid and particles.

19. The wearable device of claim 16, wherein:
the sensor interface is configured to receive a plurality of air flow measurements from the air flow sensor; and
the processor is configured to calculate an air flow measurement from the plurality of air flow measurements.

* * * * *